United States Patent
Fleming et al.

(10) Patent No.: US 11,234,657 B2
(45) Date of Patent: Feb. 1, 2022

(54) NON-INVASIVE MEASUREMENT TO PREDICT POST-SURGERY ANTERIOR CRUCIATE LIGAMENT SUCCESS

(71) Applicants: Rhode Island Hospital, Providence, RI (US); Children's Medical Center Corporation, Boston, MA (US)

(72) Inventors: Braden C. Fleming, East Greenwich, RI (US); Martha M. Murray, Sherborn, MA (US)

(73) Assignees: Rhode Island Hospital, Providence, RI (US); Children's Medical Center Corporation, Boston, MA (US)

(*) Notice: Subject to any disclaimer, the term of this patent is extended or adjusted under 35 U.S.C. 154(b) by 99 days.

(21) Appl. No.: 16/609,737

(22) PCT Filed: May 1, 2018

(86) PCT No.: PCT/US2018/030514
§ 371 (c)(1),
(2) Date: Oct. 30, 2019

(87) PCT Pub. No.: WO2018/204404
PCT Pub. Date: Nov. 8, 2018

(65) Prior Publication Data
US 2020/0069257 A1    Mar. 5, 2020

Related U.S. Application Data

(60) Provisional application No. 62/492,833, filed on May 1, 2017.

(51) Int. Cl.
*G06K 9/00* (2006.01)
*A61B 5/00* (2006.01)
(Continued)

(52) U.S. Cl.
CPC .......... *A61B 5/7275* (2013.01); *A61B 5/055* (2013.01); *A61B 5/4533* (2013.01);
(Continued)

(58) Field of Classification Search
CPC ................................................. A61B 5/7275
See application file for complete search history.

(56) References Cited

U.S. PATENT DOCUMENTS

| 2009/0072826 | A1 | 3/2009 | Hargreaves et al. |
| 2010/0256504 | A1 | 10/2010 | Moreau-Gaudry et al. |
| 2014/0136154 | A1 | 5/2014 | Bojarski et al. |
| 2014/0355852 | A1 | 12/2014 | Liew et al. |

(Continued)

FOREIGN PATENT DOCUMENTS

KR    20160133118 A   * 11/2016   ........ A61B 5/4533

OTHER PUBLICATIONS

KR-20160133118-A—English Translation (Year: 2016).*
(Continued)

*Primary Examiner* — Oneal R Mistry
(74) *Attorney, Agent, or Firm* — Mintz Levin Cohn Ferris Glovsky and Popeo, P.C.; Ingrid A. Beattie

(57) ABSTRACT

The current subject matter provides a tool for evaluating the risk of failure or the likelihood of success of surgery of healing ligaments and tendons in the body. In some embodiments, a region of a scan comprising one or more of an anterior cruciate ligament (ACL) or an ACL graft can be defined. A magnetic resonance (MR) imaging data set can be obtained. MR parameters characterizing a size and a quality of the ACL or ACL graft can be derived using the MR data. The MR parameters can be used as inputs to a predictive model. A score characterizing a likelihood of failure of the ACL or ACL graft in a human patient can be generated using the predictive model.

58 Claims, 37 Drawing Sheets

(51) Int. Cl.
*G06T 7/62* (2017.01)
*G06T 7/174* (2017.01)
*G16H 50/50* (2018.01)
*G16H 30/20* (2018.01)
*G16H 50/30* (2018.01)
*A61B 5/055* (2006.01)
*G01R 33/56* (2006.01)
*G06T 7/00* (2017.01)
*G06T 11/00* (2006.01)

(52) U.S. Cl.
CPC .......... *A61B 5/4585* (2013.01); *A61B 5/4851* (2013.01); *G01R 33/5608* (2013.01); *G06T 7/0016* (2013.01); *G06T 7/174* (2017.01); *G06T 7/62* (2017.01); *G06T 11/005* (2013.01); *G06T 11/008* (2013.01); *G16H 30/20* (2018.01); *G16H 50/30* (2018.01); *G16H 50/50* (2018.01); *G06T 2207/10088* (2013.01); *G06T 2207/30052* (2013.01)

(56) References Cited

U.S. PATENT DOCUMENTS

| | | | |
|---|---|---|---|
| 2017/0189119 A1* | 7/2017 | Yildirim | G16H 50/20 |
| 2018/0055405 A1* | 3/2018 | Peacock, III | A61B 5/748 |
| 2018/0284141 A1* | 10/2018 | Ayton | A61B 5/4842 |
| 2019/0142297 A1* | 5/2019 | Du | G01R 33/4828 |
| | | | 324/309 |
| 2019/0167179 A1* | 6/2019 | Arzy | A61B 5/7264 |

OTHER PUBLICATIONS

Bieicevicz et al. "MRI Volume and Signal Intensity of the ACL Graft Predicts Clinical, Functional and Patient Oriented Outcome Measures Following ACL Reconstruction." In: Am J Sports Med., Dec. 24, 2014 [online] [retrieved on Jul. 12, 2018 (Jul. 12, 2018)] Retrieved from the Internet <URL: https://www.ncbi.nlm.nih.gov/pmc/articles/PMC4344859/>.

International Search Report from corresponding International Application No. PCT/US2018/030514 dated Aug. 23, 2018, 2 pages.

* cited by examiner

NON-INVASIVE MEASUREMENT TO PREDICT POST-SURGERY ANTERIOR CRUCIATE LIGAMENT SUCCESS

CROSS REFERENCE TO RELATED APPLICATION

This application is a National Stage Entry of the International Patent Application No: PCT/US2018/030514, filed May 1, 2018, which claims the benefit of and priority to U.S. Provisional Patent application No. 62/492,833 filed May 1, 2017, and entitled "Non-Invasive Measurement To Predict Post-Surgery Anterior Cruciate Ligament Success", the entire contents of each of which are hereby expressly incorporated by reference herein.

STATEMENT REGARDING FEDERALLY SPONSORED RESEARCH OR DEVELOPMENT

This invention was made with government support under R01 AR065462 awarded by the National Institutes of Health. The government has certain rights in the invention.

TECHNICAL FIELD

The current subject matter relates predicting the success of anterior cruciate ligament (ACL) surgical procedures.

BACKGROUND

ACL injuries occur at a high frequency in the US with approximately 400,000 ACL reconstructions being performed each year[20]. While ACL reconstruction is commonly used to treat ACL injuries, it may not restore normal joint motion[39], or prevent premature development of post-traumatic osteoarthritis in many patients[2].

SUMMARY

New treatments for an ACL injury, which are less invasive, restore motion, and reduce patient morbidity and cartilage damage are desirable[28,36].

In some implementations, predicting the risk of graft or ligament repair failure using non-invasive magnetic resonance (MR) techniques are described.

In some implementations, the current subject matter describes a magnetic resonance imaging system that can acquire a series of imaging data sets, identify the structure of interest (e.g., the anterior cruciate ligament), record the magnetic resonance imaging values from the data set for the pixels in that structure of interest, place the values into a predetermined mathematical equation to generate a risk score. The generated score can be used to correlate with the risk of failure of the repaired ligament or graft on return to sport or other outcome measures of importance to the patient or the surgeon (e.g., see FIG. 1).

In some implementations, the magnetic resonance imaging (MRI) system can involve a 1.5 T to 11 T magnet (e.g., Siemens, Phillips, General Electric, Hatachi, Toshiba). In some implementations, the imaging can use a coil specific for the knee or a coil that can be wrapped around the knee (e.g., a flexible coil). In some implementations, the imaging sequences can include 3D Constructive Interference in Steady State (CISS) sequence, gradient multiple-echo sequences, multi-echo spin echo, multi-echo fast spin sequence, UTE-T2* mapping sequences, or any other sequence that can exhibit contrast between the ACL or graft and the surrounding tissues or fluid.

In some implementations, the structure of interest can be the anterior cruciate ligament. In some implementations, the anterior cruciate ligament can have been altered by injury or had a surgical procedure performed on it in the past or both. In some implementations, the structure of interest can be a ligament, tendon, meniscus, fat, muscle, bone cartilage, etc.

In some implementations, the magnetic resonance images can be acquired for the knee joint. In some implementations, the images can be acquired for a different joint (e.g. shoulder, ankle, hip, spine, elbow, finger, hand, foot, etc.).

In some implementations, the data acquired for the structure of interest can be divided or normalized by data acquired for a second structure, for example, cancellous bone. Other examples of the second structure can include cortical bone, fat, muscle, ligament, tendon within the body, etc.

In some implementations, a calibration can be performed using a standard of reference that is not within the knee prior to acquiring the data for the structure of interest. This can be a synthetic or natural structure that is placed into the coil at some point prior to obtaining the images of the structure of interest. This phantom can be an object approximately the size of the knee to be imaged or approximately the size of the tissue to be imaged within the knee. This can be an object approximately the size of the joint to be imaged, where the joint is a joint other than the knee. This may be a fluid, solid or semi-solid calibration instrument, where the semi-solid or fluid component may be housed in a container.

In some implementations, the images are obtained after an ACL injury. In some implementations, the images are obtained after a surgical procedure has been performed on the ACL. In some implementations, the images are obtained after the native ACL is surgically repaired, using sutures or scaffolds or other materials to repair the ligament. In some implementations the images are obtained after a bridge-enhanced ACL repair (BEAR) or similar procedure is performed. In some implementations, the images are obtained after the ACL is regenerated after injury. In some implementations, the images are obtained after the ligament is surgically reconstructed with a graft of tendon. In some implementations, the ligament is imaged after surgery and a second injury has occurred.

In some implementations, the T2* values of the structure can be calculated, mapped, and utilized in the mathematical model to predict the failure loads or to create a failure risk score or risk index (e.g., MR Strength Index or MR Strength Score).

In some implementations, the selection of the structure of interest can be performed by a person. In some implementations, the selection can be done by a semi-automated system. In yet another implementation, the selection of the structure of interest can be done using an automated system. In some implementations, the automated system that selects the structure of interest can be directly connected to the MRI acquisition software. In some implementations, the MRI data can be sent to a separate processor for analysis.

In some implementations, only the sequential images for one set of acquisition parameters can be utilized. In some implementations, the sequential images from more than one set of acquisition parameters (e.g., over different time points) can be utilized. In some implementations, only one image can be utilized. In some implementations, multiple images are utilized. In some implementations, the one image selected for use is selected using other images in the same plane. In some implementations, the one image selected for use is selected using images from a different plane.

In some implementations, the mathematical equations can have terms related to the number of pixels in the structure of interest. In some implementations, the mathematical equation can have terms related to the image data in each pixel of the structure of interest. In yet another implementation, the mathematical equation can have terms related to the average image data in the structure of interest. In some implementations, the mathematical equation can have terms related to specific regions of interest within the ligament, graft, or tendon. In some implementations, the mathematical equation can have terms related to more than one set of acquired imaging data.

In some implementations, the MR Strength Score can directly reflect the yield load, failure load and/or linear stiffness value or the yield stress, failure stress or modulus of the structure of interest. In some implementations, a combination of the above listed variable could be employed. In yet another implementation, the MR Strength Score can be generated simultaneously with the acquisition of the MR images. In some implementations, the score can be generated within 24 hours of acquisition of the MR images. In some implementations, the score can be generated more than 24 hours after acquisition of the MR images.

In some implementations, the contralateral or uninjured knee can be imaged. In some implementations, the data from uninjured knee can be incorporated into the mathematical models for failure prediction of the injured or surgical limb (e.g., see FIG. 2).

In some implementations, the sequences can include T2* relaxation time, 3D gradient multi-echo (e.g., Constructive Interference in Steady State or CISS)), T1-weighted gradient echo (e.g., Fast low angle shot (FLASH)) and proton density sequences, or any other sequence that adequately highlights the contrast between the ACL and surrounding tissues and fluids. This can include equivalent sequences between different manufacturers.

In other implementations, measurements of the ligament size can be determined via segmentation performed manually, semi-automatically, or automatically.

In some implementations, normalization of the ACL signal intensity (e.g., signal-to-noise quotient) performed by dividing the signal intensity of the ACL or graft by the signal intensity of a region of bone, posterior cruciate ligament, patellar tendon, menisci, fat, or other soft tissue structures in or about the knee.

In some implementations, T2 or T2* relaxation times can be determined using a 3D multi-echo sequence utilizing 2-12 echoes.

In some implementations, signal intensity, signal-to-noise quotient, or T2* relaxation times could be presented as mean values across the entire ACL or graft, or represented on a voxel-wise basis for analysis.

In some implementations, the mathematical models can be based on a single time point during healing or multiple time points during healing.

In some implementations, a system for automatic or semi-automatic image generation for magnetic resonance (MR) imaging can include a processor configured to execute computer-executable instructions to cause the system to define the area of the scan comprising the ACL, acquire an MR imaging data set within that area, use the area and MR imaging data in a mathematical model, present the imaging data for visual assessment, and generate a score which correlates with the risk of failure of the ACL in a human patient. In some implementations, the system is a MR image processing workstation. In yet another implementation, the system is a picture archiving and communication system (e.g., PACS). In other implementations, the calculations and analyses are performed in part on a phone or tablet. The calculations and analysis may be performed in an application for a phone or tablet. They can be performed in the application after taking a picture of the MR of the injured knee. They may be performed in the app after taking a picture of the MR of the injured knee and the contralateral knee.

In another aspect, a method is provided that includes defining a region on a scan comprising one or more of an anterior cruciate ligament (ACL) or an ACL grafts. The method can further include obtaining a magnetic resonance (MR) imaging data set within the region, and deriving, using the MR imaging data, MR parameters that characterize a size and a quality of the ACL or the ACL graft. The method can also include using the MR parameters as inputs to a predictive model, and generating, using the predictive model, a score characterizing a likelihood of failure of the ACL or ACL graft in a human patient.

One or more of the following features can be included in any feasible combination. In some embodiments, the likelihood of failure can include a future clinical outcome including failure of the ACL or ACL graft.

In some embodiment, the MR parameters can include signal intensity, signal-to-noise quotient, and/or T2* relaxation time.

In some embodiments, T2 or T2* relaxation times can be determined using a 3D multi-echo sequence utilizing 2-12 echoes.

In some embodiments, signal intensity, signal-to-noise quotient, and/or T2* relaxation times can be represented as mean values across an entire ACL or ACL graft, or represented on a voxel-wise basis.

In some embodiments, the MR parameters can include a volume of the ACL or ACL graft.

In some embodiments, the MR parameters can include a distribution of T2* values of the ACL or ACL graft.

In some embodiments, the MR imaging dataset can include a stack of MRI images.

In some embodiments, the predictive model can include terms characterized by a number of pixels in the MR imaging dataset within the defined region, terms characterized by the MR image parameters within each pixel of the defined region, terms characterized by an average in the defined region, terms characterized by specific regions of interest within a ligament, graft, or tendon or terms characterized by more than one set of acquired MR imaging parameters.

In some embodiments, the predictive model is generated, and the generating can include performing multivariable regression analyses to determine relationships between the MR imaging parameters and failure properties of the ACL or ACL graft.

In some embodiments, acquiring a magnetic resonance (MR) imaging data set can be performed using a magnetic resonance imaging (MRI) system including a 1.5T to 11T magnet.

In some embodiments, the MR imaging data set can be acquired using imaging sequences that include 3-dimensional (3D) gradient multiple-echo sequences, multi-echo spin echo, or multi-echo fast spin sequence.

In some embodiments, the predictive model can be generated by at least calculating and mapping T2* values in order to predict failure loads or to create a failure risk score.

The predictive model can be generated using preclinical T2* distributions in ACL or ACL graft and relating to failure properties.

In some embodiments, the score can characterize a yield load, a failure load and/or a linear stiffness value.

In some embodiments, the score can be proportional to yield load, failure load, and linear stiffness values of the ACL or ACL graft.

In some embodiments, the method can include determining cross-sectional area of the ACL or ACL graft, and determining length of the ACL or ACL graft.

In some embodiments, the method can include using the determined cross-sectional area and determined length as inputs to a second predictive model, and generating, using the second predictive model, a second score. The score can characterize a yield stress, a failure stress or a modulus of a structure of interest.

In some embodiments, the MR imaging data set can include MR parameters that characterizes a contrast between the ACL or ACL graft and surrounding tissues and fluids.

In some embodiments, the MR imaging data set can include T2* relaxation time, 3D gradient multi-echo, T1-weighted gradient echo, or proton density sequences.

In some embodiments, the method can include measuring ligament size using segmentation performed manually, semi-automatically, or automatically.

In some embodiments, the method can include normalizing an ACL or ACL graft signal intensity by at least dividing the signal intensity of the ACL or ACL graft by a signal intensity of a region of bone, posterior cruciate ligament, patellar tendon, menisci, fat, or other soft tissue structures in or about the knee.

In some embodiments, the predictive model can be generated using MR parameters derived from images acquired at a single time point during healing.

In some embodiments, the predictive model can be generated using MR parameters derived from images acquired at multiple time points during healing.

In some embodiments, the MR imaging dataset can include data acquired at a single time point during healing.

In some embodiments, the MR imaging dataset can include data acquired at multiple time points during healing.

In some embodiments, the method can include obtaining a second MR imaging dataset for an ACL of a contralateral knee, and deriving, using the second MR imaging dataset, second MR parameters that characterize a size and a quality of an ACL of the contralateral knee. The method can also include dividing the MR specific parameters by the second MR specific parameters for the ACL of the contralateral knee.

In some embodiments, the method can include dividing the MR imaging parameters by imaging parameters derived for a second structure.

In some embodiments, the second structure can include cancellous bone, cortical bone, fat, muscle, ligament, or tendon within the body.

In some embodiments, the signal intensity of a tissue in a contralateral knee can be used in the predictive model to standardize the score characterizing the risk of failure of the ACL or ACL graft in a human patient.

In some embodiments, the signal intensity of a tissue in the contralateral knee can be used in the predictive model to standardize the score, the score characterizing the likelihood of future clinical outcomes of the ACL or ACL graft in a human patient.

In some embodiments, the method can include obtaining a second MR imaging dataset for an ACL of a contralateral knee. The predictive model can be generated using second MR specific parameters for the ACL of the contralateral knee for failure prediction of an injured knee.

In some embodiments, the method can include administering, based on the score, a treatment protocol to the patient.

In some embodiments, the treatment protocol can include avoidance of stress on the knee for a predefined period of time.

In another aspect, a system for synthetic image generation for magnetic resonance (MR) imaging is provided. The system can include a processor configured to execute computer-executable instructions to cause the system to perform operations comprising the method described herein.

One or more of the following features can be included in any feasible combination. In some embodiments, the processor can be configured to present imaging data for visual assessment, and present the score.

In some embodiments, the system includes an MR image processing workstation or a picture archiving and communication system.

In another aspect, a method to noninvasively predict the failure risk of an anterior cruciate ligament (ACL) surgery using magnetic resonance (MR) imaging is provided. The method can include defining a region of a scan comprising an ACL or an ACL graft, acquiring MR imaging dataset within the region, obtaining MR parameters that define a size and quality of the ACL or ACL graft from the MR image dataset, obtaining second MR specific parameters for the ACL of a contralateral knee, using the MR parameters from both knees as inputs to a predictive model, and generating a score that correlates to the risk of failure of the ACL or ACL graft in a human patient.

In another aspect, a non-transitory computer program product storing instructions is provide. The instructions, when executed by at least one data processor of at least one computing system, implement a method according to any of methods described herein.

In another aspect, apparatus, systems, articles and techniques described or illustrated herein are provided.

Non-transitory computer program products (i.e., physically embodied computer program products) are also described that store instructions, which when executed by one or more data processors of one or more computing systems, cause at least one data processor to perform operations herein. Similarly, computer systems are also described that may include one or more data processors and memory coupled to the one or more data processors. The memory may temporarily or permanently store instructions that can cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims.

BRIEF DESCRIPTION OF FIGURES

FIGS. 8 b, d and f, are plots illustrating examples of actual versus predicted structural properties of the ACL based on 12-parameter ($Vol_1+Vol_4$) model;

DETAILED DESCRIPTION

A non-invasive technique (e.g., magnetic resonance imaging (MRI)) can be used to evaluate the risk of failure or the likelihood of success of ACL surgery of healing ligaments and tendons in the body. The technique can include inputting MR imaging data set (e.g., signal intensity, signal-to-noise quotient, or T2* relaxation time) of an ACL or ACL graft into a predetermined or pre-generated predictive (e.g., mathematical) model to generate a score that correlates to a risk of failure of the ACL or ACL graft.

This technique can have several advantages. For example, it can allow physicians and researchers to assess new treatment strategies, to design rehabilitation protocols tailored to the current strength of the healing ligament or tendon, to determine when a patient is ready to go back to sport and/or activities, to determine the risk of ACL or ACL graft failure, etc. MRI techniques that can include the size of the anterior cruciate ligament (ACL) or ACL graft, and an indicator of tissue quality (e.g., signal to noise quotient or T2* relaxation times) can be used to accurately predict the biomechanical properties of a healing ligament without harming any tissue, and to predict the likelihood of ACL failure upon return to sport after ACL surgery.

Figure 37:
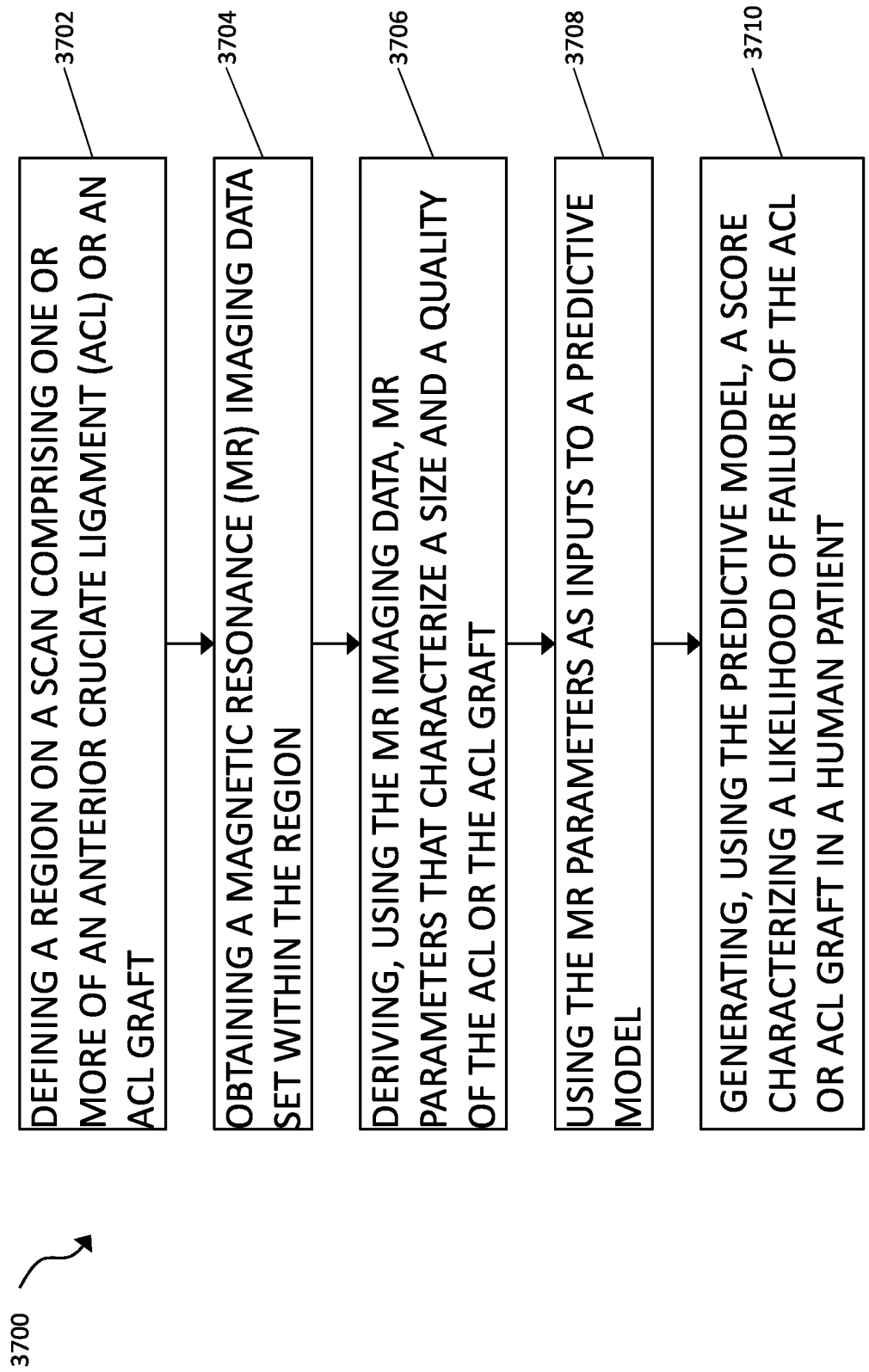
FIG. 37 is a flow diagram illustrating a method of generating a score that characterizes a likelihood of failure of an ACL or ACL graft in a human patient.

FIG. 37 shows a flow diagram 3700 illustrating a method of generating a score that characterizes a likelihood of failure of an ACL or ACL graft in a human patient.

At step 3702, the method includes defining a region on a scan comprising one or more of an anterior cruciate ligament (ACL) or an ACL graft.

The method includes obtaining a magnetic resonance (MR) imaging data set within the region, at step 3704.

At step 3706, MR parameters that characterize a size and quality of the ACL or ACL graft are derived using the MR imaging data.

At step 3708, the method includes using the MR parameters as inputs to a predictive model.

At step 3710, a score characterizing a likelihood of failure of the ACL or ACL graft in a human patient is generated using the predictive model.

In some embodiments, the likelihood of failure can include a future clinical outcome including failure of the ACL or ACL graft. As another example, the MR parameters can include signal intensity, signal-to-noise quotient, and/or T2* relaxation time. In some embodiments, T2 or T2* relaxation times can be determined using a 3D multi-echo sequence utilizing 2-12 echoes.

As another example, signal intensity, signal-to-noise quotient, and/or T2* relaxation times can be represented as mean values across an entire ACL or ACL graft, or represented on a voxel-wise basis.

In some embodiments, the MR parameters can include a volume of the ACL or ACL graft. For example, the model can user parameters that are obtained from the MR imaging data.

In some embodiments, the MR parameters can include a distribution of T2* values of the ACL or ACL graft. In some embodiments, the MR imaging dataset can include a stack of MRI images.

In some embodiments, the predictive model can include terms characterized by the number of pixels in the MR imaging dataset within the defined region, terms characterized by the MR image parameters within each pixel of the defined region, terms characterized by an average in the defined region, terms characterized by specific regions of interest within a ligament, graft, or tendon or terms characterized by more than one set of acquired MR imaging parameters. As another example, the predictive models can be generated and validated in pre-clinical animal studies. The models can then be scaled to humans. In some embodiments, the models can take two forms: 1) based on volume and signal intensity values of the ACL or ACL graft; 2) based on a distribution of T2* values across pixels comprising the ACL or ACL graft. Multivariable regression analyses can be performed to determine relationships between these two approaches and the failure properties of the ligament. Similar models can be generated to predict the yield and failure stresses and moduli given the ability to measure the cross-sectional area and length of the ACL or ACL graft, as described herein. In some example implementations, predictive models were generated and validated in pre-clinical animal studies and were then scaled to humans. These exemplary predictive models can take two forms; 1) based on the volume and signal intensity values of the ACL; 2) based on the distribution of the T2* values across the pixels comprising the ligament. Multivariable regression analyses were performed to determine the relationships between these two approaches and the failure properties of the ligament. Given that it can also be possible to measure the cross-sectional area and length of the ligament, similar models can be generated to predict the yield and failure stresses and moduli (as described below with respect to example 11).

In some embodiments, generating the predictive model can include performing multivariable regression analyses to determine relationships between the MR imaging parameters and failure properties of the ACL or ACL graft.

In some embodiments, acquiring a magnetic resonance (MR) imaging data set can be performed using a magnetic resonance imaging (MRI) system including a 1.5T to 11T magnet.

In some embodiments, the MR imaging data set can be acquired using imaging sequences that include 3-dimensional (3D) gradient multiple-echo sequences, multi-echo spin echo, or multi-echo fast spin sequence.

In some embodiments, the predictive model can be generated by at least calculating and mapping T2* values in order to predict failure loads or to create a failure risk score. The predictive model can be generated using preclinical T2* distributions in ACL or ACL graft and relating to failure properties. In this case, the predictive models can be generated using the T2* distributions in the ligament or graft from preclinical studies of relating this distribution and/or mean T2* values to the failure properties of the ligament. In some implementations, the predictive models have been generated using the T2* distributions in the ligament or graft from preclinical studies of relating this distribution and/or mean T2* values to the failure properties of the ligament.

In some embodiments, the score can characterize a yield load, a failure load and/or a linear stiffness value. As another example, the score can be proportional to yield load, failure load, and linear stiffness values of the ACL or ACL graft.

In some embodiments, the method can include determining cross-sectional area of the ACL or ACL graft, and determining length of the ACL or ACL graft.

In some embodiments, the method can include using the determined cross-sectional area and determined length as inputs to a second predictive model, and generating, using the second predictive model, a second score. The score can characterize a yield stress, a failure stress or a modulus of a structure of interest.

In some embodiments, the MR imaging data set can include MR parameters that characterizes a contrast between the ACL or ACL graft and surrounding tissues and fluids. As another example, the MR imaging data set can include T2* relaxation time, 3D gradient multi-echo, T1-weighted gradient echo, or proton density sequences.

In some embodiments, the method can include measuring ligament size using segmentation performed manually, semi-automatically, or automatically.

As another example, the method can include normalizing an ACL or ACL graft signal intensity by at least dividing the signal intensity of the ACL or ACL graft by a signal intensity of a region of bone, posterior cruciate ligament, patellar tendon, menisci, fat, or other soft tissue structures in or about the knee.

In some embodiments, the predictive model can be generated using MR parameters derived from images acquired at a single time point during healing.

In some embodiments, the predictive model can be generated using MR parameters derived from images acquired at multiple time points during healing.

In some embodiments, the MR imaging dataset can include data acquired at a single time point during healing.

In some embodiments, the MR imaging dataset can include data acquired at multiple time points during healing.

In some embodiments, the method can include obtaining a second MR imaging dataset for an ACL of a contralateral knee, and deriving, using the second MR imaging dataset, second MR parameters that characterize a size and a quality of an ACL of the contralateral knee. The method can also include dividing the MR specific parameters by the second MR specific parameters for the ACL of the contralateral knee.

In some embodiments, the method can include dividing the MR imaging parameters by imaging parameters derived for a second structure.

In some embodiments, the second structure can include cancellous bone, cortical bone, fat, muscle, ligament, or tendon within the body.

In some embodiments, the signal intensity of a tissue in a contralateral knee can be used in the predictive model to standardize the score characterizing the risk of failure of the ACL or ACL graft in a human patient.

In some embodiments, the signal intensity of a tissue in the contralateral knee can be used in the predictive model to standardize the score, the score characterizing the likelihood of future clinical outcomes of the ACL or ACL graft in a human patient.

In some embodiments, the method can include obtaining a second MR imaging dataset for an ACL of a contralateral knee. The predictive model can be generated using second MR specific parameters for the ACL of the contralateral knee for failure prediction of an injured knee.

In some embodiments, the method can include administering, based on the score, a treatment protocol to the patient.

In some embodiments, the treatment protocol can include avoidance of stress on the knee for a predefined period of time.

In developing treatment options, a method to non-invasively assess the biomechanical properties of a healing ACL, graft or even other ligaments and tendons can improve the efficiency of in vivo pre-clinical trials, and speed up the cycle time of clinical trials of these technologies.

A non-invasive strategy to evaluate ligament and graft healing can improve the ability of physicians to advise patients of the risk of ligament or graft failure on return to sport and/or activity, much as an x-ray does for a broken bone. A direct measure of biomechanical properties of the healing ligament or graft can enhance scientific evaluation. However, while pulling the healing ligament apart to measure its mechanical properties is possible in pre-clinical studies, it may not be feasible for patients. Therefore, a non-invasive measure of predicting the strength of the graft or repair can be useful in advising patients as to their risk of ligament or graft failure if they chose to return to high level activities or sport. Other non-invasive measures of leg strength and patient reported outcomes are currently used to advise patients on the timing of return to sport. However, none of these measures have been found to accurately predict subsequent graft or ligament repair failure[15] or other patient outcomes. MRI can serve as a clinically relevant, non-invasive and sensitive means to predict and/or inform failure risk for patients.

MRI based techniques can be used to predict clinical outcomes for patients (e.g., correlation with hop tests and patient reported outcomes at 5 years after surgery)[5]. However, some MRI techniques may not correlate with knee laxity, and may fail to determine the risk of graft failure. Clinical studies have shown that some MRI based techniques may not predict the failure load of the ACL or ACL graft for humans[6]. Waltz et al (2014) taught that caution should be used when evaluating a failed ACL graft with MRI as it may be unreliable and inconsistent[41]. Chang et al (2014) also taught that no MRI findings had statistically significant relationships with physical exam findings for patients with MRIs performed three months after injury, and only non-visualization of the ACL was related to the Lachman test results[11]. Likewise, Howell et al (1991) have determined that clinical outcome may not be predicted based on the MRI signal of the graft[18]. While some other investigators have used graft signal intensity to evaluate the maturation and vascularity of ACL grafts of humans[10,14,16,19,21,22,25,34,35,38,40] none of them have used MR derived parameters to predict graft success or failure or to gauge when a person can return to sport or activity. It can be desirable to noninvasively and prospectively predict the risk of graft or ligament repair failure for patients who have had ACL surgery.

Figure 7:
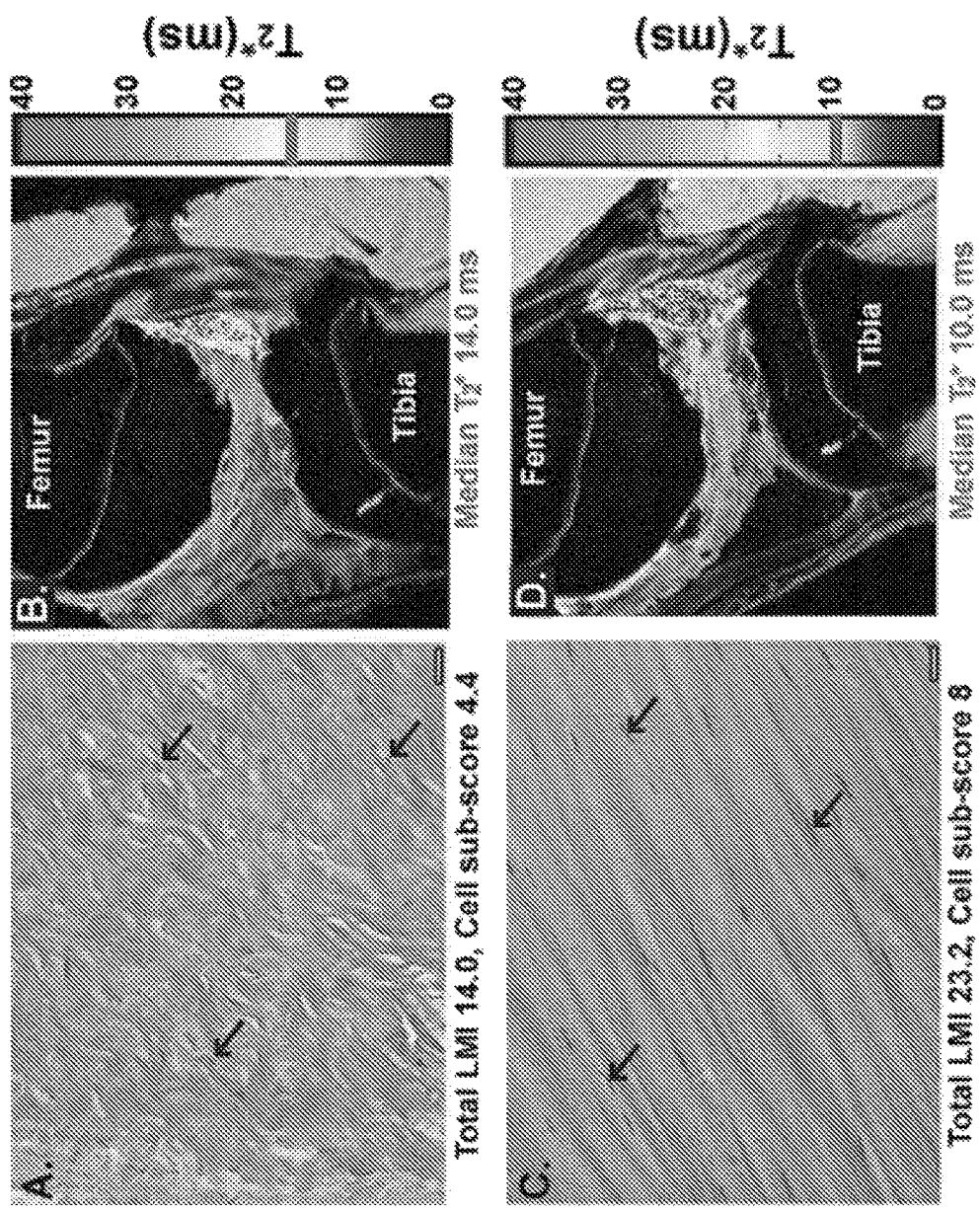
FIG. 7A is an image illustrating an example of ligament histology with a low total ligament score.
FIG. 7B is a T2* ligament map associated with FIG. 7A.
FIG. 7C is an image that illustrates an example of ligament histology with a high total ligament score.
FIG. 7D is a T2* ligament map associated with FIG. 7C.

Signal intensity (either graded or using the signal-to-noise quotient) can be used to assess graft maturation and/or vascularity following ACL reconstruction surgery in vivo[1,4,18,19,26,30,31,33,37]. These methods have not been validated, have been limited to a single 2-D slice within the graft, may be magnet and sequence dependent, and may not predict risk of ligament or graft failure. Signal intensity, or gray scale value, can represent the quality of ligament tissue[18,30,31,33,37], but this has not been validated in humans Using the rabbit model, Anderson et al. noted that the signal intensity of an ACL graft may be related to the tensile strength[3], while Weiler et al. reported significant correlations between signal intensity to the failure load, linear stiffness and tensile strength of the ACL graft in sheep[42]. However, three-dimensional imaging or combined signal intensity with any size specification measure (e.g., volume) have not been used to predict graft properties or failure in human patients. Prediction of the yield load, failure load and linear stiffness in animal models can be improved by considering both the volume of the graft and the signal intensity of the graft[7,17] (e.g., see FIGS. 3 & 4). Prediction models can correlate with histological changes observed in the pig ligament[9] (e.g., see FIG. 7). However, animal models may not directly correlate with findings in human patients[32]. So recent studies were performed in patients to demonstrate that the procedure can predict outcome and risk for graft failure.

In some implementations, volume and normalized signal intensity approach can establish which ACL surgical patients are at higher risk for ligament or graft failure (e.g., see FIGS. 9, 10, 11 & 12). For example, in a cohort of 19 patients, who underwent a surgical ACL repair procedure (Bridge-enhanced ACL repair), failure load using the MR-based algorithm from images acquired of the surgical knee after 6 months of healing could be predicted. This point in time was selected as it is generally the amount of time required before allowing patients to return to sport[27]. It was found that the average predicted failure load could be 690 N. However, there was one patient with a predicted failure load of 212 N (e.g., see FIG. 10). While this patient passed all other return to sport criteria, the repaired ligament failed within days of returning back to soccer. Likewise, a similar data set for patients who underwent ACL reconstruction can be constructed (e.g., see FIG. 12). No failures have been noted to date in this cohort.

Figure 5:
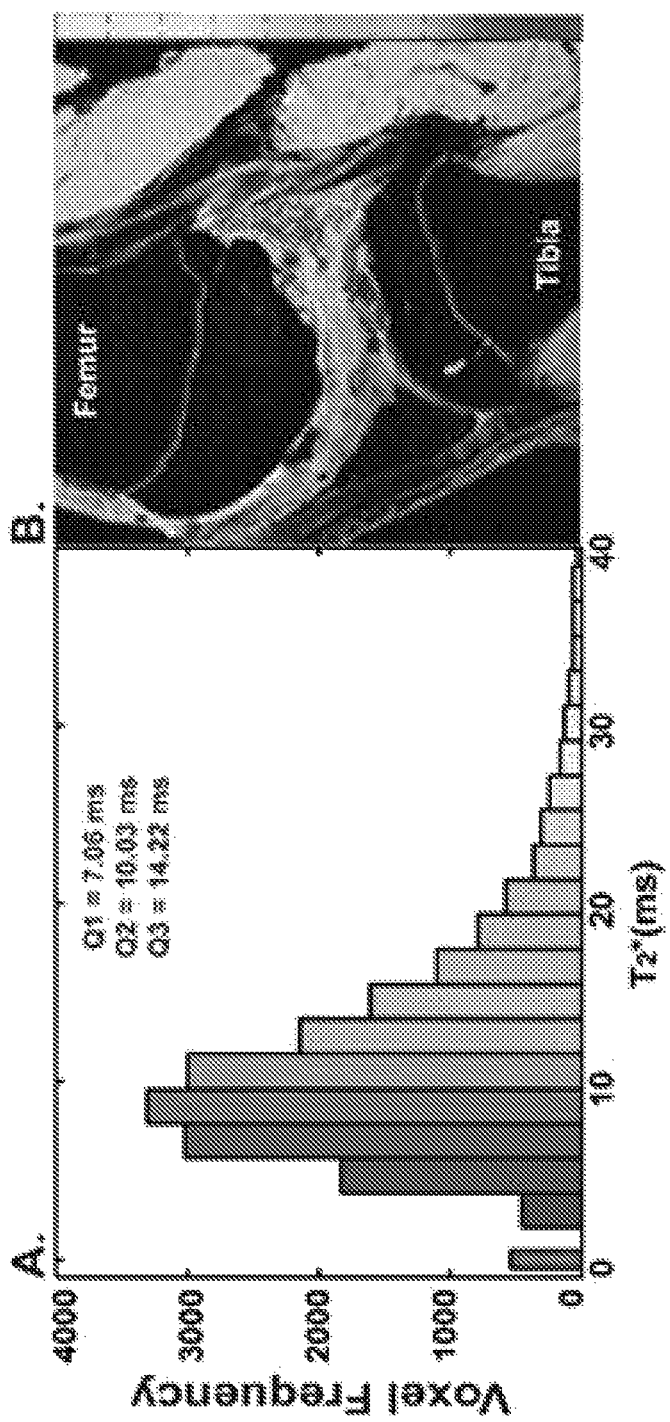
FIG. 5A is a histogram that illustrates an example of T2* distribution of a healing ACL.
FIG. 5B is an image illustrating a T2* ligament specific map of FIG. 5A.
Figure 6:
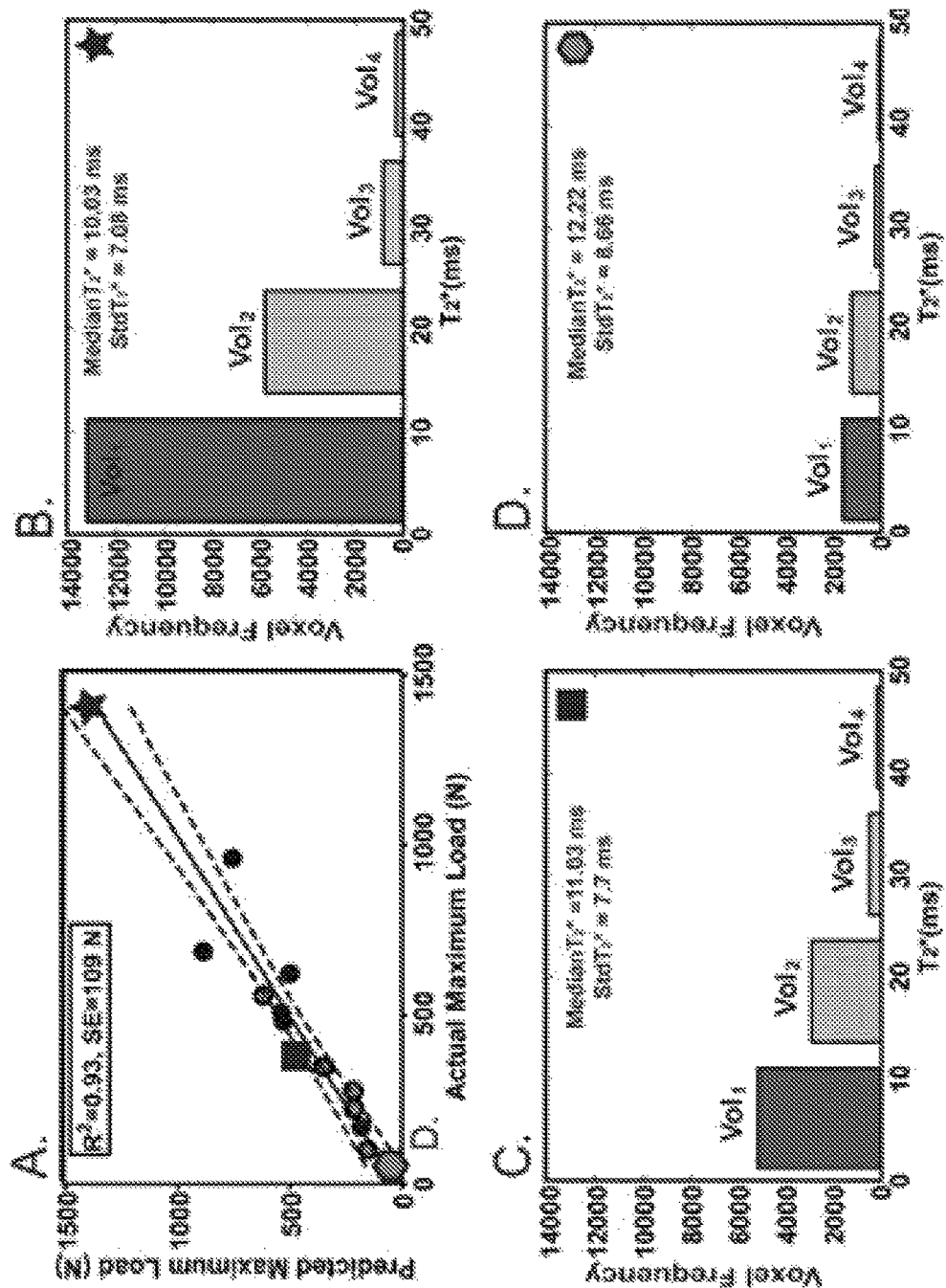
FIG. 6A is a plot illustrating an example of actual versus predicted maximum load for T2* model.
FIG. 6B is a histogram of the highest load ligament.
FIG. 6C is a histogram of the median load ligament.
FIG. 6D is a histogram of the lowest load ligament.

Signal intensity may not be fundamental properties of a tissue. However, it can be influenced by sequence parameters and the hardware used to acquire the images[13]. Thus, a calibration method may be required to use these techniques in different scanners or with different coils. Relaxation time variables, such as T2 and T2*, have been used to correlate with the level of tissue organization[12,24], can be well suited for imaging highly organized collagenous structures[12,23,24,43], and can be less sensitive to imaging parameters[13]. T2* mapping is another MR based method that can allow for signal intensity standardization and normalization (e.g., see FIGS. 5 and 6)[13]. In some implementations, different methods can be used to predict ACL or ACL graft failure (e.g., normalized signal intensity combined with ligament volume[5,7], voxel-wise mapping of the T2* relaxation time[8,9], etc.).

Figure 1:
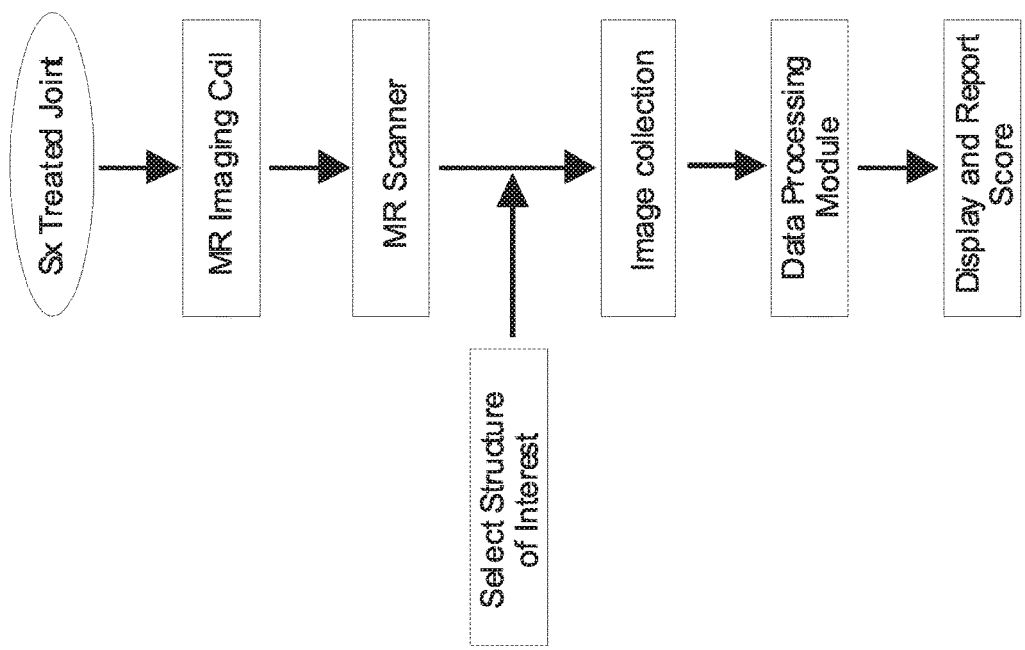
FIG. 1 is a flowchart illustrating an exemplary method of generating MRI strength score that can be predictive of failure for an ACL surgical procedure using the surgical knee.

FIG. 1 illustrates an exemplary method of generating MRI strength score that can be predictive of failure for an ACL surgical procedure using the surgical knee.

Figure 2:
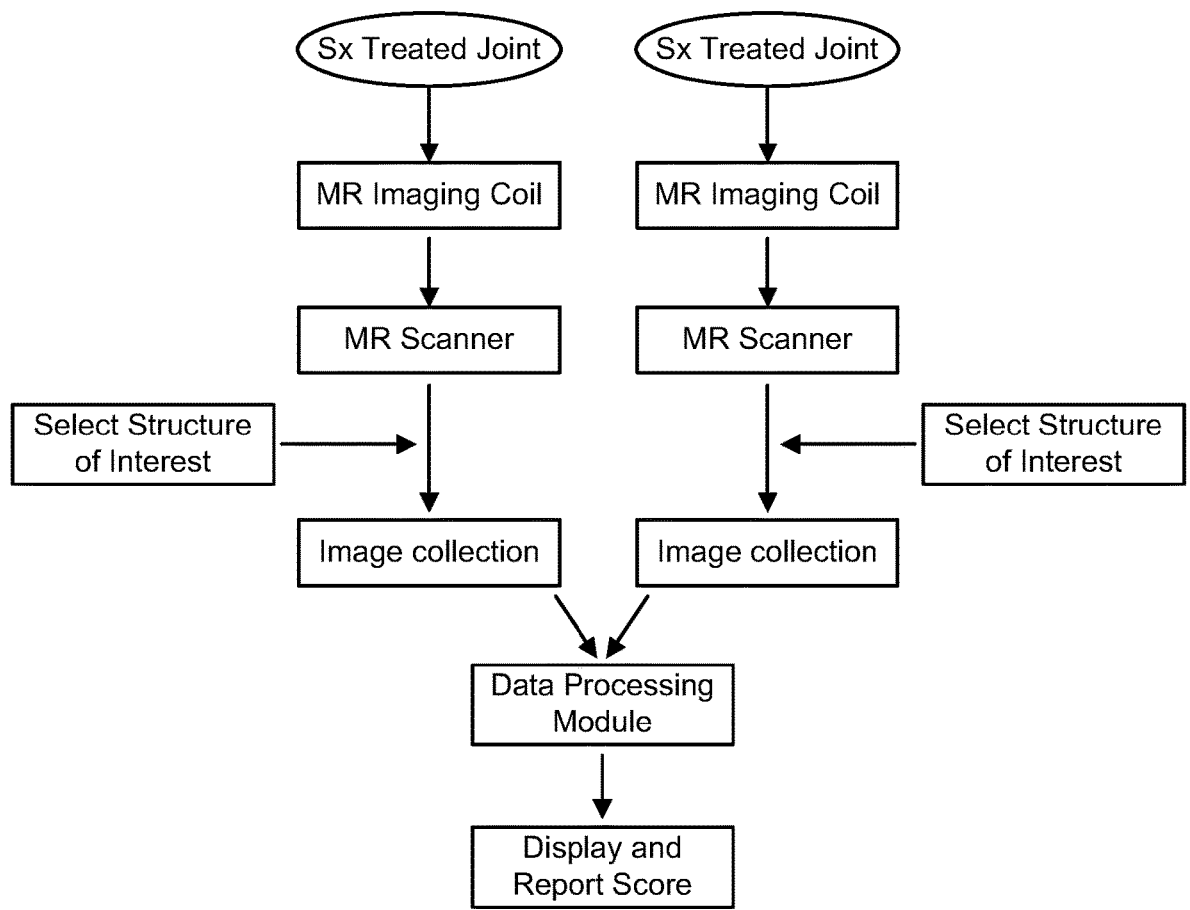
FIG. 2 is a flowchart illustrating an exemplary method of generating MRI strength score that can be predictive of failure for an ACL surgical procedure using the surgical knee and the contralateral uninjured knee.

FIG. 2 illustrates an exemplary method of generating MRI strength score that can be predictive of failure for an ACL surgical procedure using the surgical knee and the contralateral uninjured knee.

Figure 3:
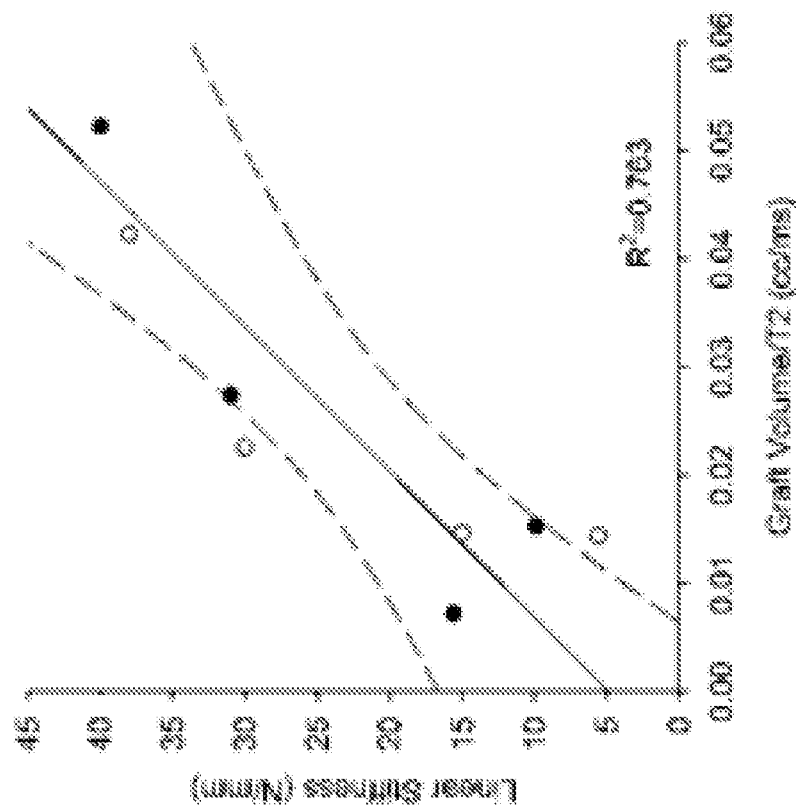
FIG. 3 is a plot illustrating an example of dependence of graft failure load and linear stiffness on graft volume normalized by T2 relaxation time.
Figure 3:
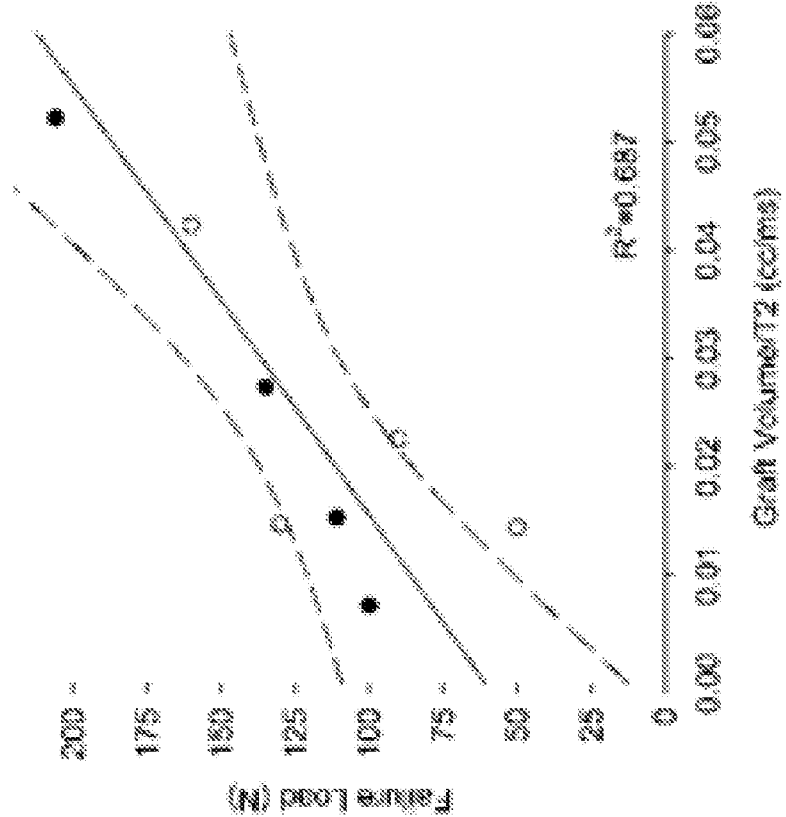

FIG. 3 illustrates an example of dependence of graft failure load and linear stiffness on graft volume normalized by T2 relaxation time. Graft failure load and linear stiffness after 6 weeks of ACL graft healing can correlate with graft volume normalized by the T2 relaxation time in the porcine model. The open circles represent data points from the animals treated with the collagen sponge and the closed circles represent data points from those animals treated with a collagen-platelet composite. Dashed lines mark the 95% confidence intervals[17].

Figure 4:
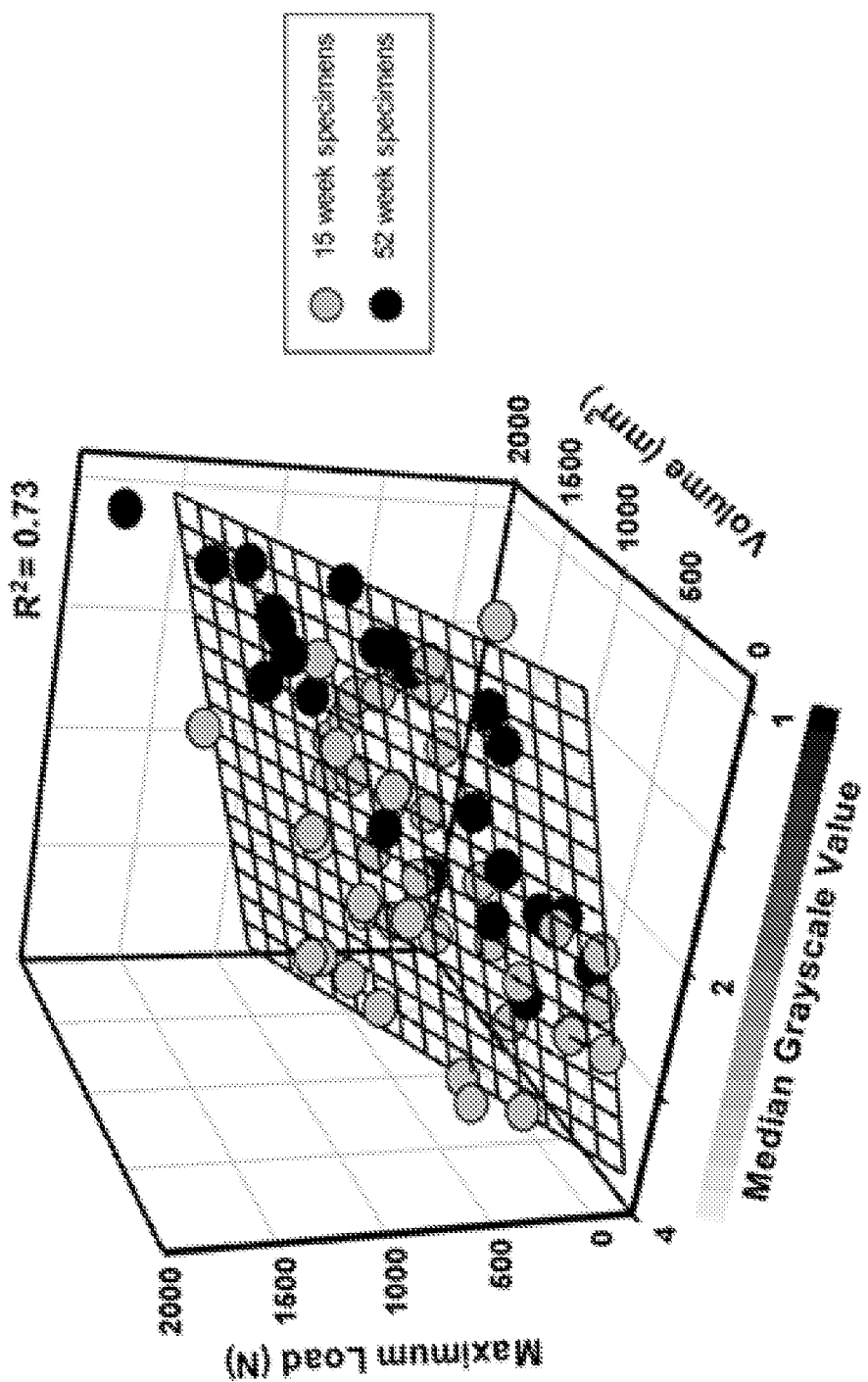
FIG. 4 is a plot illustrating an example of dependence of maximum failure loads of surgically treated ACLs at 15 and 52 weeks on median grayscale and volume used to create the multiple regression model for the porcine model.

FIG. 4 illustrates an example of dependence of maximum failure loads of surgically treated ACLs at 15 and 52 weeks on median grayscale and volume used to create the multiple regression models for the porcine model. The 15-week and 52-week specimens are noted with gray and black symbols, respectively. Plots for yield load and linear stiffness can follow similar patterns. The standard errors of the prediction planes for the maximum load, yield load and linear stiffness were 216N, 196N, and 36N respectively.

FIGS. 5A and 5B illustrate an example of ligament histogram. Example ligament histogram showing (A) the distribution of T2* with associated 1st quartile (Q1), median (Q2) and 3rd quartile (Q3) statistics, (B) the T2* ligament specific map. Prediction equations of the yield load, failure load, and stiffness can be developed[8].

FIGS. 6A-D illustrate examples of actual versus predicted maximum load and related histograms for T2* model. FIG. 6A shows actual versus predicted maximum load calculated using the linear combination of Vol1, Vol2, Vol3 and Vol4. Gray shapes represent transected ligaments while black shapes represent repaired ligaments. The highest (star, B), median (square, C) and lowest (hexagon, D) maximum load ligaments and their corresponding histogram profile are also represented. The analyses have been run using 4, 8 and 16 bins. However, 4 bins can be sufficient to represent the distribution effects and how they change with degree of healing[8].

FIGS. 7A-D illustrate examples of images of ligament histology and T2* ligament maps. A decrease in the median T2* values of healing ACLs can correspond to improved histological features of the tissue. FIG. 7A illustrates an example ligament histology image with a low total ligament score and cell sub-score (total LMI 14.0, cell sub-score 4.4). Arrows indicate that cell nuclei may not be clearly aligned with longitudinal axis of collagen fibers. Also, the collagen fibers lack a distinct longitudinal axis. FIG. 7B illustrates associated T2* ligament map for the low total LMI histology image overlaid on the original DICOM image. FIG. 7C illustrates an example ligament histology image with a high total ligament score and cell sub-score (total LMI 23.2, cell sub-score 8). Arrows indicate that cell nuclei can be aligned with longitudinal axis of collagen fibers. FIG. 7D illustrates the associated T2* ligament map for the high total LMI histology image overlaid on the original DICOM image. Histology images can be H&E stained at 40× magnification, scale bar indicates 20 mm. The color bars in the T2* maps represent the range of T2* values in the ligament with the median T2* value for the ligament highlighted in red. The MR images are a sagittal view of the femoral notch with the femur at the top of the image and the tibia at the bottom. For the MR images shown TE½7.36 ms[9].

Figure 8:
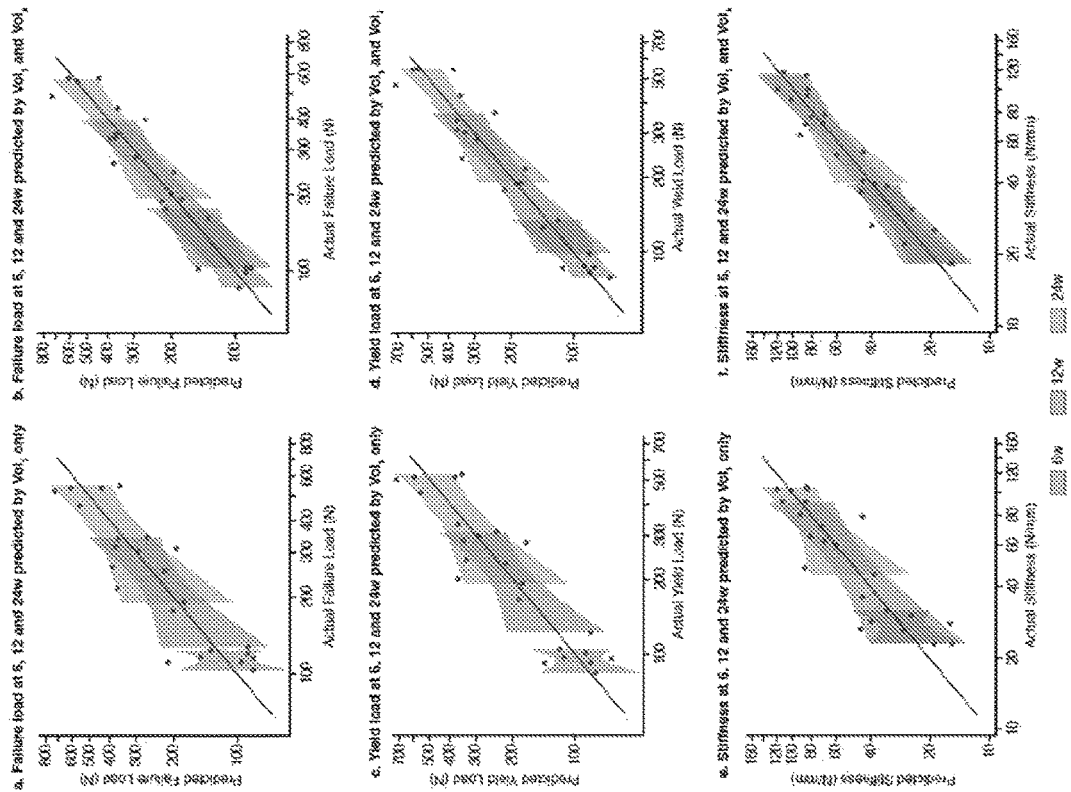
FIGS. 8 a, c and e, are plots illustrating examples of actual versus predicted structural properties based on 6-parameter $Vol_1$ model.

FIGS. 8a-f illustrates examples of actual versus predicted structural properties based on 6-parameter $Vol_1$ model (plots 8a, 8b and 8c) and 12-parameter ($Vol_1+Vol_4$) model. FIGS. 8a, c, and e illustrate actual versus predicted structural properties based on the 6-parameter $Vol_1$ only model. FIGS. 8b, d, and f illustrate actual versus predicted structural properties based on the 12-paramater ($Vol_1+Vol_4$) model. Slope=1 (solid line) for all models. The shaded regions encompass the 95% confidence intervals of the estimated slope for each time point, which is color-coded according to the legend at the bottom. Each circle corresponds to one animal.

Figure 9:
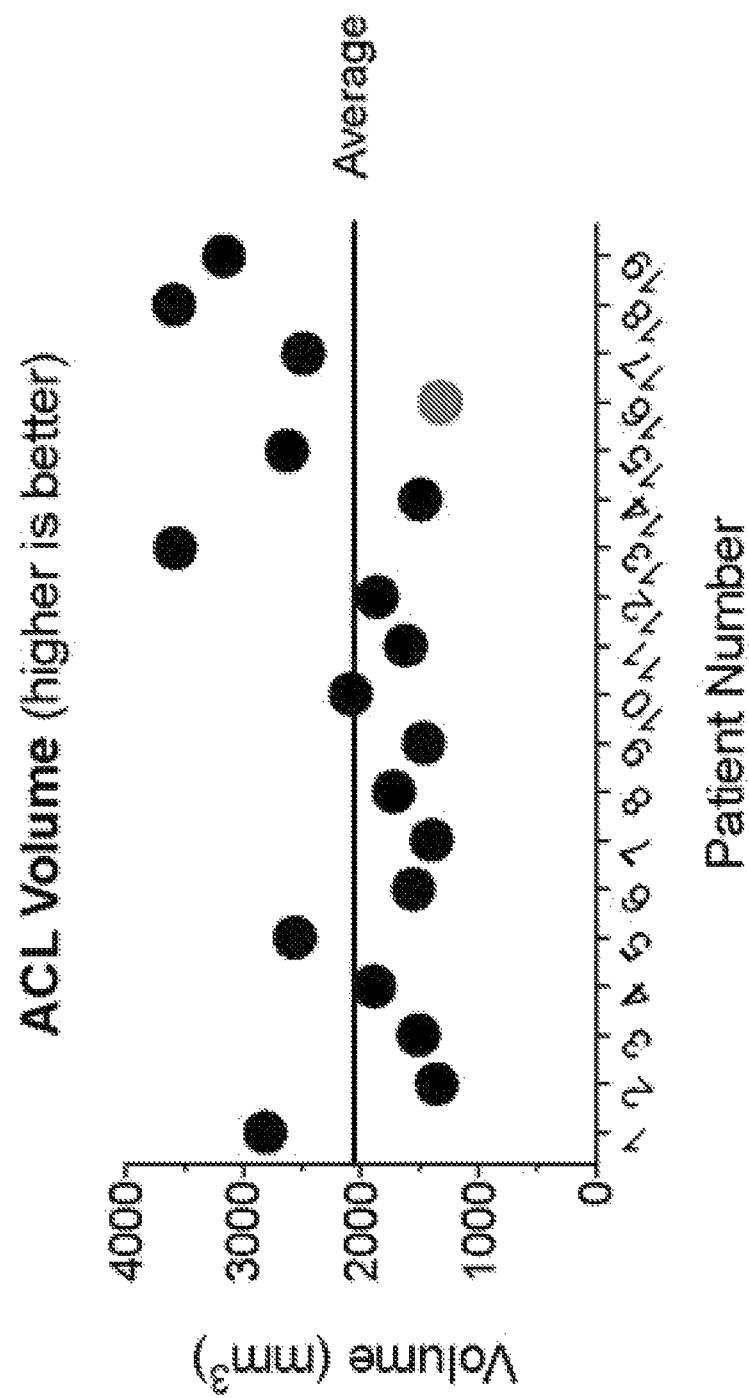
FIG. 9 is a graph illustrating an example of a plot of ACL volumes in human patients at six months after ACL surgery.

FIG. 9 illustrates an example of a plot of ACL volumes at six months after ACL surgery of 19 patients. The volume measurements can imply a reasonable wide range of values seen in patients undergoing identical ACL surgical procedures.

Figure 10:
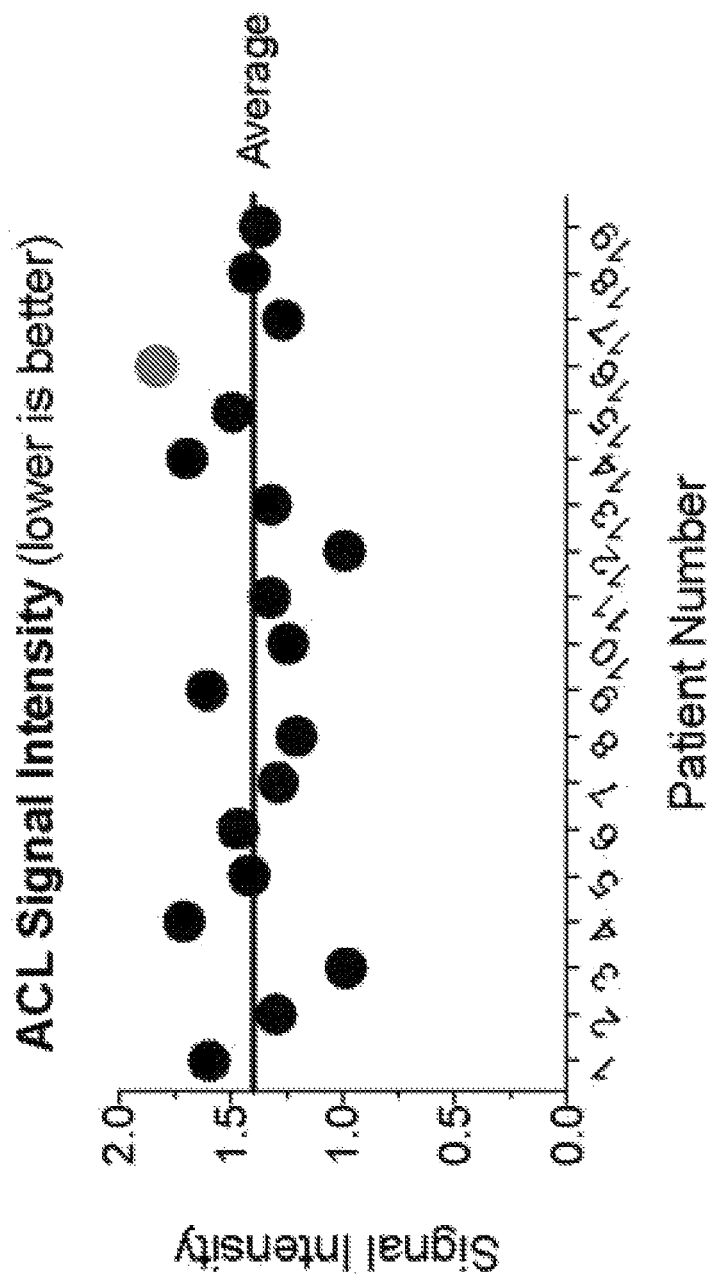
FIG. 10 is a graph illustrating an example of a plot of normalized signal intensity values acquired using MR imaging in human patients at six months after ACL surgery.

FIG. 10 illustrates an example of a plot of normalized signal intensity values acquired using MR imaging at six months after ACL surgery. This can imply the reasonable wide range of values seen in patients undergoing identical ACL procedures.

Figure 11:
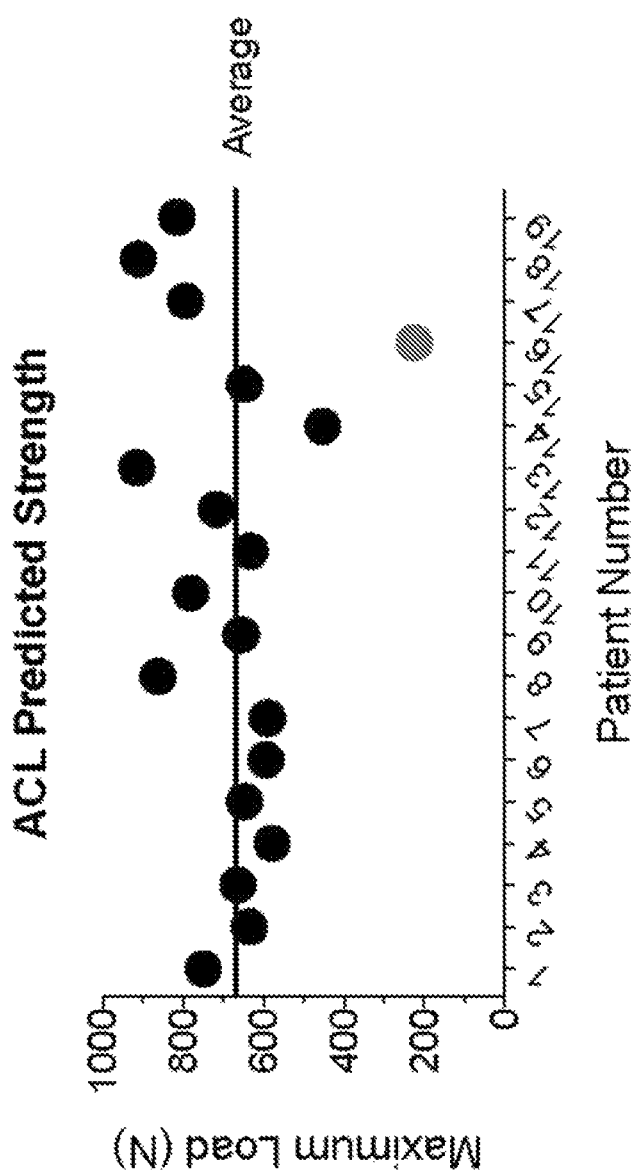
FIG. 11 is a graph illustrating an example of a plot of generated risk score (MRI strength score) for 19 patients acquired using MR imaging at the six-month post-operative visit.

FIG. 11 illustrates an example of a plot of generated risk score (MRI strength score) for 19 patients acquired using MR imaging at the six-month post-operative visit. This data can be obtained from the MRI images acquired at the six-month post-operative visit, prior to their return to sport. The red dot denotes the patient whose ligament repair failed immediately after return to sport. When comparing to the volume data (normalized by length; see FIG. 9) and the signal intensity data (normalized to bone; see FIG. 10) the patient that failed exhibited a lower than average volume and a higher than average signal intensity. No other patients have had a graft or repair failure on their initial return to sport.

Figure 12:
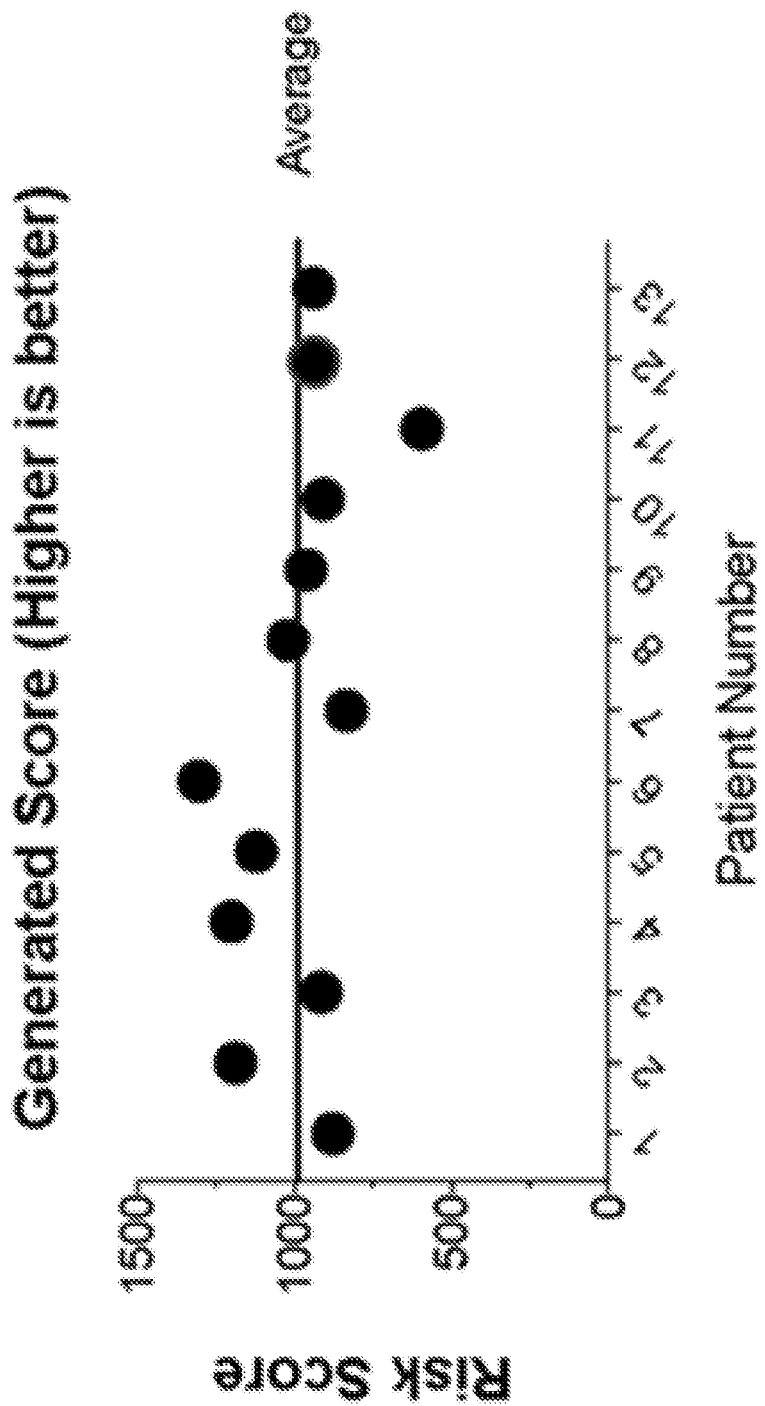
FIG. 12 is a graph illustrating an example of a plot of generated risk scores for 13 patients who underwent ACL reconstruction surgery.

FIG. 12 illustrates Generated risk scores (MRI Strength Scores) for 13 patients who underwent ACL reconstruction surgery. These data were obtained from the MRI images acquired at the six-month post-operative visit, prior to their return to sport. There have been no graft failures in this cohort at this time.

Example 1

In some implementations, ACL graft volume and T2 relaxation time can be used to predict the structural properties of the ACL graft[17]. For example, magnetic resonance imaging (MRI) can be used to non-invasively predict the strength of an ACL graft after ACL reconstruction. The volume and T2 relaxation parameters of the ACL graft measured with MR imaging can predict the graft structural properties. Nine goats underwent ACL reconstruction using a patellar tendon autograft augmented with a collagen scaffold or collagen-platelet composite. After 6 weeks of healing, the reconstructed knees were retrieved and imaged on a 3T scanner. AP laxity was measured prior to dissecting out the femur-graft-tibia constructs, which were then tested to tensile failure to determine the structural properties. Regression analysis (e.g., see FIG. 3) indicated a statistically significant relationship between the graft volume and the failure load ($R^2=0.502$; p=0.049). When graft volume was normalized to the T2 relaxation time, the relationship was improved ($R^2=0.687$; p=0.011). There was also a significant correlation between the graft volume and the linear stiffness ($R^2=0.847$; p<0.001), which remained significant with T2 normalization ($R^2=0.764$; p=0.002). These results demonstrated that MRI volumetric measures when used in conjunction with the graft T2 properties can be useful for predicting the biomechanical properties of ACL grafts non-invasively.

Example 2

In some implementations, in-situ Non-Invasive T2*-weighted MRI derived Parameters can determine Ex Vivo structural Properties of an ACL Reconstruction or Bio-enhanced Primary Repair in a Porcine Model[7]. MR derived measures of graft volume and signal intensity can predict structural properties of a healing ACL or ACL graft after 15 weeks and 52 weeks of healing. The current data were gathered from two experiments evaluating ACL reconstruction and repair techniques. In the first experiment, pigs underwent unilateral ACL transection and received: 1) ACL reconstruction, 2) ACL reconstruction with collagen platelet composite (CPC), or 3) no treatment. The surgical legs were harvested following 15 weeks of healing. In the second experiment, pigs underwent ACL transection and received: 1) ACL reconstruction, 2) ACL reconstruction with CPC, 3) bio-enhanced ACL primary repair with CPC, or 4) no treatment. The surgical legs were harvested after 52 weeks. The harvested knees were imaged using a T2* weighted 3D-CISS sequence. Each ligament was segmented from the scans, and the intra-articular volume and the median grayscale values were determined. Mechanical testing was performed to establish the ligament structural properties. Volume can predict the structural properties (maximum load, yield load, linear stiffness) of the ligaments and grafts ($R^2$=0.56, 0.56, 0.49; p≤0.001). Likewise, the median grayscale values can predict the structural properties of the ligaments and grafts ($R^2$=0.42, 0.37, 0.40; p<0.001). However, the R2 values are not high enough to serve as adequate predictors for medical decision making on their own. However, the combination of these two parameters in a multiple regression model can further improved the prediction of the graft strength, and can be closer to the values needed for clinical decision making ($R^2$=0.73, 0.72, 0.68; p≤0.001) (see FIGS. 4 and 29). Volume and signal intensity from high resolution T2* weighted MRI images can predict structural properties of the healing ligament or graft in a porcine model. This study provided a step in the development of non-invasive method to predict the structural properties of the healing ACL graft or repair. This technique may prove beneficial as a surrogate outcome measure in pre-clinical animal and clinical studies.

Example 3

In some implementations, T2* MR Relaxometry and Ligament Volume are Associated with the Structural Properties of the Healing ACL[8].

One of the goals was to develop a non-invasive MR method to predict the structural properties of a healing ACL using volume and T2* relaxation time. Surgical ACL transection followed by no treatment (i.e., natural healing) or bio-enhanced ACL repair was performed in a porcine model. After 52 weeks of healing, high-resolution MR images of the ACL tissue were collected. From these images, ligament volumes and T2* maps could be established. The structural properties of the ligaments were determined via tensile testing. Using the T2* histogram profile, each ligament voxel was binned based on its T2* value into four discrete tissue subvolumes defined by specific T2* intervals. The linear combination of the ligament sub-volumes binned by T2* value significantly predicted maximum load, yield load, and linear stiffness ($R^2$=0.92, 0.82, 0.88; p<0.001) (FIGS. 5, 6, 31, and 32). $R^2$ values greater than 0.80 are desired for clinical decision making. The T2* technique offers a highly predictive methodology that can be used to non-invasively assess ligament healing.

Example 4

In some implementations, T2* relaxometry and volume can predict Semi-Quantitative Histological Scoring of an ACL Bridge-enhanced Primary repair in a Porcine Model[9]. MRI variables, such as T2* and volume, can predict the biomechanical properties of the healing ligament. The relation between MR variables and histology measures of the healing ACL is unknown. T2* and volume can predict the histological scoring of a healing ACL. Yucatan minipigs underwent ACL transection and received bio-enhanced ACL repair or no treatment. The surgical legs were imaged using a high resolution 2-echo sequence so that the volume and median T2* values could be measured. The ACLs were then sectioned and histologically evaluated using the advanced Ligament Maturity Index (LMI) which can provide a semi-quantitative measure of collagen density, collagen orientation, cellularity and vascularity.

The T2* of the healing ligaments could significantly predict the Total LMI score as well as the Cell, Collagen and Vessel sub-scores; R2=0.78, 0.67, 0.65, and 0.60, respectively (p≤0.001). The ligament volume could also predict the Total LMI score, Cell and Collagen sub-scores; R2=0.39, 0.33, 0.37, and 0.60, respectively (p≤0.001). A lower ligament T2* or a higher volume was associated with higher histological scores of the healing ligaments (see FIG. 7). The two variables when included together would provide the best prediction of ligament integrity. This study demonstrates that the variables of interest are related to the collagen formation which is known to be responsible for providing the ligament strength.

Example 5

In some implementations, MRI volume and signal intensity of the ACL graft can predict clinical, functional and patient oriented outcome measures Following ACL Reconstructions. Clinical, functional and patient-oriented outcomes are commonly used to evaluate the efficacy of treatments following ACL injury. However, these evaluation techniques do not directly measure the biomechanical changes that occur with healing. One of the goals is to determine if the MR image-derived parameters of graft volume and SI correlate with commonly used clinical (anteroposterior (AP) knee laxity), functional (1-leg hop) and patient-oriented outcome measures (Knee Osteoarthritis Outcome Score) in patients 3- and 5-years after ACL reconstruction. Using a subset of participants enrolled in an ongoing ACL reconstruction clinical trial, AP knee laxity, 1-legged hop test, and KOOS were assessed at 3- and 5-year follow-up. 3-D T1-weighted MR images were collected at each visit. Both the volume and median SI of the healing graft were determined and used as predictors in a multiple regression linear model to predict the traditional outcome measures. Graft volume combined with median SI in a multiple linear regression model could predict 1-legged hop test at both the 3-year and 5-year follow-up visits (R2=0.40, p=0.008 and R2=0.62, p=0.003, respectively). Similar results were found with 5-year follow up for the KOOS quality of life (R2=0.49, p=0.012), sport function (R2=0.37, p=0.048), pain (R2=0.46, p=0.017) and symptoms (R2=0.45, p=0.021) sub-scores, though these variables were not significant at 3 years. The multiple linear regression model for AP knee laxity at 5-year follow-up approached significance (R2=0.36, p=0.088). The MR parameters (volume and median SI) used to predict ex vivo biomechanical properties of the graft in an animal model can have the ability to predict clinical or in vivo outcome measures in patients at 3- and 5-year follow-up. While these R2 values were not sufficiently high for clinical decision making, most likely because the commonly used clinical measures may not directly measure the function of the ligament but of the whole joint, these data indicate that these two MR variables (graft volume and signal intensity) are related to some of the commonly used clinical outcome measures.

Example 6

In some implementations, the combination of tissue collagen quantity and quality estimated from MR T2* relaxometry can predict time-specific structural properties of healing ACL following ACL repair (Beveridge J E, Machan J T, Walsh E G, Kiapour A M, Karamchedu N P, Chin K E, Proffen B L, Sieker J T, Murray M M, Fleming B C: Magnetic resonance measurements of tissue quantity and quality using T2* relaxometry predict temporal changes in the biomechanical properties of the healing ACL. Journal of Orthopaedic Research, 2017 Dec. 11, doi: 10.1002/jor.23830). Magnetic resonance T2* is an imaging property that can reflects collagen organization, with lower T2* relaxation times corresponding to more aligned fibers. This study developed a T2* relaxometry-based statistical model to predict the structural properties of the healing anterior cruciate ligament (ACL) over a 24-week healing period in a preclinical model of ACL repair. Two hypotheses were tested: (1) that a multiple linear regression model based on both short and long T2* relaxation times would outperform a competing model based on short T2* relaxation times only; and (2) that an optimized prediction model would be capable of predicting ACL structural properties between 6 and 24 weeks post-repair. ACLs were imaged in 24 minipigs (8/group) at either 6, 12, or 24 weeks after ACL repair. The structural properties of the ACLs were determined from tensile tests. Two multiple linear regression models were fitted to the data. Model predictions were compared to the measured values using both models to test the second hypothesis. The multiple linear regression model that was based on both short and long T2* relaxation times outperformed the model based on the shortest relaxation times only, and predicted structural properties at all healing times investigated (see FIG. 8). The results suggest that MR T2* relaxation times that reflect the amounts of organized and disorganized collagen can predict the structural properties of healing ACLs accurately. Our time-specific, T2*-based prediction model may allow us to estimate the structural properties of ACL repairs in vivo longitudinally.

Example 7

In some implementations, MR predictive models can be used to evaluate the integrity and to predict ACL failure following surgery (Unpublished data). A 10-patient cohort study designed to demonstrate the safety of a new "Bridge-enhanced" ACL repair procedure (enrollment completed) 29 and a 100 patient randomized control trial comparing the Bridge-enhanced ACL repair procedure to ACL reconstruction with a tendon graft (enrollment is underway) are currently active. One of the outcome measures for both of these trials is the predicted failure load of the healing ligament. Failure loads, as well as yield loads and linear stiffness values, were predicted by our mathematical model using the normalized signal intensity and volume of the ligament obtained from MRI. Patients having a lower predicted failure load of the ACL can be at greater risk for ligament failure when they return to sport. To date, 19 patients with a complete ACL tear underwent surgical repair of the ACL using a bioactive scaffold to stimulate ligament healing. Ten study subjects (the cohort study) underwent MR imaging at 3, 6 and 12 months post-operatively, and 9 subjects from the randomized control trial underwent MR imaging at 6 months post-operatively. A detailed description of the Bridge-enhanced ACL repair technique has been previously reported[29]. All MR images of the surgically treated knees were obtained on a 3T Siemens scanner using a 15 channel Siemens knee coil. A T2* weighted 3D-CISS sequence was selected as this sequence produces high contrast between the soft tissues and the joint fluid, which can optimize the boundaries of the ligament or graft for manual segmentation from the image stack. Using commercially available software (Mimics Software, Materialise, Ann Arbor, Mich.), the surgically treated ligaments were manually segmented from the MR image stacks in both the coronal and sagittal planes. Three-dimensional surface models and grayscale volumes were created from the segmented images on a voxel by voxel basis. Intra-articular volumes and median grayscale values of the ACL were determined. The median grayscale values of the ligaments were normalized to the grayscale value of femoral cortical bone to account for inter-scan variability. The volume of the ligament was normalized to its length so that the predictive models, which were originally developed using the pig could be scaled to the size of the human. The predictive models, which were based on the normalized volumes and signal intensities, were used to determine the failure load of the graft. Since the predictive models were developed using the pig, these models had to be scaled for use in the human based on the length of the ligament. The term "MRI Strength Score" was used as the reported outcome measure to assess risk of failure, which can be based on the scaled failure load. Of the nineteen patients who underwent the Bridge-Enhanced ACL repair procedure, one patient had a recurrent ACL failure upon returning to sport after 6 months. The predicted MRI Strength Score from the MRI model of the repaired ACL was less than half the mean value of the other patients (see FIG. 11). The signal intensity for this patient was greater than average (see FIG. 10) while the volume was less than average (see FIG. 9). It should be noted that this patient met all return to sport criteria based on functional performance. These data demonstrate that the MR based predictive method can identify a patient at risk for graft failure or a patient that is ready to return to sport. This study is ongoing and we are continuing to enroll patients to increase the sample size to determine the relationships between graft failure and our MR-based predictive parameters.

Example 8

To date there are 13 patients that underwent ACL reconstruction who are now out to 6 months post-op in the human repair study described above (Section 7). The ACL reconstruction procedures were performed using a hamstring tendon graft. The same set of outcome measures was performed on all patients. All of the MR imaging and post processing of those images were performed as described for the Bridge-enhanced ACL repair procedures described above. The predicted failure loads were determined and a risk score was calculated. These scores are presented in FIG. 12. This study is underway and at this time, there have been no graft failures when these patients returned to sport as would be expected based on the findings thus far.

Example 9

Figure 35:
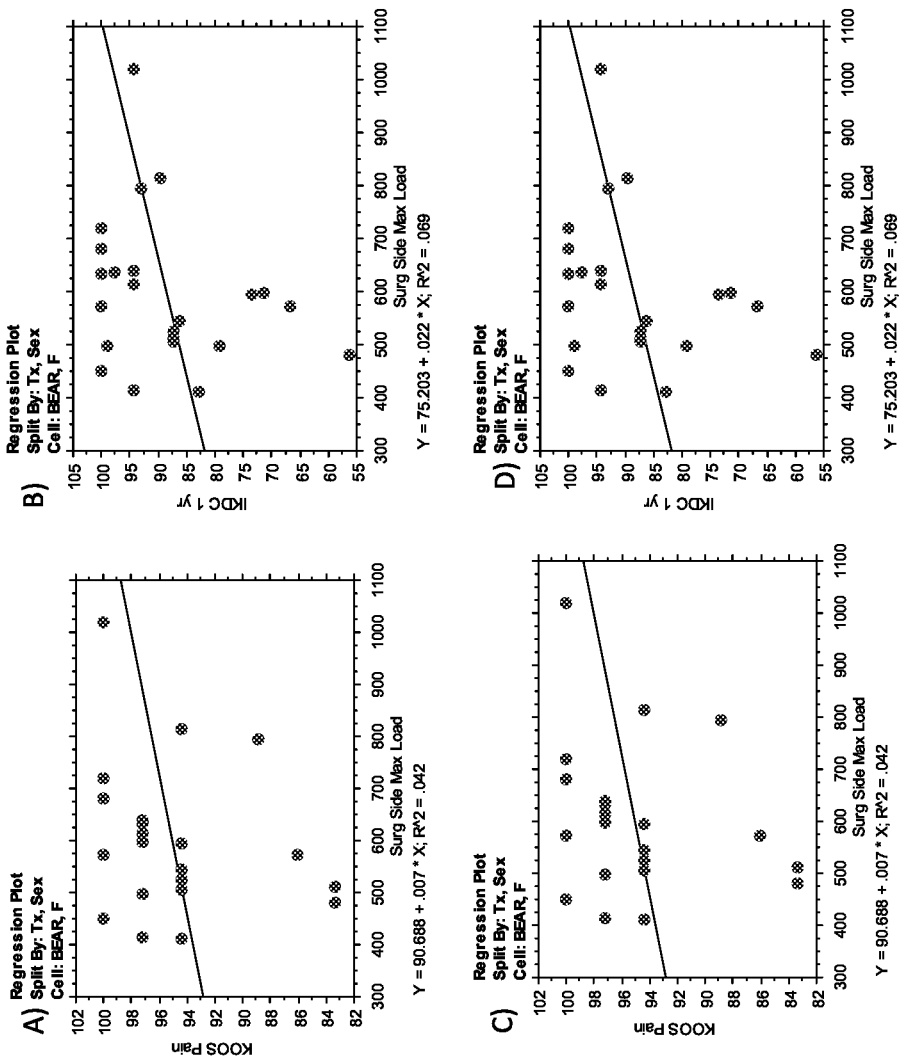
FIG. 35 is a set of plots showing knee injury and osteoarthritis outcome scores (KOOS) (35A, 35C) and international knee document committee (IKDC) scores (35B, 35D) for patients that underwent either ACL reconstruction with a hamstring autograft or bone-patellar tendon bone-autograft or a bridge-enhanced ACL repair (BEAR® procedure).

In some implementations, MR predictive models can be used to predict future outcomes of ACL surgery, including ACL reconstruction and bridge-enhanced ACL repair. In some implementations, the calculations used to predict outcomes of surgery may be different in males and females and in patients undergoing ACL repair as opposed to ACL reconstruction. In one trial, one hundred subjects underwent either ACL reconstruction with a hamstring autograft or bone-patellar tendon bone-autograft or a bridge-enhanced ACL repair (BEAR® procedure). MR images were collected at six months after surgery on both the knee that had surgery and the contralateral knee. The predicted maximum loads, determined using an equation that utilized signal intensity and volume of the healing or reconstructed ligaments, were predictive of multiple patient reported outcomes for the subjects, including KOOS Pain, Sports, Knee Related Quality of Life subscores, and the International Knee Documentation Committee score at 1 year after surgery. This was true for patients who had had the BEAR procedure performed as well as those undergoing ACL reconstruction with autograft (noted as HS in the graphs pertaining to those subjects). This was true in both men and women. These plots are illustrated in FIG. 35.

Example 10

Figure 36:
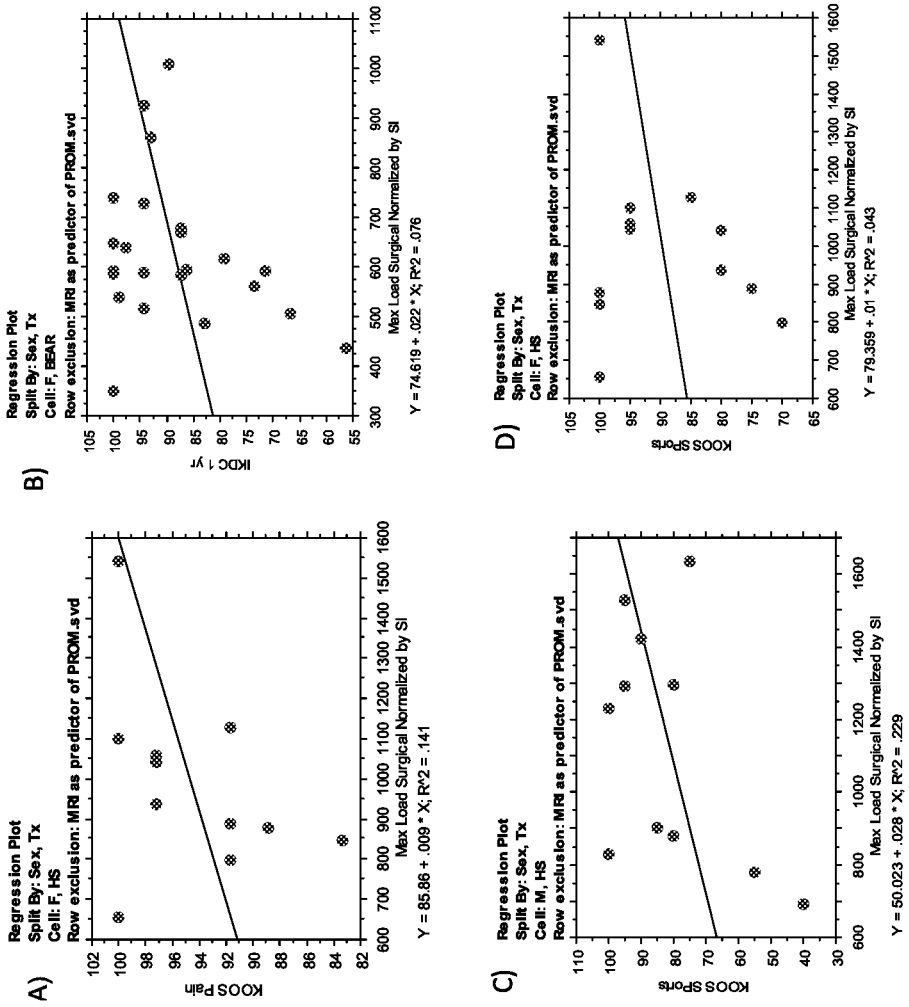
FIG. 36 is another set of plots showing KOOS (36A, 36C, 36D) and IKDC scores (35B) for patients that underwent either ACL reconstruction with a hamstring autograft or bone-patellar tendon bone-autograft or a bridge-enhanced ACL repair (BEAR® procedure).

In some implementations, MR predictive models that utilize a calibration from an object outside of the joint that has been injured or undergone surgery to standardize across magnets can be used to predict future outcomes of ACL surgery, including outcomes after ACL reconstruction and bridge-enhanced ACL repair. In some implementations, the calculations used to predict outcomes of surgery may be different in males and females and in patients undergoing ACL repair as opposed to ACL reconstruction. In one trial, seventy subjects underwent either ACL reconstruction with a hamstring autograft or bone-patellar tendon bone-autograft or a bridge-enhanced ACL repair (BEAR® procedure). MR images were collected at six months after surgery on both the knee that had surgery and the contralateral knee. The signal intensity of the normal ACL was used as a calibration measure. This calibration measure was used to standardize the values for the ACL in the surgical knee to minimize variation due to coil, magnet, etc. We found using the contralateral ACL as an external calibration for the signal intensity on the scan on each individual magnet resulted in a calculation factor that resulted in an MRI score at six months that was predictive of multiple patient reported outcomes, including IKDC score at 1 year, KOOS pain, ADL, Sports and KRQOL subscores for patients undergoing both ACL reconstruction and repair using bridge-enhanced ACL repair (BEAR) techniques. These plots are presented in FIG. 36.

Examples 1-10 References

1. Adams D J, Brosche K M, Lewis J L. Effect of specimen thickness on fracture toughness of bovine patellar cartilage. *J Biomech Engin.* 2003; 125:927-929.
2. Ajuied A, Wong F, Smith C, et al. Anterior cruciate ligament injury and radiologic progression of knee osteoarthritis: A systematic review and meta-analysis. *Am J Sports Med.* 2014; 42:2242-2252.
3. Anderson K, Seneviratne A M, Izawa K, Atkinson B L, Potter H G, Rodeo S A. Augmentation of tendon healing in an intraarticular bone tunnel with use of a bone growth factor. *Am J Sports Med.* 2001; 29:689-698.
4. Arai Y, Hara K, Takahashi T, et al. Evaluation of the vascular status of autogenous hamstring tendon grafts after anterior cruciate ligament reconstruction in humans using magnetic resonance angiography. *Knee Surg Sports Traumatol Arthrosc.* 2008; 16:342-347.
5. Biercevicz A M, Akelman M R, Fadale P D, et al. MRI volume and signal intensity of ACL graft predict clinical, functional, and patient-oriented outcome measures after ACL reconstruction. *Am J Sports Med.* 2015; 43:693-699.
6. Biercevicz A M, Akelman M R, Rubin L E, Walsh E G, Merck D, Fleming B C. The uncertainty of predicting intact anterior cruciate ligament degeneration in terms of structural properties using T relaxometry in a human cadaveric model. *J Biomech.* 2015; 48:1188-1192.
7. Biercevicz A M, Miranda D L, Machan J T, Murray M M, Fleming B C. In situ, noninvasive, T2*-weighted MRI-derived parameters predict ex vivo structural properties of an anterior cruciate ligament reconstruction or bioenhanced primary repair in a porcine model. *Am J Sports Med.* 2013; 41:560-566.
8. Biercevicz A M, Murray M M, Walsh E G, Miranda D L, Machan J T, Fleming B C. T2* MR relaxometry and ligament volume are associated with the structural properties of the healing ACL. *J Orthop Res.* 2014; 32:492-499.
9. Biercevicz A M, Proffen B L, Murray M M, Walsh E G, Fleming B C. T* relaxometry and volume predict semiquantitative histological scoring of an ACL bridge-enhanced primary repair in a porcine model. *J Orthop Res.* 2015; 33:1180-1187.
10. Buda R, Di Caprio F, Giuriati L, Luciani D, Busacca M, Giannini S Partial ACL tears augmented with distally inserted hamstring tendons and over-the-top fixation: an MRI evaluation. *Knee.* 2008; 15:111-116.
11. Chang M J, Chang C B, Choi J Y, Je M S, Kim T K. Can magnetic resonance imaging findings predict the degree of knee joint laxity in patients undergoing anterior cruciate ligament reconstruction? *BMC Musculoskelet Disord.* 2014; 15:214.
12. Chavhan G B, Babyn P S, Thomas B, Shroff M M, Haacke E M. Principles, techniques, and applications of T2*-based MR imaging and its special applications. *Radiographics.* 2009; 29:1433-1449.
13. Deoni S C, Williams S C, Jezzard P, Suckling J, Murphy D G, Jones D K. Standardized structural magnetic resonance imaging in multicentre studies using quantitative T1 and T2 imaging at 1.5 T. *Neuroimage.* 2008; 40:662-671.
14. Djian P, Christel P, Roger B, Witvoet J. Roentgenographic and magnetic resonance imaging of anterior cruciate reconstruction using a patellar tendon graft—correlations with physical findings. *Knee Surg Sports Traumatol Arthrosc.* 1994; 2:207-213.
15. Feller J, Webster K E. Return to sport following anterior cruciate ligament reconstruction. *Int Orthop.* 2013; 37:285-290.
16. Figueroa D, Mclean P, Calvo R, et al. Magnetic resonance imaging evaluation of the integration and maturation of semitendinosus-gracilis graft in anterior cruciate ligament reconstruction using autologous platelet concentrate. *Arthroscopy.* 2010; 26:1318-1325.
17. Fleming B C, Vajapeyam S, Connolly S A, Magarian E M, Murray M M. The use of magnetic resonance imaging to predict ACL graft structural properties. *J Biomech.* 2011; 44:2843-2846.
18. Howell S M, Clark J A, Blasier R D. Serial magnetic resonance imaging of hamstring anterior cruciate ligament autografts during the first year of implantation. A preliminary study. *Am J Sports Med.* 1991; 19:42-47.
19. Howell S M, Knox K E, Farley T E, Taylor M A. Revascularization of a human anterior cruciate ligament graft during the first two years of implantation. *Am J Sports Med.* 1995; 23:42-49.
20. Junkin D M, Johnson D L, Fu F H, et al. Knee Ligament Injuries. In: Kibler W B, ed. *Orthopaedic Knowledge*

*Update* 4: *Sports Medicine*. Rosemont: American Academy of Orthopaedic Surgeons; 2009:135-153.
21. Kanamiya T, Hara M, Naito M. Magnetic resonance evaluation of remodeling process in patellar tendon graft. *Clin Orthop Relat Res.* 2004:202-206.
22. Kiekara T, Jarvela T, Huhtala H, Moisala A S, Suomalainen P, Paakkala A. Tunnel communication and increased graft signal intensity on magnetic resonance imaging of double-bundle anterior cruciate ligament reconstruction. *Arthroscopy.* 2014; 30:1595-1601.
23. Koff M F, Shah P, Pownder S, et al. Correlation of meniscal T2* with multiphoton microscopy, and change of articular cartilage T2 in an ovine model of meniscal repair. *Osteoarthritis Cartilage.* 2013; 21:1083-1091.
24. Krasnosselskaia L V, Fullerton G D, Dodd S J, Cameron I L. Water in tendon: orientational analysis of the free induction decay. *Magn Reson Med.* 2005; 54:280-288.
25. Ma Y, Murawski C D, Rahnemai-Azar A A, Maldjian C, Lynch A D, Fu F H. Graft maturity of the reconstructed anterior cruciate ligament 6 months postoperatively: a magnetic resonance imaging evaluation of quadriceps tendon with bone block and hamstring tendon autografts. *Knee Surg Sports Traumatol Arthrosc.* 2015; 23:661-668.
26. McFarland E G, Morrey B F, An K-N, Wood M B. The relationship of vascularity and water content to tensile strength in a patellar tendon replacement of the anterior cruciate in dogs. *Am J Sports Med.* 1986; 14:436-448.
27. Morris R C, Hulstyn M J, Fleming B C, Owens B D, Fadale P D. Return to Play Following Anterior Cruciate Ligament Reconstruction. *Clin Sports Med.* 2016; 35:655-668.
28. Murray M M. Current status and potential of primary ACL repair. *Clin Sports Med.* 2009; 28:51-61.
29. Murray M M, Flutie B M, Kalish L A, et al. The bridge-enhanced anterior cruciate ligament repair (BEAR) procedure: An early feasibility cohort study. *Orthop J Sports Med.* 2016; 4:2325967116672176.
30. Ntoulia A, Papadopoulou F, Ristanis S, Argyropoulou M, Georgoulis A D. Revascularization process of the bone-patellar tendon-bone autograft evaluated by contrast-enhanced magnetic resonance imaging 6 and 12 months after anterior cruciate ligament reconstruction. *Am J Sports Med.* 2011; 39:1478-1486.
31. Orrego M, Larrain C, Rosales J, et al. Effects of platelet concentrate and a bone plug on the healing of hamstring tendons in a bone tunnel. *Arthroscopy.* 2008; 24:1373-1380.
32. Proffen B L, McElfresh M, Fleming B C, Murray M M. A comparative anatomical study of the human knee and six animal species. *Knee.* 2012; 19:469-476.
33. Radice F, Yanez R, Gutierrez V, Rosales J, Pinedo M, Coda S. Comparison of magnetic resonance imaging findings in anterior cruciate ligament grafts with and without autologous platelet-derived growth factors. *Arthroscopy.* 2010; 26:50-57.
34. Ruiter S J, Brouwer R W, Meys T W, Slump C H, van Raay J J. MRI signal intensity of anterior cruciate ligament graft after transtibial versus anteromedial portal technique (TRANSIG): design of a randomized controlled clinical trial. *BMC Musculoskelet Disord.* 2016; 17:334.
35. Saupe N, White L M, Chiavaras M M, et al. Anterior cruciate ligament reconstruction grafts: MR imaging features at long-term follow-up—correlation with functional and clinical evaluation. *Radiology.* 2008; 249:581-590.
36. Steiner M E, Murray M M, Rodeo S A. Strategies to improve anterior cruciate ligament healing and graft placement. *Am J Sports Med.* 2008; 36:176-189.
37. Stockle U, Hoffmann R, Schwedke J, et al. Anterior cruciate ligament reconstruction: the diagnostic value of MRI. *Int Orthop.* 1998; 22:288-292.
38. Tanaka Y, Yonetani Y, Shiozaki Y, et al. MRI analysis of single-, double-, and triple-bundle anterior cruciate ligament grafts. *Knee Surg Sports Traumatol Arthrosc.* 2014; 22:1541-1548.
39. Tashman S, Kolowich P, Collon D, Anderson K, Anderst W. Dynamic function of the ACL-reconstructed knee during running. *Clin Orthop Relat Res.* 2007; 454:66-73.
40. Valenti Azcarate A, Lamo-Espinosa J, Aquerreta Beola J D, Hernandez Gonzalez M, Mora Gasque G, Valenti Nin J R. Comparison between two different platelet-rich plasma preparations and control applied during anterior cruciate ligament reconstruction. Is there any evidence to support their use? *Injury.* 2014; 45 Suppl 4:S36-41.
41. Waltz R A, Solomon D J, Provencher M T. A Radiographic Assessment of Failed Anterior Cruciate Ligament Reconstruction: Can Magnetic Resonance Imaging Predict Graft Integrity? *Am J Sports Med.* 2014; 42:1652-1660.
42. Weiler A, Peters G, Maurer J, Unterhauser F N, Sudkamp N P. Biomechanical properties and vascularity of an anterior cruciate ligament graft can be predicted by contrast-enhanced magnetic resonance imaging—A two-year study in sheep. *Am J Sports Med.* 2001; 29:751-761.
43. Williams A, Qian Y, Golla S, Chu C R. UTE-T2* mapping detects sub-clinical meniscus injury after anterior cruciate ligament tear. *Osteoarthritis Cartilage.* 2012; 20:486-494.
44. Beveridge J E, Machan J T, Walsh E G, Kiapour A M, Karamchedu N P, Chin K E, Proffen B L, Sieker J T, Murray M M, Fleming B C: Magnetic resonance measurements of tissue quantity and quality using T2* relaxometry predict temporal changes in the biomechanical properties of the healing ACL. Journal of Orthopaedic Research, 2017 Dec. 11, doi: 10.1002/jor.23830

Example 11—Cartilage Damage is Related to ACL Stiffness in a Porcine Model of ACL Repair There is a wide-held belief that residual joint laxity contributes to structural joint damage following surgical repair of the anterior cruciate ligament (ACL).[1,2] In some cases, linear stiffness of the healing ACL can be variable within the first 6 months after surgical repair.[3] Because the ACL functions to constrain joint motion, ACL stiffness can increase over time, and an inverse relationship between cartilage damage and ACL stiffness may not be present at either 6 or 12 weeks of healing. In some cases, an inverse relationship between cartilage damage and ACL stiffness can emerge after 24 weeks of healing.

Methods:

Twenty-four 15±1 month-old (12 castrated males, 12 females) Yucatan minipigs were randomized to receive primary suture repair with (n=12; 6 female) or without (n=12; 6 female) a scaffold to enhance healing after ACL transection.[4] The two procedures were implemented to create a greater spread in the data. Animals were then randomly allocated to one of three groups (n=8 per group with an equal number of suture repairs vs. enhanced repairs and males/females in each group) based on post-operative healing duration of 6, 12, or 24 weeks (w). Following the allotted healing period, animals were euthanized and both hind limbs were disarticulated and kept frozen until mechanical testing was performed. All animal procedures were approved by the Institutional Animal Care and Use Committee. Once all 24 animals had completed the protocol, the hind limbs were thawed and then dissected leaving only the femur-ACL-tibial complex intact. A proximal end of the femur and a distal end of the tibia were potted, mounted in a custom frame, and tensile tested to failure with a servohydraulic material testing system at a rate of 20 mm/min to generate load-displacement data. Linear stiffness (N/mm) was calculated from the load-displacement data. Six weight-bearing regions of the tibiofemoral stifle cartilage were graded from 0 (no damage) to 4 (exposed bone >10%).[4] Scores were then summed within the surgical and contralateral knees, and the contralateral scores were subtracted from the surgical scores. The maximum possible cartilage damage score was 24. A generalized linear mixed model comparing the least squares differences between the time points with Holm adjustments for multiple comparisons were used to test for differences in ACL stiffness over time. Linear regression was used to determine the relationship between cartilage damage and ACL stiffness.

Results

Figure 13:
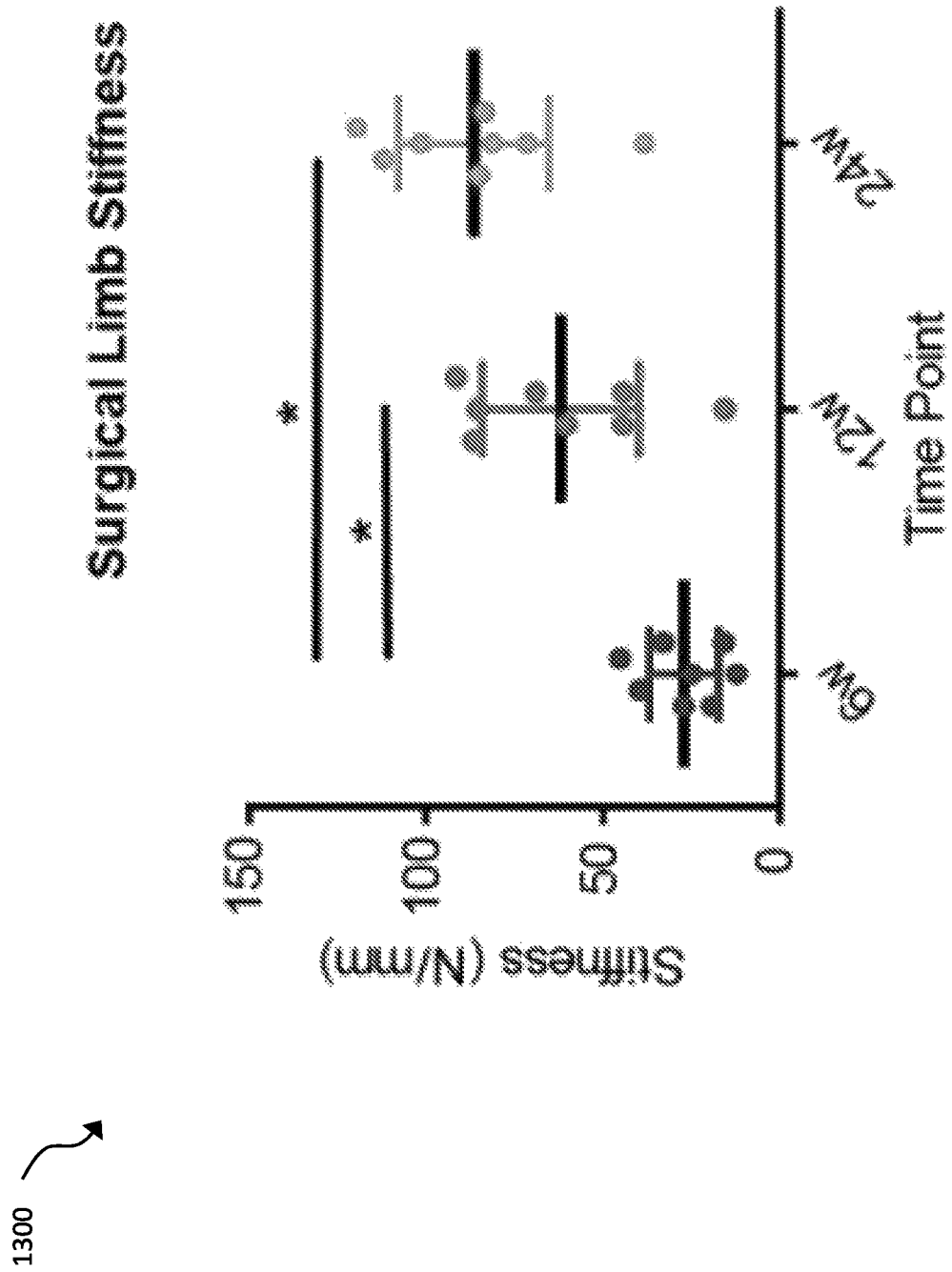
FIG. 13 is a plot of ACL linear stiffness for three groups of animal subjects, which were grouped by post-operative healing durations of 6, 12, and 24 weeks after ACL repair to demonstrate how the MR predicted stiffness can be related to future arthritis risk.
Figure 14:
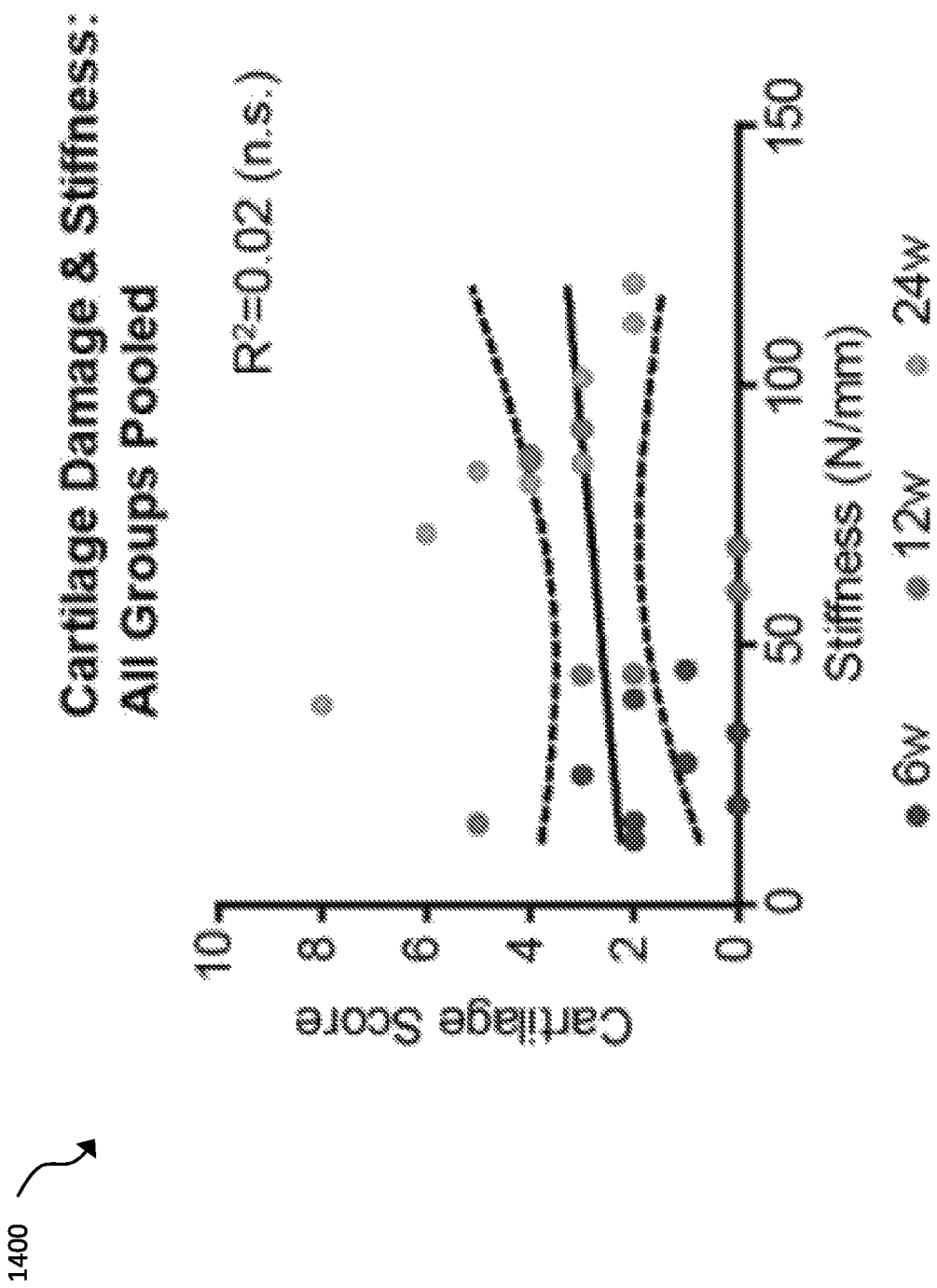
FIG. 14 is a plot of cartilage score vs. stiffness (N/mm) for the three groups of animal subjects.
Figure 15:
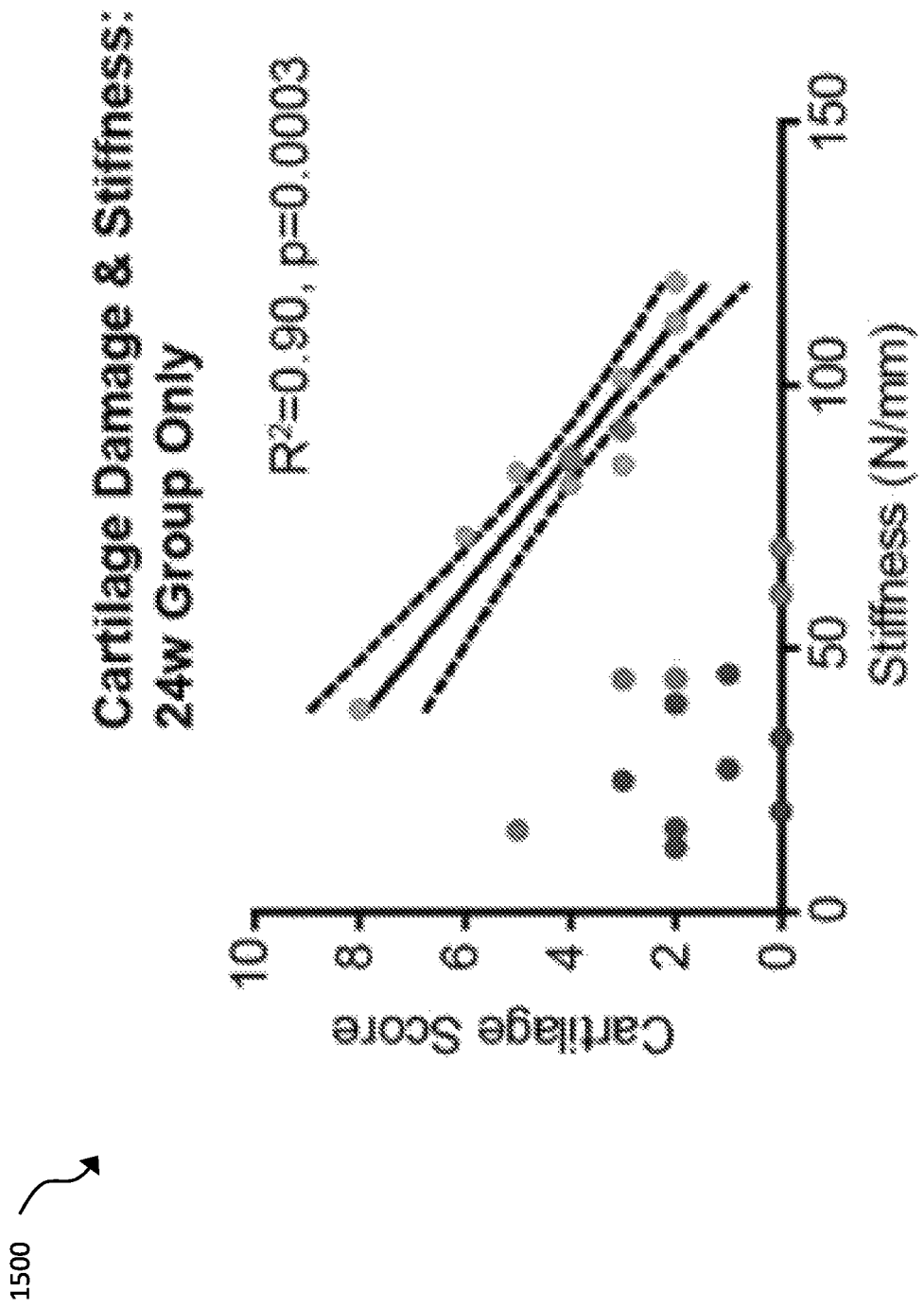
FIG. 15 is another plot showing cartilage score vs. stiffness (N/mm) for the three different animal groups, with an illustrated inverse relationship between cartilage score and ACL stiffness at 24 w ($R^2$=0.90, p<0.0003) that was not present at the earlier time points.

With the exception of two animals, all contralateral cartilage scores were zero (no damage). FIG. 13 shows a plot 1300 of stiffness corresponding to the healing durations of 6, 12, and 24 w. The plot 1300 shows that ACL linear stiffness increased with healing duration. ACL stiffness at 12 w (p=0.003) and 24 w (p<0.0001) was significantly greater than stiffness at 6 w, as shown in plot 1300. There was no relationship between cartilage damage and ACL stiffness at 6 w ($R^2$=0.04; p=0.65), 12 w ($R^2$=0.02; p=0.77), or when the data from all animals were pooled ($R^2$=0.02; p=0.47;), as illustrated in plot 1400, shown in FIG. 14. There was a strong and significant inverse relationship between cartilage damage and ACL stiffness at 24 w ($R^2$=0.90, p<0.0003), as illustrated in plot 1500, shown in FIG. 15.

Discussion

Using a translational model of ACL repair, we tested the hypotheses that ACL stiffness would increase over time, and that cartilage damage would be inversely related to ACL stiffness after 24 w of healing, but not within the first 12 w of healing. The results supported these hypotheses, whereby a relationship was evident only at the later healing time point of 24 w. It also appears that this relationship may begin to emerge at 12 w. The results show that three of the 12-week animals grouped with the 24 w animals, while the remainder of the 12 w animals grouped with the 6-week animals. We chose to evaluate ACL stiffness, as opposed to failure or yield load, because repetitive, low-load activities of daily living are proposed as having a significant role in the slow but progressive nature of PTOA pathogenesis.[1] Therefore, ACL stiffness may better reflect the low load behavior of the healing ACL. Evidence from computational[5] and experimental models[6] suggest that a more compliant ACL results in abnormal joint biomechanics. Coupled with previously established relationships between increased cartilage damage severity and joint kinematics abnormality 20 w after ACL transection in sheep models,[7,8] the cartilage damage observed in the Yucatan minipig model 24 w post-operatively may be the result of altered joint contact mechanics Conversely, the very mild cartilage damage noted at 6 w and at 12 w in some of the animals in this group may be due to inflammatory processes associated with the surgery itself.[9,10] Longitudinal studies that use magnetic resonance imaging to estimate changes in ACL stiffness and cartilage damage in vivo in these surgical models are ongoing, and may provide additional insight into the biological and mechanical processes that modulate PTOA pathogenesis.

The results indicate that restoring ACL stiffness may be necessary in order to mitigate cartilage damage progression following surgical ACL repair and it also demonstrates the value of measuring the mechanical properties of a healing ligament or graft on long term joint health.

Example 11 References

1. Andriacchi, T P, et al. 2004. Ann Biomed Eng(32). 2. Tashman, S, Araki, D. 2013. Clin Sports Med(32). 3. Proffen, B L, et al. 2013. Orthop J Sports Med(1). 4. Murray, M M, Fleming, B C. 2013. Am J Sports Med(41). 5. Li, G, et al. 2002. Ann Biomed Eng(30). 6. Nguyen, D T, et al. 2013. Tissue Eng Part A(19). 7. Beveridge, J E, et al. 2014. J Orthop Res(32). 8. Beveridge, J E, et al. 2013. J Orthop Res(31). 9. Huebner, K D, et al. 2014. J Orthop Res(32). 10. Sieker, J T, et al. 2017. J Orthop Res.

Example 12—Structural Properties of Healing ACL Predicted from MR $T_2$*, Signal Intensity, and Ligament Volume Using magnetic resonance (MR) imaging, we have developed time-specific $T_2$* relaxometry-based linear regression models to predict the structural properties of surgically repaired anterior cruciate ligament (ACL) within the first 24 weeks (w) post-repair in Yucatan minipigs.[1] MR $T_2$* sequences can require long acquisition times that may be challenging to implement clinically. In some cases simpler imaging and analyses techniques based on ACL signal intensity and volume may be sufficient to gauge the functional status of the ACL. Accordingly, one purpose of this study was to investigate to what extent the predicted structural properties of the healing ACL would differ between $T_2$*-based multiple linear regression models(1,2), and signal intensity (SI) and volume-based regression models(6). We hypothesized that the $T_2$* linear regression models would be better able to predict the ACL structural properties than the SI and volume models within 6-24 w post-repair.

Methods

Subjects: Twenty-four 15±1 month old (12 castrated males, 12 females) Yucatan minipigs were randomized to receive primary suture repair with (n=12; 6 female) or without (n=12; 6 female) a scaffold to enhance healing after ACL transection.[3]

Animals were then randomly allocated to one of three groups (n=8 per group with an equal number of primary suture repairs vs. scaffold enhanced repairs and males/females in each group) based on post-operative healing duration of 6, 12, or 24 weeks (w).

In vivo MR imaging: ACLs were imaged using a 3D gradient 4-echo sequence at either 6, 12, or 24 w post-repair (n=8 at each time point). All animal procedures were approved by the Institutional Animal Care and Use Committee.

ACL structural properties: Following the allotted healing period, animals were euthanized. Following euthanasia, the hind limbs were dissected leaving only the femur-ACL-tibial complex intact. The proximal end of the femur and distal end of the tibia of each femur-ACL-tibial complex were potted, mounted in a custom frame, and tensile tested to failure to acquire load-displacement data.[4] Failure load (N), yield load (N) and linear stiffness (N/mm) were calculated from the load-displacement data.

ACL $T_2^*$ estimation: ACLs were segmented manually by a single segmenter. $T_2^*$ relaxation times were calculated for all voxels encompassed by the ACL on a voxel-wise basis by fitting a mono-exponential function to the signal decay across the four echoes.[5]

Statistical models: For each structural property, four competing multiple linear regression models were fitted to the log-transformed data. The linear regression models include: (1) a first model based on two ACL sub-volumes (in mm$^3$) containing voxels with the shortest $T_2^*$ relaxation times ($Vol_1$), and the longest $T_2^*$ relaxation times ($Vol_4$) (i.e., "$T_2^*$" model); (2) a second model based on the median signal intensity (SI) of all ACL voxels and the total ACL volume (i.e., "(SI+Vol)" model); (3) a third $T_2^*$ model that incorporated changes in $T_2^*$ relaxation times over time; and (4) a fourth (SI+Vol) model that incorporated changes in SI and volume over time. The $T_2^*$ model with $Vol_1$ and $Vol_4$ was based on previous work that binned the ACL voxels using the following $T_2^*$ relaxation ranges: $Vol_1$=0-12.5 ms; $Vol_4$=37.6-50 ms.[2] The median ACL SI was calculated from the MR images of the second echo (TE=6.86 ms) of the 4-echo gradient sequence, and was then normalized to the gray values of the femoral cortical bone.[6] The Akaike Information Criterion (AIC), which provides an objective measure of the trade-off between goodness of regression fit and model complexity, was used to test the study hypothesis by comparing the AIC values of the four models. Lower AIC values indicate superior model performance.[7] Bland-Altman plots were used to evaluate the agreement between the predicted and actual structural property values using the ratio of actual to predicted values on the y-axis to account for the lognormal distribution.

Results

Table 1 shows regression model AIC values for the four models that were tested. The AIC values of the $T_2^*$ models were lower than those of the corresponding SI and volume regression models regardless of whether the effect of time was incorporated into the model (+/−time).

TABLE 1

Regression Model AIC Values.

| | AIC Values | | | |
|---|---|---|---|---|
| | (SI + Vol) | | $T_2^*$ | |
| | −time | +time | −time | +time |
| Failure Load | 52.2 | 41.2 | 43.0 | 29.2 |
| Yield Load | 53.0 | 40.2 | 43.8 | 27.0 |
| Stiffness | 46.5 | 39.9 | 33.9 | 27.3 |

Figure 16:
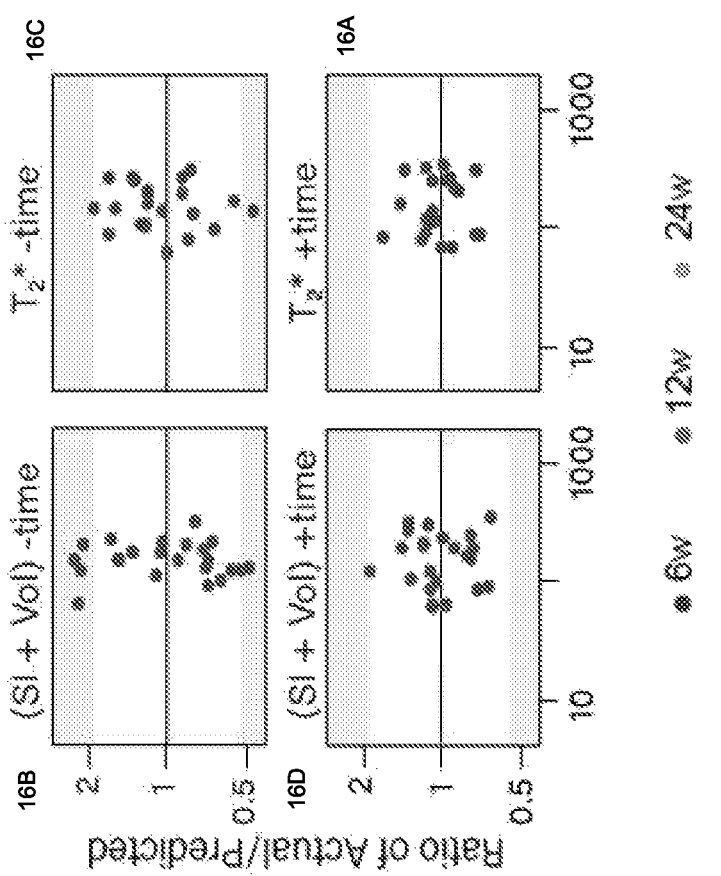
FIG. 16 presents four Bland-Altman plots showing ratios of actual failure loads to predicted failure loads from four different models used to predict ACL failure loads after ACL Repair for animal subjects separated into three groups corresponding to post-operative healing durations of 6, 12, and 24 weeks after ACL repair: Plot 16A shows a ratio of actual failure load to failure load predicted by a first model; Plot 16B shows a ratio of actual failure load to failure load predicted by a second model; Plot 16C shows a ratio of actual failure load to failure load predicted by a third model; and Plot 16D shows a ratio of actual failure load to failure load predicted by a fourth model.

FIG. 16 shows four Bland-Altman plots 16A, 16B, 16C, 16D, showing ratios of actual failure loads to predicted failure loads corresponding to each of the four models described above. In the plots 16A, 16B, 16C, 16D, data points that are closest to a value of 1 on the Y axis represent the best agreement between actual and predicted failure loads. The plots 16A, 16B, 16C, 16D plots revealed that the $T_2^*$ model-predicted values were in closer agreement with the actual values than those predicted by the SI and volume model. Similar results were observed for other structural properties such as yield load and stiffness.

Figure 17:
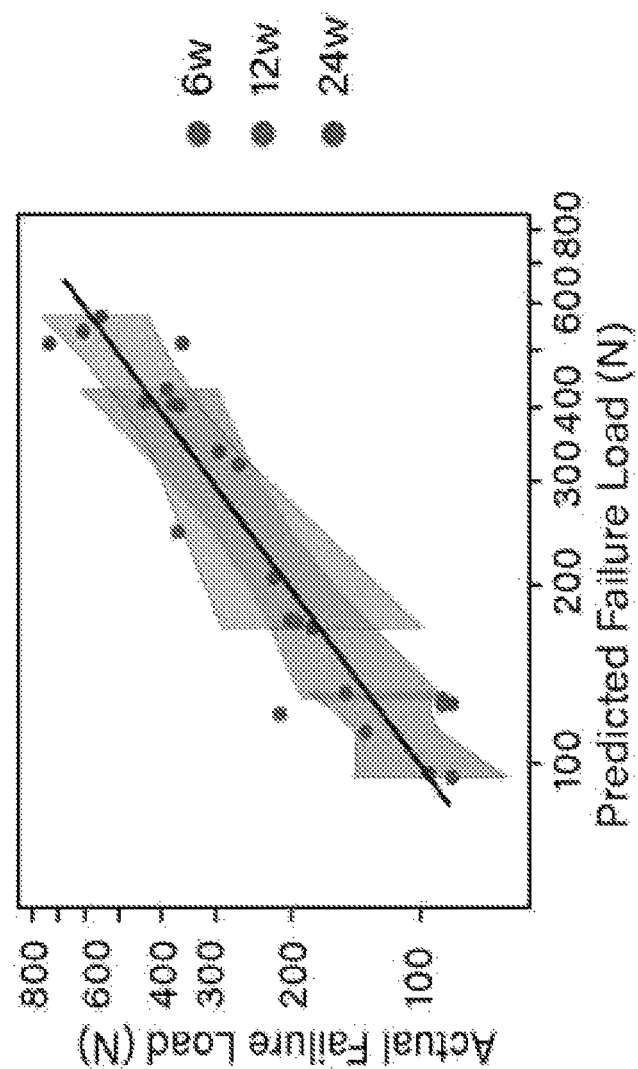
FIG. 17 is a plot of actual ACL failure load vs. predicted ACL failure load corresponding to the same three groups of animals shown in FIG. 16.

In some cases, values of certain structural properties increased with healing time. FIG. 17 shows a plot 1700 of actual failure load as a function of predicted failure load. As illustrated in plot 1700, the actual and predicted failure loads increased with increased with increased duration of post-operative healing. In the plot 1700, the shaded areas represent 95% confidence intervals for each of the three post-operative healing durations that were evaluated. Similar trends were observed for other structural properties such as yield load and stiffness.

Discussion

The results indicate that the $T_2^*$ linear regression models would be better able to predict the ACL structural properties than the SI and volume models. This study supports our earlier work where a $T_2^*$ model that used the four ACL sub-volumes (i.e., $Vol_{1-4}$) explained a greater proportion of the variation in structural properties after 52 w of healing compared to a (SI+Vol) model.[2] The current study makes several advancements over our earlier work. For example, in the current work, (1) all scans were collected in vivo; (2) more echoes were used to fit the mono-exponential decay function; and (3) structural properties were modeled at earlier healing phases that correspond to when clinicians consider increasing patient activity levels post-ACL surgery.

The results indicate that a $T_2^*$-specific MR sequence and $T_2^*$-specific linear regression models can be used to predict the structural properties of healing ACL within the first 24 w post-repair.

Example 12 References

1. Beveridge, J, et al. 2017. ASB. Boulder, C O. 2. Biercevicz, A M, et al. 2014. J Orthop Res (32). 3. Murray, M M, Fleming, B C. 2013. Am J Sports Med (41). 4. Fleming, B C, et al. 2009. Am J Sports Med (37). 5. Helms, C A, et al. 2008. Musculoskeletal MRI. Saunders, Pa. 6. Biercevicz, A M, et al. 2013. Am J Sports Med (41). 7. Ramsey, F L, Schafer, D W. 2002. The statistical sleuth, 2nd ed. Pracific Grove, Druxbury. 8. Proffen, B L, et al. 2013. Orthop J Sports Med (1).

Figure 18:
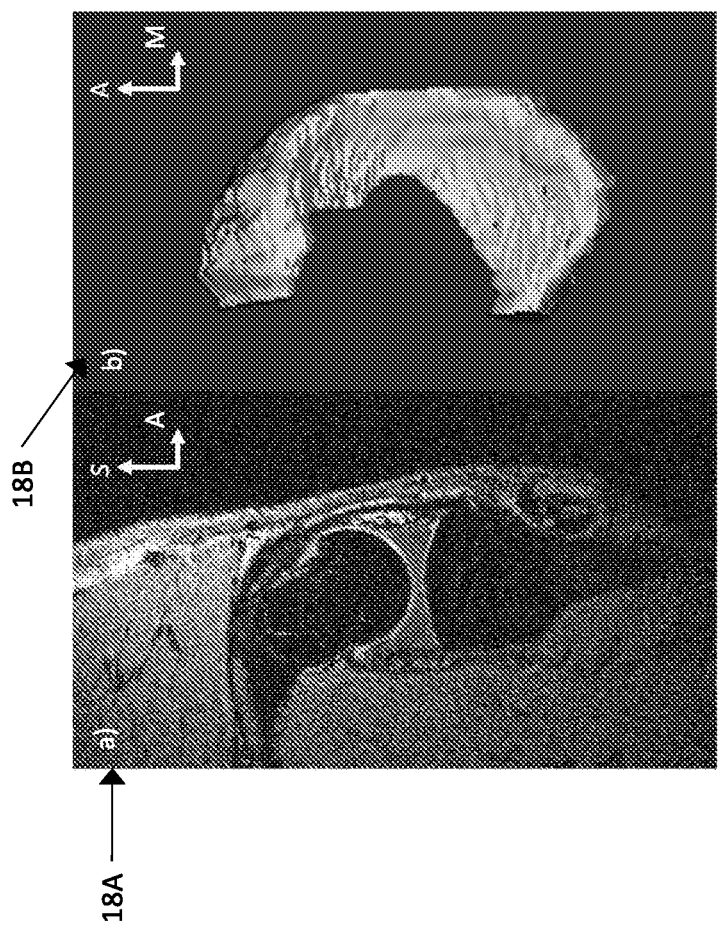
FIG. 18 is an image 18A of a single sagittal slice of a segmentation mask of a medial meniscus in vivo, and an image 18B of a completed segmentation mask of a medial meniscus. In image 18A, an anterior side of the medial meniscus is shown at the right of the segmentation mask, and a superior side of the medial meniscus is shown at the top of the segmentation mask. In image 18B, an anterior side of the medial meniscus is shown toward the top of the image 18B, while a medial side of the medial meniscus is shown toward the right of the image 18B.

Example 13—Assessing Meniscus Integrity Post-ACL Repair with MRI $T_2^*$ Relaxometry Patients with an ACL tear are at an increased risk for the development of post-traumatic osteoarthritis[1]. The injury can result in numerous systemic effects to the knee. For example, in some cases, a torn ACL can lead to degradation of the meniscus. Because meniscal trauma often occurs concomitantly with ACL injury, the effects of ACL injury and surgical ACL repair (ACLR) on meniscal health have been difficult to isolate. Quantitative MRI $T_2^*$ relaxometry has previously been validated as a method to non-invasively map soft tissue quality and quantity in vivo[2]. With this method, we examined whether ACL transection followed by ACLR induced meniscal alterations (i.e. changes in meniscal volume and median $T_2^*$ relaxation time) independent of acute ACL injury. We hypothesized that ACLR does not affect the medial meniscus $T_2^*$ relaxation time or volume within the first 24 weeks post-surgery Methods 24 adolescent Yucatan minipigs underwent unilateral ACL transection followed by immediate surgical repair of the ACL. The animals were followed for 6 (n=8), 12 (n=8) and 24 weeks (n=8) post-operatively. MRI scans were conducted in vivo with a 3T magnet and six-channel flex coil (Siemens PRISMA, Erlangen, Germany) using a 4-echo gradient sequence, voxel size of 0.3125 mm×0.3125 mm×0.8 mm, 512×512 matrix. Surgical and contralateral limbs were imaged at each time point (e.g., 6, 12, and 24 weeks). The MRI scans provided an image stack for each animal. The image stacks included spatially sequential cross-sectional images of the limbs, including the meniscus. The medial meniscus tissue was segmented from the image stack using Mimics software (Materialise Mimics Research 19.0, Leuven, Belgium). Voxel $T_2^*$ relaxation times were calculated in MATLAB® (MathWorks®, Natick, Mass., USA), then mapped to the medial meniscus voxels designated in a segmentation mask. For each animal, a medial meniscus volume was calculated in MATLAB® as the sum of voxel volumes contained in the segmentation mask. FIG. 18 shows an image 18A of a single sagittal slice of a segmentation mask of a medial meniscus in vivo, and an image 18B of a completed segmentation mask of a medial meniscus. In image 18A, an anterior side of the medial meniscus is shown at the right of the segmentation mask, and a superior side of the medial meniscus is shown at the top of the segmentation mask. In image 18B, an anterior side of the medial meniscus is shown toward the top of the image 18B, while a medial side of the medial meniscus is shown toward the right of the image 18B. A 2-way analysis of variance with Holm-Sidak multiple comparisons test was used to compare the median $T_2^*$ relaxation times and medial meniscus volumes between the surgical and contralateral limbs across time points. The analysis was performed using SigmaPlot® Systat Software Inc., San Jose, Calif., USA).

Results

Figure 19:
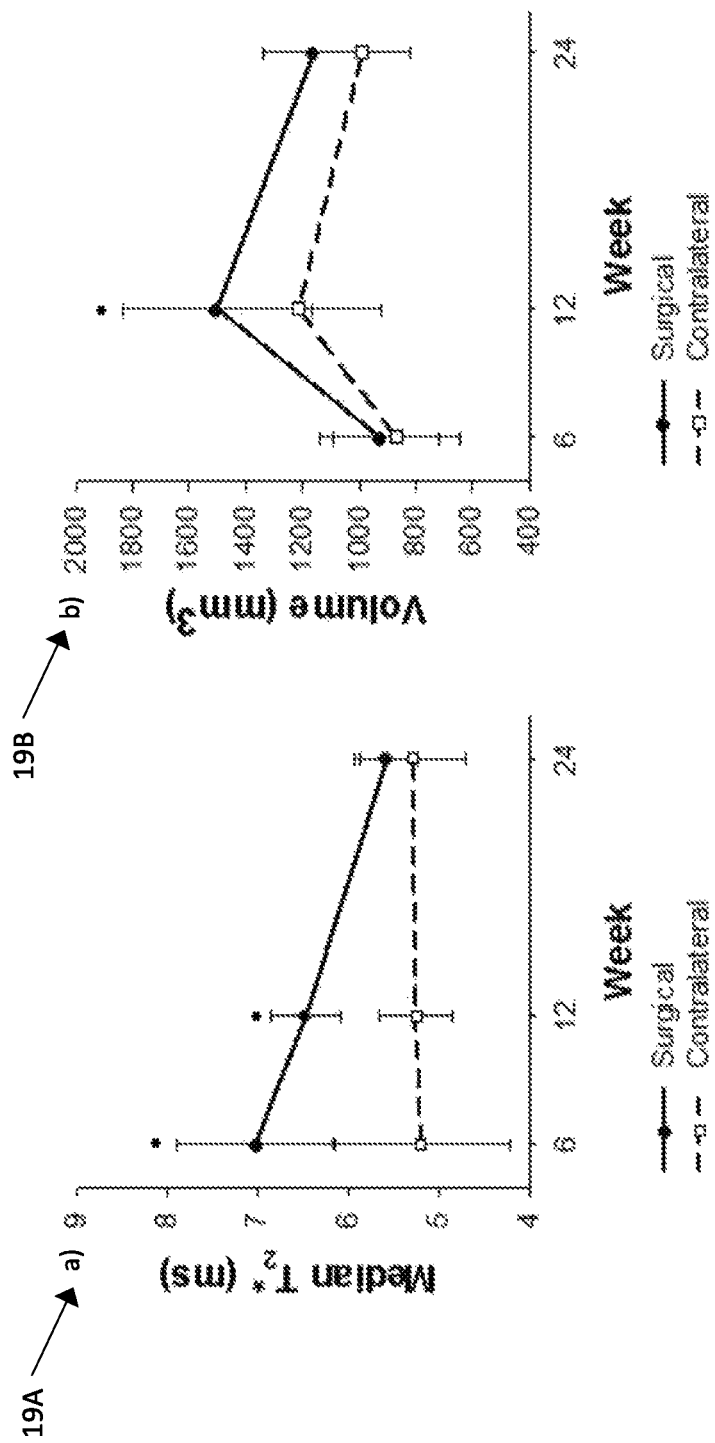
FIG. 19 is a plot 19A of median $T_2$* (ms) relaxation times and a plot 19B of meniscal volume ($mm^3$) for the same three groups shown in FIG. 16.

There was a statistically significant interaction between time and limb. Median $T_2^*$ relaxation times were significantly greater in the medial meniscus of the surgical limb compared to the contralateral limb at 6 and 12 weeks post-surgery, as illustrated in plot 19A, shown in FIG. 19. However, no significant difference was observed at 24 weeks. A significant difference in the volumes of the medial menisci between limbs was only seen at the 12 week time point, as illustrated in plot 19B, shown in FIG. 19.

Discussion:

The surgical limb initially displayed greater $T_2^*$ relaxation times, which can be indicative of meniscal alterations, and can potentially be related to changing collagen organization and/or tissue hydration. An increase in meniscal volume was also observed at 12 weeks. The increase in meniscal volume at 12 weeks may be due to a change in water content. It is probable that these changes are due to ACLR because the ACL transection was performed in isolation, and there were no concomitant meniscal injuries at the time of surgery. Interestingly, by 24 weeks, $T_2^*$ values in the surgical limb were comparable to that of the contralateral limb, suggesting that the meniscal changes were temporary and resolved by 24 weeks.

The results indicate that ACL injury and repair initially induced structural changes in the medial meniscus that resolved by 24 weeks. Predicting the mechanical properties of the healing ligament or graft will provide important information related to joint healing after ACL surgery.

Example 13 References

1. Proffen B, et al. 2016. JOR(34), p. 995-1003 2. Biercevicz A M, et al. 2014. JOR(32), p. 492-499.

Example 14—Magnetic Resonance Measurements of Tissue Quantity and Quality Using $T_2^*$ Relaxometry Predict Temporal Changes in Biomechanical Properties of the Healing ACL One purpose of this study was to develop a magnetic resonance $T_2^*$ relaxometry-based multiple linear regression model to predict the structural properties of the healing anterior cruciate ligament (ACL) over a 24-week healing period following ACL repair in Yucatan minipigs. Two hypotheses were tested: (1) that a regression model based on ACL sub-volumes containing short and long $T_2^*$ relaxation times would outperform a competing model based on sub-volumes of short $T_2^*$ relaxation times only; and (2) that an optimized regression model would be capable of predicting ACL structural properties between 6 and 24 weeks post-repair. ACLs were imaged in 24 minipigs (8/group) at either 6, 12, or 24 weeks after ACL repair. The structural properties of the ACLs were determined from tensile failure tests. Four multiple linear regression models of increasing complexity were fitted to the data. Akaike Information Criterion values and Bland-Altman tests were used to compare model performance and to test the hypotheses. The structural properties predicted from the multiple linear regression model that was based on the change in ACL sub-volumes of both the short and long $T_2^*$ relaxation times over the healing period were in closest agreement to the measured values. This result suggests that the amounts of both organized and disorganized collagen, and the change in these quantities over time, are required to predict the structural properties of healing ACLs accurately. Clinical Significance: Our time-specific, $T_2^*$-based regression model may allow us to estimate the structural properties of ACL repairs in vivo longitudinally.

Anterior cruciate ligament (ACL) tear is one of the most common sports injuries requiring surgical treatment.[1,2] Whereas in vitro studies have provided insight into the strength of various surgical repair or reconstruction techniques at time zero,[3-7] and cross-sectional animal studies into the strength of healing via post-mortem testing,[8-15] the in vivo biomechanical properties of the healing ACL or graft remains largely unknown. Because of its non-invasive nature, magnetic resonance (MR) imaging is an attractive method to probe the relationship between MR signal properties and the structural properties of the native ACL or ACL graft in vivo.[16-18] Quantitative information related to in vivo ACL function can provide researchers a means to monitor the integrity of the graft or ACL repair over time, and might give surgeons a quantitative metric with which to develop and gauge return to sport criteria.

We have previously developed a multiple linear regression model that predicts the structural properties of both the ACL graft and ACL repair in Yucatan minipigs.[16] The minipig was selected because of its anatomic,[19] biomechanical,[20] and biological[21] similarities to human knees.[22] We subsequently refined the regression model to use MR $T_2^*$ relaxation times[17] to circumvent the pitfalls of using signal intensity, which can be both sequence and magnet-dependent.[23] Because $T_2^*$ relaxation time is related to collagen fibril organization, water content, and local magnetic field inhomogeneities,[24] and shorter $T_2^*$ relaxation times have been shown to reflect more highly organized meniscus[25] and ligament[26] structure, $T_2^*$ relaxation time provides an indication of tissue "quality". Using this MR relaxometry approach, we determined that a combination of four ACL sub-volumes that spanned a range of $T_2^*$ relaxation times from 0-50 ms predicted the structural properties (failure load, yield load and linear stiffness) of the ACL one year after ACL repair.[17] Of the four ACL sub-volumes included in the model, the sub-volume containing the shortest $T_2^*$ relaxation times contributed most to the prediction outcomes. In some cases, the regression model can be time-invariant, meaning that the relationship between the dependent variable and the predictor terms would be linear, and that the slope of this relationship would be the same irrespective of the stage of wound healing. If the model meets this criterion, then a single model can be used to predict structural properties over a range of post-operative healing periods within the time frame used to construct the model.

Although we have shown that the amount of collagen and the degree of organization are important determinants of the healing ACL structural properties,[16,17] the relative contribution of these two qualities are likely specific to each phase of wound healing.[9,27,28] At later stages of healing, collagen becomes more organized and thus the ACL sub-volume containing shorter $T_2^*$ relaxation times would be expected to dominate the performance of the model; however larger proportions of amorphous tissue, which are associated with scar formation, may be present at earlier stages of wound healing.[29] Therefore the amount of disorganized collagen— reflected by longer $T_2^*$ relaxation times—may be an important determinant of the ACL structural properties at earlier healing stages, and regression models that incorporate the transition from disorganized to organized collagen may perform better in predicting the structural properties over time.

In our previous regression models,[16,17] we utilized the $R^2$ value to evaluate the variability associated with our predicted structural properties. However, $R^2$ values may not necessarily provide the optimal means to compare model performance because they also increase as the number of predictor variables increases.[30] In contrast, the Akaike Information Criterion (AIC) provides an estimate of the information lost for a given regression model and it incorporates a penalty function for the number of model parameters. In this way, the AIC provides an objective measure of the trade-off between goodness of fit of the regression model versus its complexity, where lower AIC values indicate superior performance.[30]

The study objective was to optimize a regression model to predict the structural properties of the healing ACL in ACL-repaired minipigs using MR $T_2^*$ relaxometry data acquired at 6, 12 and 24 weeks. We hypothesized that the AIC value of a linear regression model that included the ACL sub-volumes based on both short and long MR $T_2^*$ relaxation times and time-specific effects of healing would be lower than the AIC value of a more simplified model that focused on the sub-volume of the shortest MR $T_2^*$ relaxation times only. We further hypothesized that the structural properties predicted from the linear regression models that incorporated the multiple ACL sub-volumes and time-specific effects of healing would be in closer agreement to the actual values.

Methods

Animals and Surgical Procedure.

Twenty-four (12 castrated males, 12 females; Sinclair Bio Resources, Mo.) 15±1 month old Yucatan minipigs were randomized to receive primary ACL suture repair with (n=12; 6 female) or without (n=12; 6 female) a scaffold to enhance healing.[31] The two procedures were used in an effort to increase the variability in the structural properties from which the regression model would be optimized. The sample size of n=24 was calculated to maintain >95% power to detect a significant increase in $R^2$ from 0.74 (based on our previous ACL MR signal analyses[16]) at alpha=0.05. All animals were deemed healthy by veterinary staff prior to the start of the study, and all procedures were approved by the Institutional Animal Care and Use Committee. Animals were housed individually in pens (minimum pen size 22.4 ft$^2$), which were located adjacent to one another, on a 12/12 hour light/dark cycle, fed twice daily with a lab-based died, had free access to drinking water, and were monitored daily by veterinary staff. Environments were enriched with toys on a regular basis. At the time of surgery, animals were sedated using telozol with xylazine, then intubated and maintained under general anaesthesia using isofluorane. The ACL was transected at the junction of the proximal and middle thirds of the ligament Immediately following transection, animals received primary suture repair either with, or without, the scaffold.[9] The enhanced repair procedure has been described in detail previously.[31] Other than the scaffold, the two surgical procedures were equivalent. Animals were allowed unrestricted weight bearing following the surgery.

In vivo MR imaging. Animals were randomized in equal numbers to one of three imaging groups where the surgical knees were imaged in vivo just prior to euthanasia after 6, 12 or 24 weeks (w) of healing (n=8 per group; equal male/females within groups; equal number of ACL repairs with the scaffold versus without within each group). The baseline mean weights of the 6-, 12- and 24-week imaging group animals were 54.2±4.9 kg, 53.1±2.8 kg and 52.5±4.2 kg, respectively. Throughout MR imaging, animals were sedated and maintained under general anesthesia using the same drug regimen described for the surgical procedures. The knees were imaged with a 3T magnet (Prisma; Siemens, Erlangen, Germany) using a six-channel flexcoil (Siemens), and a 3D gradient multi-echo sequence. The sequence for seven of the eight 6 w pigs was run using the following parameters: FOV=160×160 mm; ST/gap=0.8 mm/0 mm; TR=29 ms; FA=12°. A 384×384 acquisition matrix (voxel size of 0.42×0.42×0.8 mm) with 6 echoes at TE=2.48, 6.86, 11.24, 15.62, 20.00 and 24.38 ms (scan time=19:25). For all other animals, MR images were obtained from using a 512×512 matrix (voxel size of 0.31×0.31×0.8 mm) and 4 echoes at TE=2.8, 7.88, 12.96 and 18.04 ms (scan time=25:50). The range of echo times was selected based on our previous work that has shown that these TEs capture MR signal intensities relevant to ACL healing specifically.[17,26] The matrix resolution was increased to enhance visualization of the ACL border. The differences in $T_2^*$ fit of these in vivo data as a result of differing echo number and resolution were minimal.[32] Animals were euthanized immediately after imaging with an injection of Beuthanasia-D, and the hind limbs were harvested and frozen.

ACL $T_2^*$ Estimation.

ACLs were segmented manually (Mimics v16, Belgium) from the $T_2^*$ image stack by a single observer. $T_2^*$ relaxation times were determined by fitting an monoexponential decay function[33,34] to the segmented voxels across echo times (mean $R^2$ of the least-squares function fit was 0.87±0.04). ACL voxels were then binned into four sub-volumes based on increasing ranges of voxel $T_2^*$ relaxation times as previously reported:[17] $Vol_1$=0-12.5 ms; $Vol_2$=12.6-25 ms; $Vol_3$=25.1-37.5 ms; $Vol_4$=37.6-50 ms. $Vol_1$ is the sub-volume (in mm$^3$) of the ACL voxels containing the most organized collagen, whereas $Vol_4$ is the sub-volume containing the least organized collagen. All calculations were performed using custom-written software with Matlab® (v2015b, Natick, Mass.).

ACL Structural Properties.

Limbs were thawed to room temperature, and dissected leaving only the femur-ligament-tibia complex and the associated peri-ligamentous scar tissue surrounding the healing ACL.[8] The proximal end of the femur and distal end of the tibia were potted in PVC pipe and urethane resin. The potted ends of the specimen were then rigidly mounted in a custom frame such that the long axis of the ACL was aligned with the direction of the applied tensile load. A servohydraulic material testing system (MTS 810; Prairie Eden, Minn.) applied the tensile loads to failure at a rate of 20 mm/min[8,35] Maximum load, yield load, and linear stiffness of the ACL were calculated from the load-displacement data.

Statistical Methods.

All regression modeling was carried out using proc glimmix in SAS version 9.4 (The SAS Institute, Cary, Conn.). All data were log-transformed to account for the skewed distribution. For each structural property, generalized linear modeling was used to build and compare four competing multiple linear regression models:

A 2-parameter model=$Vol_1$ only with no effect of healing time

A 4-parameter model=$Vol_1$ and $Vol_4$ with no effect of healing time

A 6-parameter model=$Vol_1$ at 6 w, 12 w, 24 w and ($Vol_1$×healing time) interaction A 12-parameter model=the same six parameters as (3), with the addition of $Vol_4$ at 6 w, 12 w, 24 w; ($Vol_1$×$Vol_4$) interaction; and three-way ($Vol_1$×$Vol_4$×healing time) interaction The effect of healing time was modeled by considering 24 w as the "baseline" for the $Vol_1$, $Vol_4$ and the interaction terms, and subsequently modeling the difference in values from baseline to 6 and 12 w. Classical sandwich estimation was used to adjust for model misspecification. These models were fit by maximizing residual likelihood rather than minimizing variance. The resultant Akaike Information Criterion (AIC) was used to compare model performance. For each structural property, model predictions were then compared to the measured values in a separate optimized log-normal model, mimicking the application of the model formula in future testing datasets. Using the optimized models, the slopes of the predicted structural properties and the actual properties at each time point were compared to determine whether the optimized model was time-invariant. Modified Bland-Altman plots were constructed to visualize the agreement between model-predicted and actual values with the model's predicted values on the x-axis (log-spaced) and the ratio of the actual value to the predicted value on the y-axis. In this way, a ratio equal to 1 on the y-axis indicates perfect agreement, with values greater than 1 indicating that the actual property was higher than the model-predicted, and below 1 indicating that the actual property was lower. These modifications to the traditional Bland-Altman plot were made because the distribution of the data was lognormal.

Results

At the time of MR imaging, we noted that only a small volume of tissue with hyperintense signal spanned the anatomical ACL location in one of the 6 w enhanced repair surgeries. Failure of the ACL repair surgery in this one subject was confirmed at dissection, and the animal was excluded from the analyses. Data from 23 animals were included in the final analyses: 7 animals in the 6 w imaging group, and 8 animals in each of the 12 and 24 w imaging groups.

ACL Sub-Volumes.

Figure 20:
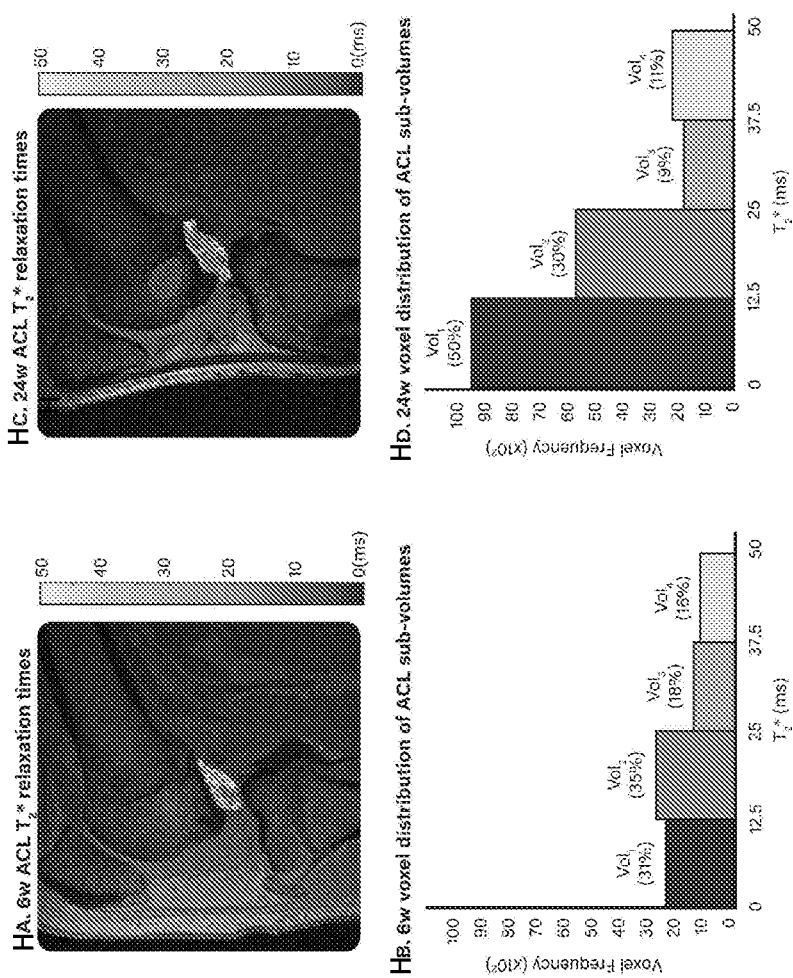
FIG. 20 shows image maps 20A, 20C of ACL $T_2$* relaxation times of a single MR slice of the healing ACL for representative animals at either 6 w and 24 w, respectively, as well as corresponding plots 20B, 20D showing distributions of voxel frequency. In plots 20B, 20D, percentages values above each bar indicate percentages of total volume for each ACL sub-volume.

FIG. 20 shows image maps 20A, 20C of ACL $T_2$* relaxation times of a single MR slice for representative animals at either 6 w and 24 w, respectively, as well as corresponding plots 20B, 20D showing distributions of voxel frequency. In plots 20B, 20D, percentages values above each bar indicate percentages of total volume for each ACL sub-volume. $Vol_1$ represented between 20% (6 w) and 65% (24 w) of the ACL total volume post-repair, and $Vol_4$ represented between 3% (24 w) and 29% (6 w).

Model Performance.

The Akaike Information Criterion value for the failure load, yield load and linear stiffness models was lower for the models that included the time-specific effects of healing, as shown in Table 2.

TABLE 2

| Model AIC values (unitless) | | | |
|---|---|---|---|
| | Failure Load | Yield Load | Stiffness |
| 1. $Vol_1$ | 38.89 | 40.22 | 32.68 |
| 2. $Vol_1$ & $Vol_4$ | 43.00 | 43.84 | 33.92 |
| 3. $Vol_1$ with time | 29.28 | 25.51 | 29.58 |
| 4. $Vol_1$ & $Vol_4$ with time | 29.92 | 27.03 | 27.28 |

Optimized Models.

Figure 21:
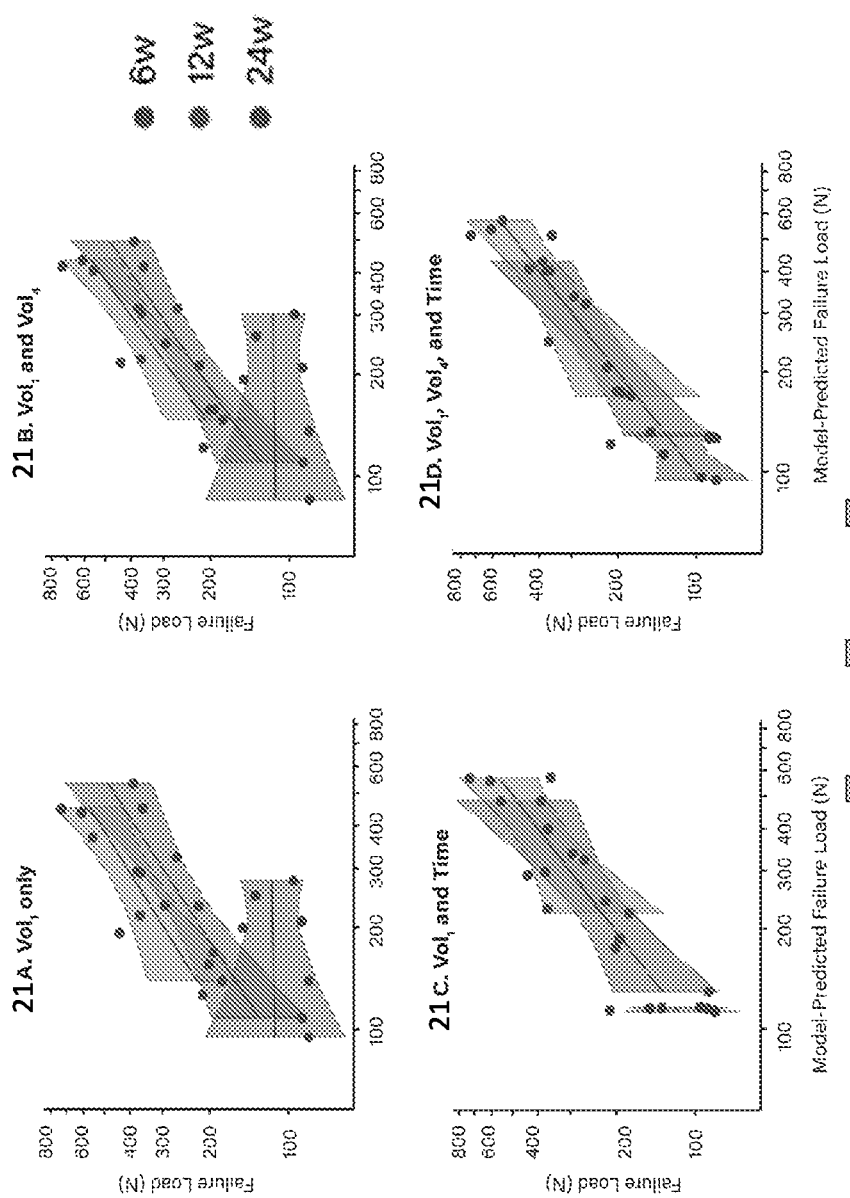
FIG. 21 shows plots 21A, 21B, 21C, 21D depicting model-predicted failure loads versus actual failure loads of the healing ACL for a 2-parameter model, 4-parameter model, 6-parameter model, and 12-parameter models, respectively. Shaded regions indicate ±95% confidence interval of the model estimates.
Figure 22:
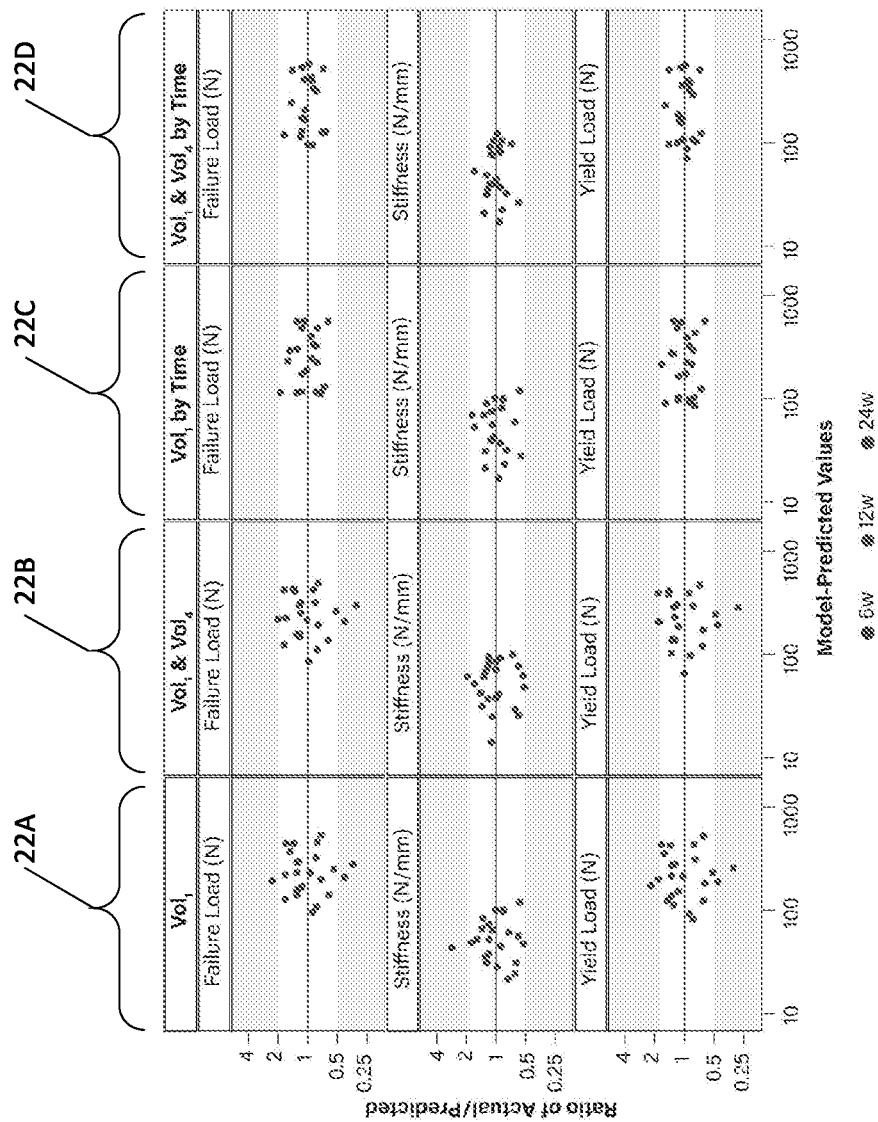
FIG. 22 is a series of four sets 22A, 22B, 22C, 22D of modified Bland-Altman plots characterizing ratios of actual values to predicted values of failure load, stiffness and yield load. Each set 22A, 22B, 22C, 22D of plots includes plots that show ratios of actual to predicted values of failure load (N), stiffness (N/mm) and yield load (N). The set 22A of plots corresponds to a 2 parameter model. The set 22B of plots corresponds to a 4 parameter model. The set 22C of plots corresponds to a 6 parameter model. The set 22D of plots corresponds to a 12 parameter model.

FIG. 21 shows plots 21A, 21B, 21C, 21D depicting model-predicted failure loads versus actual failure loads for the 2-parameter model, 4-parameter model, 6-parameter model, and 12-parameter models, respectively. Shaded regions indicate±95% confidence interval of the model estimates. Without accounting for time, the slopes of the actual versus predicted structural properties at 6 w were vastly different from the slopes at 12 and 24 w, as shown in plots 21A, 21B. Incorporating the effect of healing time in the regression model parameters resulted in the slopes being equal at all post-operative time points, as shown in plot 21C. Including the $Vol_4$ sub-volume, in addition to the effect of healing time, further improved the model predictions at 6 w in particular, as shown in plot 21D. Model predictions for values of yield load and stiffness followed similar patterns to those shown in images 21A, 21B, 21C, 21D. FIG. 22 shows four sets 22A, 22B, 22C, 22D of modified Bland-Altman plots that correspond the results of the predictive models described above. Each set 22A, 22B, 22C, 22D includes plots that show ratios of actual to predicted values of failure load (N), stiffness (N/mm) and yield load (N). The set 22A of plots corresponds to the results of the 2 parameter model. The set 22B of plots corresponds to the results of the 4 parameter model. The set 22C of plots corresponds to the results of the 6 parameter model. The set 22D of plots corresponds to the results of the 12 parameter model. As shown in FIG. 22, the results indicate that as the model complexity increased, the ratio of actual to predicted structural properties were closer in agreement (i.e., closer to 1).

Optimized Model Coefficients.

The coefficients of the optimized 12-parameter failure load, yield load and stiffness models used to predict the structural properties are shown in Table 3. The full 12-parameter models can be simplified to an applied format in order to predict the structural properties of the healing ACL at 6, 12 or 24 w time intervals specifically. The coefficients (B) for these applied models are shown in the right-hand columns of Table 3 under "Applied Format".

TABLE 3

12-Parameter model coefficients. Healing time effects are denoted by "Δ".

| Dependent Variable | Independent Variable | | Coefficient (B) | SE | P-value | Applied Format: | | |
|---|---|---|---|---|---|---|---|---|
| | | | | | | Time | Parameter | B |
| Failure Load (N) | 24 w Intercept | $B_0$ | 35.08 | 12.15 | 0.01 | 6 w | Intercept | 27.59 |
| | 6 w Δ Intercept | $B_1$ | −7.49 | 39.86 | 0.85 | | per $Vol_1$ | −3.88 |
| | 12 w Δ Intercept | $B_2$ | −56.11 | 33.16 | 0.12 | | per $Vol_4$ | −4.68 |
| | 24 w $Vol_1$ | $B_3$ | −4.29 | 1.96 | 0.05 | | per ($Vol_1 \times Vol_4$) | 0.80 |
| | 6 w Δ $Vol_1$ | $B_4$ | 0.41 | 6.20 | 0.95 | 12 w | Intercept | −21.03 |
| | 12 w Δ $Vol_1$ | $B_5$ | 8.85 | 5.30 | 0.12 | | per $Vol_1$ | 4.56 |
| | 24 w Δ $Vol_4$ | $B_6$ | −8.52 | 2.83 | 0.01 | | per $Vol_4$ | 3.99 |
| | 6 w Δ $Vol_4$ | $B_7$ | 3.84 | 6.37 | 0.56 | | per ($Vol_1 \times Vol_4$) | −0.70 |
| | 12 w Δ $Vol_4$ | $B_8$ | 12.51 | 6.70 | 0.09 | 24 w | Intercept | 35.08 |
| | 24 w ($Vol_1 \times Vol_4$) | $B_9$ | 1.28 | 0.46 | 0.02 | | per $Vol_1$ | −4.29 |
| | 6 w Δ ($Vol_1 \times Vol_4$) | $B_{10}$ | −0.48 | 0.98 | 0.64 | | per $Vol_4$ | −8.52 |
| | 12 w Δ ($Vol_1 \times Vol_4$) | $B_{11}$ | −1.97 | 1.07 | 0.09 | | per ($Vol_1 \times Vol_4$) | 1.28 |
| Yield Load (N) | 24 w Intercept | $B_0$ | 22.21 | 11.16 | 0.07 | 6 w | Intercept | 29.66 |
| | 6 w Δ Intercept | $B_1$ | 7.44 | 27.22 | 0.79 | | per $Vol_1$ | −4.18 |
| | 12 w Δ Intercept | $B_2$ | −37.86 | 34.15 | 0.29 | | per $Vol_4$ | −5.14 |
| | 24 w $Vol_1$ | $B_3$ | −2.30 | 1.82 | 0.23 | | per ($Vol_1 \times Vol_4$) | 0.86 |
| | 6 w Δ $Vol_1$ | $B_4$ | −1.88 | 4.26 | 0.67 | 12 w | Intercept | −15.64 |
| | 12 w Δ $Vol_1$ | $B_5$ | 6.00 | 5.46 | 0.30 | | per $Vol_1$ | 3.69 |
| | 24 w Δ $Vol_4$ | $B_6$ | −5.64 | 2.63 | 0.06 | | per $Vol_4$ | 2.97 |
| | 6 w Δ $Vol_4$ | $B_7$ | 0.50 | 4.56 | 0.91 | | per ($Vol_1 \times Vol_4$) | −0.54 |
| | 12 w Δ $Vol_4$ | $B_8$ | 8.61 | 6.88 | 0.24 | 24 w | Intercept | 22.21 |
| | 24 w ($Vol_1 \times Vol_4$) | $B_9$ | 0.83 | 0.43 | 0.08 | | per $Vol_1$ | −2.30 |
| | 6 w Δ ($Vol_1 \times Vol_4$) | $B_{10}$ | 0.03 | 0.71 | 0.97 | | per $Vol_4$ | −5.64 |
| | 12 w Δ ($Vol_1 \times Vol_4$) | $B_{11}$ | −1.37 | 1.10 | 0.24 | | per ($Vol_1 \times Vol_4$) | 0.83 |
| Stiffness (N/mm) | 24 w Intercept | $B_0$ | 68.05 | 4.47 | <0.0001 | 6 w | Intercept | −8.58 |
| | 6 w Δ Intercept | $B_1$ | −76.63 | 18.29 | 0.002 | | per $Vol_1$ | 1.91 |
| | 12 w Δ Intercept | $B_2$ | −127.78 | 42.93 | 0.013 | | per $Vol_4$ | 0.70 |
| | 24 w $Vol_1$ | $B_3$ | −9.62 | 0.73 | <0.0001 | | per ($Vol_1 \times Vol_4$) | −0.10 |
| | 6 w Δ $Vol_1$ | $B_4$ | 11.53 | 2.84 | 0.002 | 12 w | Intercept | −59.73 |
| | 12 w Δ $Vol_1$ | $B_5$ | 20.21 | 6.91 | 0.01 | | per $Vol_1$ | 10.59 |
| | 24 w Δ $Vol_4$ | $B_6$ | −15.74 | 0.99 | <0.0001 | | per $Vol_4$ | 11.41 |
| | 6 w Δ $Vol_4$ | $B_7$ | 16.43 | 2.89 | 0.0001 | | per ($Vol_1 \times Vol_4$) | −1.90 |
| | 12 w Δ $Vol_4$ | $B_8$ | 27.14 | 8.56 | 0.009 | 24 w | Intercept | 68.05 |
| | 24 w ($Vol_1 \times Vol_4$) | $B_9$ | 2.38 | 0.16 | <0.0001 | | per $Vol_1$ | −9.62 |
| | 6 w Δ ($Vol_1 \times Vol_4$) | $B_{10}$ | −2.48 | 0.46 | 0.0002 | | per $Vol_4$ | −15.74 |
| | 12 w Δ ($Vol_1 \times Vol_4$) | $B_{11}$ | −4.28 | 1.38 | 0.01 | | per ($Vol_1 \times Vol_4$) | 2.38 |

SE = Standard error.

Discussion

The AIC values of the linear regression models that incorporated the effects of healing time were lower than the AIC values of the more simplified models, indicating that these 6- and 12-parameter models performed better than the 2- and 4-parameter models for predicting ACL failure load, yield load, and stiffness (Table 2). Accordingly, the slopes across all healing times were co-linear only in the time-specific models, as shown in FIG. 21. The sets 22A, 22B, 22C, 22D of modified Bland-Altman plots, shown in FIG. 22, indicated that the 12-parameter model predictions were in closest agreement to actual values. These results supported our hypotheses that the AIC values would be lowest in models that incorporated the time-specific effects of healing and multiple ACL sub-volumes, and that the predicted structural properties predicted from this most complex model would be in closest agreement to the actual values.

The 2- and 6-parameter models focused on $Vol_1$ because this ACL sub-volume explained the greatest proportion of variance in our previous multiple linear regression models.[17] We expanded these models to include both $Vol_1$ and $Vol_4$ sub-volumes and their interaction terms with time, resulting in a 12-parameter multiple linear regression model. Previous prediction models were based primarily on the remodeling phase of healing at 52 weeks.[17] The current results presented herein indicate that a prediction term that captures some elements associated with early healing can be beneficial in order to predict ACL structural properties at time points between 6 and 12 w. Because $Vol_4$ encompasses voxels with much longer $T_2^*$ relaxation times compared to $Vol_1$ (35.6-50 ms vs. 0-12.5 ms, respectively), we believe that this sub-volume may capture these other constituents and biological processes associated with earlier stages of ACL healing.

Investigations in rabbit models of medial collateral ligament (MCL) wound healing have shown that the amount of disorganized scar tissue bridging the gap between ligament ends is a critical element in early extra-articular ligament healing.[29] Using the ligament maturity index (LMI), we found that the cellular subscores, in addition to the collagen organization scores, were predictive of the structural and material properties of the healing ACL in Yucatan minipigs.[28] In light of these studies, it seems reasonable to speculate that tissue quantity, even if it is disorganized and contains other tissue elements such as cells and vessels that are not directly reflected by short $T_2^*$ relaxation times, may be an important factor during early phases of ligament healing. In addition to providing unique information related to biological processes that may precede collagen remodeling, $Vol_4$ encompasses voxels that are at the opposite end of the spectrum to the information represented by $Vol_1$ voxels. For this reason, it is the sub-volume that is the least correlated with $Vol_1$, and therefore most likely to enhance the regression model performance Despite models yielding similar AIC values, adding $Vol_4$ and its interaction terms had the effect of spreading out the predicted ACL failure load, yield load and stiffness values at 6 w, as demonstrated by a comparison of x-axis values in plots 21C, 21D in FIG. 21. This increased dispersion in the predicted structural properties resulted in closer agreement between the model-predicted and actual structural properties, shown in FIG. 22. We can conclude from these results that, unlike the 6-parameter model, the 12-parameter model is likely to yield reasonable estimates of healing ACL structural properties at 6 w. Because the addition of the $Vol_4$ sub-volume influenced the model performance predominantly at the 6 w time point, it points to the fact that this sub-volume is especially important at early time points and reflects compositional elements related to the sub-acute healing process that may then modulate collagen organization at later phases of healing. Despite the complexity that the added terms of the 12-parameter regression model produces compared to the 6-parameter model, the similar AIC values of the two models suggests that the complexity is worth the tradeoff for superior model fit and the ability to predict structural properties throughout the transition from acute (6 w) to chronic (24 w) healing phases.

The signal to noise quotient (SNQ) is another non-invasive MR-based technique used to gauge ACL graft maturity that has been used by others.[18,36-39] The calculation involves sampling the MR signal intensity within a region of interest, and then normalizing the signal intensity to the background noise of the image slice. Like our linear prediction models, the SNQ of the ACL graft has shown some agreement with its underlying histological ultrastructure,[18,36-38] suggesting that normalized signal intensity yields relevant information regarding graft remodeling. In a way, inclusion of $Vol_1$ and $Vol_4$ voxels in our prediction models could be considered akin to the signal to noise quotient (SNQ) insofar as $Vol_1$ and $Vol_4$ sub-volumes represent the two extremes of MR $T_2^*$ properties much like the SNQ is based on two complementary sources of MR signal intensity information. However, there are some differences between the $T_2^*$ sub-volume approach and the SNQ metric. As an example the SNQ is dependent on discrete samples taken from a single image slice where the ACL is visible, while the sub-volumes described herein can be based on the entire ACL. As another example, signal intensity in the SNQ technique depends on the MR parameters used to acquire the images as well the hardware employed,[23] whereas $T_2^*$ is a more direct measure of tissue organization and composition given its dependence on the local magnetic field inhomogeneities arising from spin-spin interactions of the protons bound to collagen, and the collagen fibril organization within the tissue.[24] Additionally, another difference is that $T_2^*$ relaxation times do not require normalization. Therefore, the $T_2^*$ approach offers many advantages over the alternative SNQ technique, and is a more direct proxy of in vivo ligament maturity and biomechanical function.

Applying the parameter models to the same dataset from which the parameters were optimized allowed us to visualize the model slopes over time, and to construct modified Bland-Altman plots to assess the level of agreement between model-predicted and actual values. We were able to use these graphical representations to create context with which to interpret the unit difference in AIC values. By interpreting the AIC values alongside both FIGS. 21 and 22, it became clear that a difference in AIC values of two units or less (e.g., Table 2, row 3 vs row 4) may be inconsequential in terms of penalization for added parameters, while the addition of the time-specific effects of $Vol_4$ does improve model predictions between the 6 and 24 w intervals. In some cases, the aforementioned regression models can be applied to ACL graft healing, human studies, and/or time points other than 6, 12, and 24 w. It is likely that ACL healing and graft ligamentization undergo similar biological processes such as cellular infiltration, neovascularization and collagen remodeling.[27,40] To this end, we did not find any differences in the tensile properties between ACL grafts and enhanced repair ACLs at 3, 6 or 12 months in Yucatan minipigs.[11,28] However, we have shown that combinations of histological characteristics (i.e., cellularity, collagen, vascularity) that predicted the tensile properties of the grafts or healing ACLs were different.[28]

Using non-invasive MR $T_2^*$ relaxometry to quantify collagen organization at acute (6 w), sub-acute (12 w) and chronic (24 w) stages of wound healing, we developed a 12-parameter multiple linear regression model to predict the in vivo structural properties of the ACL between 6 and 24 weeks in a preclinical model of ACL repair. In addition to the ACL sub-volume containing the most organized collagen, the sub-volume containing the least organized collagen and time-specific parameters were critical elements of the new regression models that will allow us to evaluate the functional status of the ACL repair in vivo, and with further development, may give surgeons a quantitative metric with which to develop and gauge return to sport criteria.

Example 14 References

1. Majewski, M, Susanne, H, Klaus, S. 2006. Epidemiology of athletic knee injuries: A 10-year study. Knee 13: 184-188.
2. Gianotti, S M, Marshall, S W, Hume, P A, Bunt, L. 2009. Incidence of anterior cruciate ligament injury and other knee ligament injuries: a national population-based study. Journal of Science and Medicine in Sport 12: 622-627.
3. Fisher, M B, Jung, H J, McMahon, P J, Woo, S L. 2010. Evaluation of bone tunnel placement for suture augmentation of an injured anterior cruciate ligament: effects on joint stability in a goat model. Journal of orthopaedic research: official publication of the Orthopaedic Research Society 28: 1373-1379.
4. Imhauser, C, Mauro, C, Choi, D, et al. 2013. Abnormal tibiofemoral contact stress and its association with altered kinematics after center-center anterior cruciate ligament reconstruction: an in vitro study. Am J Sports Med 41: 815-825.
5. McCarthy, M M, Tucker, S, Nguyen, J T, et al. 2013. Contact stress and kinematic analysis of all-epiphyseal and over-the-top pediatric reconstruction techniques for the anterior cruciate ligament. Am J Sports Med 41: 1330-1339.
6. Woo, S L, Kanamori, A, Zeminski, J, et al. 2002. The effectiveness of reconstruction of the anterior cruciate ligament with hamstrings and patellar tendon. The Journal of Bone and Joint Surgery 84-A: 907-914.
7. Sasaki, N, Farraro, K F, Kim, K E, Woo, S L. 2014. Biomechanical evaluation of the quadriceps tendon autograft for anterior cruciate ligament reconstruction: a cadaveric study. Am J Sports Med 42: 723-730.
8. Fleming, B C, Spindler, K P, Palmer, M P, et al. 2009. Collagen-platelet composites improve the biomechanical properties of healing anterior cruciate ligament grafts in a porcine model. Am J Sports Med 37: 1554-1563.
9. Joshi, S M, Mastrangelo, A N, Magarian, E M, et al. 2009. Collagen-platelet composite enhances biomechanical and histologic healing of the porcine anterior cruciate ligament. Am J Sports Med 37: 2401-2410.

10. Nguyen, D T, Geel, J, Schulze, M, et al. 2013. Healing of the goat anterior cruciate ligament after a new suture repair technique and bioscaffold treatment. Tissue Eng Part A 19: 2292-2299.
11. Vavken, P, Fleming, B C, Mastrangelo, A N, et al. 2012. Biomechanical outcomes after bioenhanced anterior cruciate ligament repair and anterior cruciate ligament reconstruction are equal in a porcine model. Arthroscopy 28: 672-680.
12. Vavken, P, Proffen, B, Peterson, C, et al. 2013. Effects of suture choice on biomechanics and physeal status after bioenhanced anterior cruciate ligament repair in skeletally immature patients: a large-animal study. Arthroscopy 29: 122-132.
13. Schwartz, H E, Matava, M J, Proch, F S, et al. 2006. The effect of gamma irradiation on anterior cruciate ligament allograft biomechanical and biochemical properties in the caprine model at time zero and at 6 months after surgery. The American Journal of Sports Medicine 34: 1747-1755.
14. Bedi, A, Kovacevic, D, Fox, A J, et al. 2010. Effect of early and delayed mechanical loading on tendon-to-bone healing after anterior cruciate ligament reconstruction. J Bone Joint Surg Am 92: 2387-2401.
15. Wu, B, Zhao, Z, Li, S, Sun, L. 2013. Preservation of remnant attachment improves graft healing in a rabbit model of anterior cruciate ligament reconstruction. Arthroscopy 29: 1362-1371.
16. Biercevicz, A M, Miranda, D L, Machan, J T, et al. 2013. In Situ, noninvasive, T2*-weighted MRI-derived parameters predict ex vivo structural properties of an anterior cruciate ligament reconstruction or bioenhanced primary repair in a porcine model. Am J Sports Med 41: 560-566.
17. Biercevicz, A M, Murray, M M, Walsh, E G, et al. 2014. T2* MR relaxometry and ligament volume are associated with the structural properties of the healing ACL. Journal of orthopaedic research: official publication of the Orthopaedic Research Society 32: 492-499.
18. Weiler, A, Peters, G, Maurer, J, et al. 2001. Biomechanical properties and vascularity of an anterior cruciate ligament graft can be predicted by contrast-enhanced magnetic resonance imaging. A two-year study in sheep. American Journal of Sports Medicine 29: 751-761.
19. Proffen, B L, McElfresh, M, Fleming, B C, Murray, M M. 2012. A comparative anatomical study of the human knee and six animal species. Knee 19: 493-499.
20. Xerogeanes, J W, Fox, R J, Takeda, Y, et al. 1998. A functional comparison of animal anterior cruciate ligament models to the human anterior cruciate ligament. Annals of Biomedical Engineering 26: 345-352.
21. Mueller, X M, Hendrick, T T, Jegger, D, et al. 2001. Are standard human coagulation tests suitable in pigs and calves during extracoporeal circulation? Artificial Organs 25: 579-584.
22. Kiapour, A M, Shalvoy, M R, Murray, M M, Fleming, B C. 2015. Validation of porcine knee as a sex-specific model to study human anterior cruciate ligament disorders. Clinical orthopaedics and related research 473: 639-650.
23. Deoni, S C, Williams, S C, Jezzard, P, et al. 2008. Standardized structural magnetic resonance imaging in multicentre studies using quantitative T1 and T2 imaging at 1.5 T. Neuroimage 40: 662-671.
24. McWalter, E J, Braun, H J, Keenan, K E, Gold, G E. 2012. Knee. In: Bydder, G. M., Fullerton, G. D., Young, I. R. editors, MRI of Tissues with Short T2s or T2*s, 1st ed. West Sussex, United Kingdom: John Wiley & Sons Ltd., pp. 325-338.
25. Williams, A, Qian, Y, Golla, S, Chu, C R. 2012. UTE-T2 mapping detects sub-clinical meniscus injury after anterior cruciate ligament tear. Osteoarthritis Cartilage 20: 486-494.
26. Biercevicz, A M, Proffen, B L, Murray, M M, et al. 2015. T2* relaxometry and volume predict semi-quantitative histological scoring of an ACL bridge-enhanced primary repair in a porcine model. Journal of orthopaedic research: official publication of the Orthopaedic Research Society 33: 1180-1187.
27. Arnoczky, S P, Warren, R F, Ashlock, M A. 1986. Replacement of the anterior cruciate ligament using a patellar tendon allograft. The Journal of Bone and Joint Surgery 68-A: 376-385.
28. Proffen, B L, Fleming, B C, Murray, M M. 2013. Histologic Predictors of Maximum Failure Loads Differ between the Healing ACL and ACL Grafts after 6 and 12 Months In Vivo. Orthop J Sports Med 1: 1-11.
29. Frank, C B, Hart, D A, Shrive, N G. 1999. Molecular biology and biomechanics of normal and healing ligaments—A review. Osteoarthritis Cartilage 7: 130-140.
30. Ramsey, F L, Schafer, D W. 2002. Strategies for variable selection. In: Crockett, C. editor, The statistical sleuth: a course in methods of data analysis, 2nd ed. Pracific Grove, Calif.: Druxbury, pp. 338-373.
31. Murray, M M, Fleming, B C. 2013. Use of a Bioactive Scaffold to Stimulate Anterior Cruciate Ligament Healing Also Minimizes Posttraumatic Osteoarthritis After Surgery. Am J Sports Med 41: 1762-1770.
32. Beveridge, J E, Walsh, E G, Murray, M M, Fleming, B C. 2017. Sensitivity of ACL volume and T2* relaxation time to magnetic resonance imaging scan conditions. J Biomech 56: 117-121.
33. Haacke, E M, Brown, R W, Thompson, M R, Venkatesan, R. 1999. Introductory Signal Acquisition Methods: Free Induction Decay, Spin Echoes, Inversion Recovery, and Spectroscopy. In, Magnetic resonance imaging: physical principles and sequence design, 1st ed. New York, N.Y.: John Wiley & Sons, pp. 113-136.
34. Biercevicz, A M, Walsh, E G, Murray, M M, et al. 2014. Improving the clinical efficiency of T2(*) mapping of ligament integrity. J Biomech 47: 2522-2525.
35. Murray, M M, Magarian, E, Zurakowski, D, Fleming, B C. 2010. Bone-to-bone fixation enhances functional healing of the porcine anterior cruciate ligament using a collagen-platelet composite. Arthroscopy 26: S49-57.
36. Hensler, D, Illingworth, K D, Musahl, V, et al. 2015. Does fibrin clot really enhance graft healing after double-bundle ACL reconstruction in a caprine model? Knee Surg Sports Traumatol Arthrosc 23: 669-679.
37. Li, H, Chen, J, Li, H, et al. 2016. MRI-based ACL graft maturity does not predict clinical and functional outcomes during the first year after ACL reconstruction. Knee Surg Sports Traumatol Arthrosc.
38. Li, H, Chen, S, Tao, H, et al. 2014. Correlation Analysis of Potential Factors Influencing Graft Maturity After Anterior Cruciate Ligament Reconstruction. Orthop J Sports Med 2: 1-7.
39. Lee, B I, Kim, B M, Kho, D H, et al. 2016. Does the tibial remnant of the anterior cruciate ligament promote ligamentization? Knee 23: 1133-1142.
40. Murray, M M, Martin, S D, Martin, T L, Spector, M. 2000. Histological changes in the human anterior cruciate ligament after rupture. The Journal of Bone and Joint Surgery 82-A: 1387-1397.

Example 15—Sensitivity of ACL Volume and $T_2$* Relaxation Time to Magnetic Resonance Imaging Scan Conditions Anterior cruciate ligament (ACL) volume and $T_2$* relaxation times from magnetic resonance (MR) images have been previously shown to predict the structural properties of healing ligaments. We investigated whether MR imaging scan resolution and condition (in vivo, in situ, or ex vivo) affected ACL volume and $T_2$* relaxation times in intact ligaments. ACLs of 14 pigs were imaged using a 3T scanner and a six-channel flexcoil using at least two of four possible scan conditions: (1) in vivo moderate resolution (n=14); (2) in vivo high resolution (n=7); (3) in situ high resolution acquired within 60 minutes of euthanasia (n=6); and (4) ex vivo high resolution following hind limb disarticulation and one freeze-thaw cycle (n=7). $T_2$* relaxation times were mapped to the ACL voxels. The total ACL volume was then divided into four sub-volumes ($Vol_{1-4}$) based on predetermined increasing ranges of $T_2$* times. ACL $T_2$* statistics (first quartile, median, and standard deviation (SD)) were computed. Scan resolution had no effect on the total ACL volume, but $Vol_1$ and first quartile $T_2$* times decreased with high resolution and in situ/ex vivo scan conditions. The most dramatic differences in $T_2$* summary statistics were between in vivo moderate and ex vivo high resolution scan conditions that included a freeze-thaw cycle: ACL $T_2$* SD increased by over 50% in 9 animals, and more than 90% in 4 animals. Our results indicated that $T_2$*-based prediction models to quantify in vivo structural properties of healing ligaments should be based on high resolution in vivo MR scan conditions.

Magnetic resonance (MR) imaging is a valuable tool to monitor soft tissue remodeling non-invasively. $T_2$* is a measure of MR signal relaxation that is related to the degree of free water bound by collagen (Helms, et al., 2008), with highly organized collagen structures yielding shorter $T_2$* relaxation times (Williams, et al., 2012). $T_2$* is particularly well suited for imaging ligament and tendon healing in vivo because collagen re-organization is of interest (Biercevicz, et al., 2015; Weiler, et al., 2001). We have previously demonstrated that a larger volume of the anterior cruciate ligament (ACL) containing short MR $T_2$* relaxation times predicts the ligament structural properties in a minipig model of bridge-enhanced ACL repair (Biercevicz, et al., 2014). In developing this MR technique, high resolution 512×512 matrix scans were collected in situ to determine the ACL $T_2$* relaxation times. ACL voxels were then binned into four sub-volumes based on increasing ranges of $T_2$* relaxation times established a priori to delineate portions of the ligament containing organized versus disorganized collagen. In some cases, using a more clinically relevant moderate resolution scan, such as a 384×384 matrix, might influence the distribution of $T_2$* relaxation times in the minipig model. Additionally, ex vivo scan conditions following a freeze-thaw cycle—if used to store limbs until convenient for pilot testing and/or sequence development (Chang, et al., 2014; Du, et al., 2012; Juras, et al., 2013)—might further influence $T_2$* relaxation times.

Whereas the binning of ACL voxels based on $T_2$* relaxation times is an approach that is independent of the range of values within the dataset, the first quartile is a statistical measure that indicates the threshold of the lowest 25% of $T_2$* relaxation times. Interpreted alongside the median, the first quartile also provides an indication of the spread of values in the dataset. In other words, the binned sub-volume describes how much of the ACL is composed of highly organized collagen (which can account for more than 25% of the total ligament volume), and the $T_2$* first quartile describes tissue quality and variation within the ACL and is dependent on the values contained within the dataset. Both volume and quality are central elements of our models to predict healing ACL structural properties (Biercevicz, et al., 2013; Biercevicz, et al., 2015; Biercevicz, et al., 2014). In order to extend the in situ-based prediction models to in vivo conditions, we sought to determine whether intact ACL total volume and $T_2$* relaxation times were sensitive to MR imaging scan conditions by: 1) determining the sensitivity of ACL volume and $T_2$* relaxation time to MR scan resolution, and 2) exploring whether ACL volume and $T_2$* relaxation times were different when measured in vivo, in situ or ex vivo after a freeze-thaw cycle in the minipig model.

Methods

Animals:

Intact ACLs of 14 skeletally mature (16.1±1.1 month old) Yucatan minipigs were imaged using a 3T scanner and a six-channel flexcoil (Prisma; Siemens, Erlangen, Germany). All animal procedures were approved by the Institutional Animal Care and Use Committee. Animals were sedated using telozol with xylazine, and then intubated and maintained under general isofluorane anesthesia during scanning.

MR Scan Conditions:

Table 4 shows a distribution of MRI scanning conditions that were investigated. As shown in Table 4, ACLs were scanned using at least two different MR scan conditions. The four conditions were: (1) in vivo "moderate resolution" matrix (n=14); (2) in vivo "high resolution" matrix (n=7); (3) in situ high resolution matrix acquired within 60 minutes of euthanasia (n=6); and (4) ex vivo high resolution matrix following hind limb disarticulation and one freeze-thaw cycle (n=7). All scans were 3D gradient multi-echo sequences, and shared the following parameters: FOV=160× 160 mm; ST/gap=0.8 mm/0 mm; TR=29 ms; FA=12°. The acquisition matrix of the moderate resolution scan was 384×384 (voxel size of 0.42×0.42×0.8 mm) with 6 echoes at TE=2.48, 6.86, 11.24, 15.62, 20.00 and 24.38 ms. The acquisition matrix of the high resolution scan was 512×512 (voxel size of 0.31×0.31×0.8 mm) and 4 echoes at TE=2.8, 7.88, 12.96 and 18.04 ms.

TABLE 4

Distribution of animals across the scanning conditions investigated.

| Animal # | In vivo 384 × 384 | In vivo 512 × 512 | In situ 512 × 512 | Ex vivo 512 × 512 |
|---|---|---|---|---|
| 1 | ✓ | | | ✓ |
| 2 | ✓ | | | ✓ |
| 3 | ✓ | | | ✓ |
| 4 | ✓ | | | ✓ |
| 5 | ✓ | | | ✓ |
| 6 | ✓ | | | ✓ |
| 7 | ✓ | | | ✓ |
| 8 | ✓ | ✓ | | |
| 9 | ✓ | ✓ | ✓ | |
| 10 | ✓ | ✓ | ✓ | |
| 11 | ✓ | ✓ | ✓ | |
| 12 | ✓ | ✓ | ✓ | |
| 13 | ✓ | ✓ | ✓ | |
| 14 | ✓ | ✓ | ✓ | |

Figure 23:
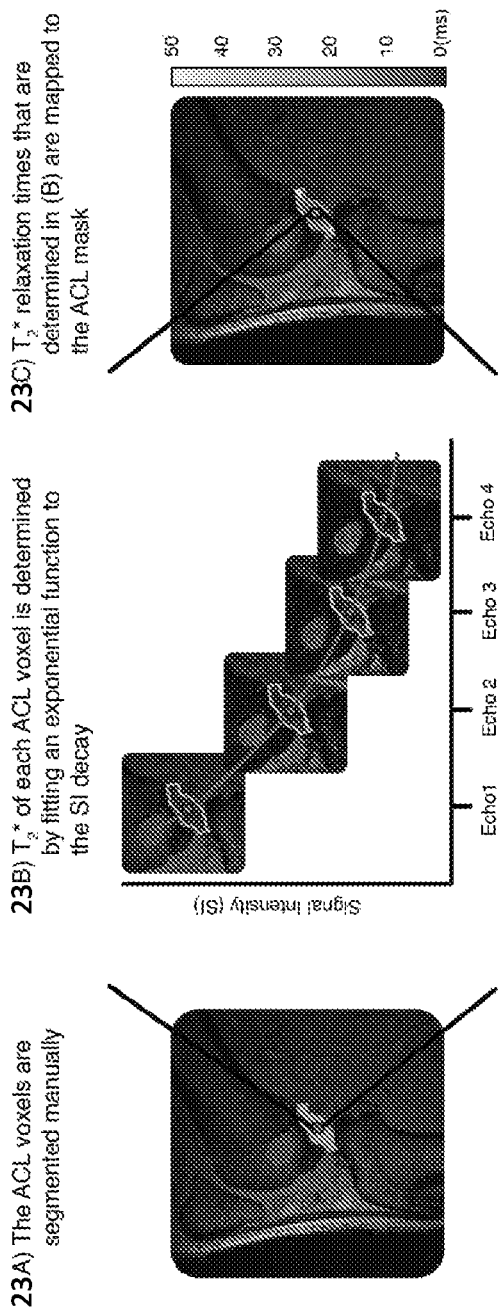
FIG. 23 shows images 23A, 23C and a plot 23B of signal intensity for various echoes. The image 23A is a single MR slice showing segmented ACL highlighted in blue. In image 23A, an ACL voxel is illustrated as a red square. The plot 23B shows signal intensity for various MRI echoes. In plot 23B, the segmented ACL is outlined in blue, and ACL voxels are illustrated as red squares. The image 23C is the image 23A but including an image map of ACL $T_2$* relaxation times. In image 23C, an ACL voxel is outlined with a square. For each ACL voxel (shown as a red square in image 23A and plot 23B, and a clear square in image 23C (not to scale for illustration purposes), a monoexponential function (Haacke, et al., 1999) is fitted to the MRI signal intensity decay associated with each echo.

$T_2$* Calculation:

ACLs were segmented manually (Mimics v16, Belgium) from the $T_2$* images by a single segmenter. $T_2$* relaxation times were then calculated by fitting an exponential decay function (Haacke, et al., 1999) to either the 4- or 6-echo sequence on a voxel-wise basis. FIG. 23 shows images 23A, 23C and a plot 23B of signal intensity for various echoes. The image 23A is a single MR slice showing segmented ACL highlighted in blue. In image 23A, an ACL voxel is illustrated as a red square. The plot 23B shows signal intensity for various MRI echoes. In plot 23B, the segmented ACL is outlined in blue and ACL voxels are illustrated as red squares. The image 23C is the image 23A but including an image map of ACL $T_2$* relaxation times. In image 23C, an ACL voxel is outlined with a square. For each ACL voxel (shown as a red square in image 23A and plot 23B, and a clear square in image KC, a monoexponential function (Haacke, et al., 1999) is fitted to the MRI signal intensity decay associated with each echo., as shown in image 23B. Residual $R^2$ values of the 4- and 6-echo $T_2$* functions were used to quantify goodness of fit between the 4- and 6-echo sequences. All calculations were performed using custom software within MATLAB® (v2015b, Natick, Mass.).

ACL Volume:

The ACL total volume was determined and it was then binned into four ranges of increasing $T_2$* relaxation times as previously reported (Biercevicz, et al., 2014): $Vol_1$=0-12.5 ms; $Vol_2$=12.6-25 ms; $Vol_3$=25.1-37.5 ms; $Vol_4$=37.6 ms-50 ms. In addition to ACL total volume, analyses focused on $Vol_1$ because this sub-volume contains voxels with the shortest $T_2$* relaxation times that are representative of more organized collagen and have stronger predictive power in estimating ACL structural properties.

Statistical Analyses:

ACL $T_2$* summary statistics (first quartile, median and standard deviation (SD)) were computed. Repeated measures ANOVA were used to test for significant differences in ACL total volume and $Vol_1$, where these measures were collected for three scan conditions (e.g., Subjects #9-14, shown in Table 4, n=6). Paired t-tests were used to evaluate differences between: (1) residual $R^2$ values of $T_2$* equation fits of the 6-echo and 4-echo in vivo scan protocols (e.g., Subjects #8-14, shown in Table 4, n=7;); (2) $T_2$* summary statistics of high resolution in vivo and in situ protocols (e.g., Subjects #9-14, shown in Table 4, n=6;); and (3) $T_2$* summary statistics of in vivo moderate resolution and ex vivo high resolution protocols (n=7; Subjects #1-7, Table 1). Paired t-tests were adjusted for multiple comparisons ($p \leq 0.017$) using the Šidák-Bonferroni method.

Results

Figure 24:
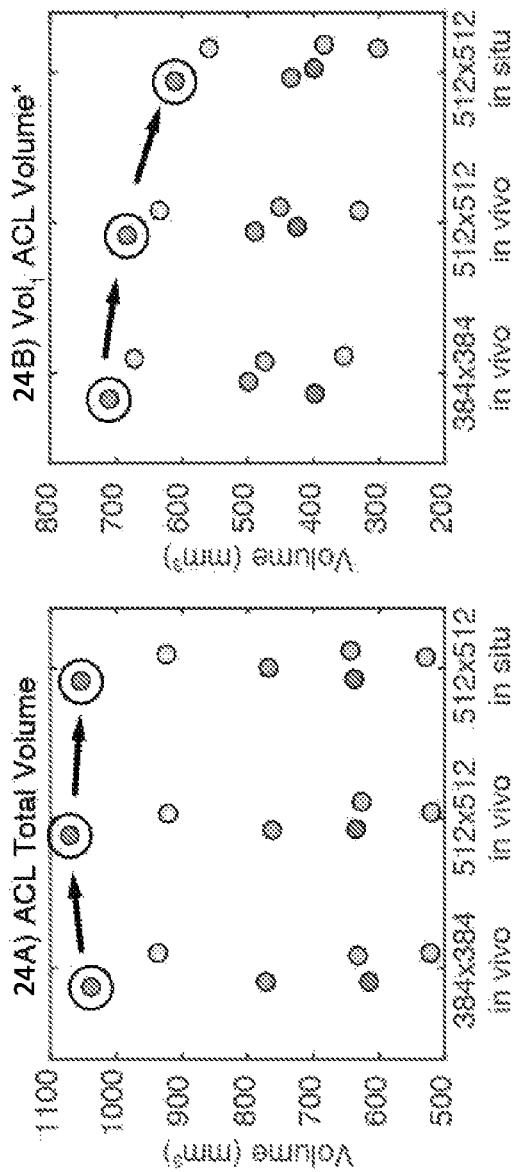
FIG. 24 is a set of plots 24A, 24B illustrating ACL volumes which were determined using various scanning analysis techniques. Plot LA shows total ACL volumes for a set of animals. Plot 24B shows a portion, or sub-volume ($Vol_1$), of total ACL volume, where $Vol_1$ corresponds to voxels with the shortest $T_2$* relaxation times. Markers in plots 24A, 24B are color-coded by animal to illustrate the within-subject consistency in segmented ACL volumes across scan conditions. Subject-specific color is the same in plots 24A, 24B. As an example, ACL Volume and $Vol_1$ values are circled for one subject, in blue. $Vol_1$ was significantly different across scan conditions, denoted by "*" (repeated measures ANOVA, n=6).

ACL Volume and Scan Condition:

FIG. 24 shows plots 24A, 24B illustrating ACL volumes for subjects #9-14, which were determined using the using the scanning conditions shown in Table 4. Scan resolution had no effect on the ACL total volume (p=0.3), as shown in image 24A. The mean coefficient of variation between the ACL total volume across in vivo and in situ scan protocols was 1%. However, $Vol_1$ decreased with increased scan resolution and in situ protocols (p=0.005), as shown in image 24B.

$T_2$* Equation Fit:

Mean residual $R^2$ values (±SD) of the 4-echo and 6-echo $T_2$* equation fits were 0.91±0.02 ms and 0.94±0.01 ms, respectively. In vivo high resolution 4-echo scan $R^2$ values were significantly less than the moderate resolution 6-echo residual $R^2$ values by 0.03 ms (−0.05, −0.02 ms; 95% confidence interval (CI)).

Figure 25:
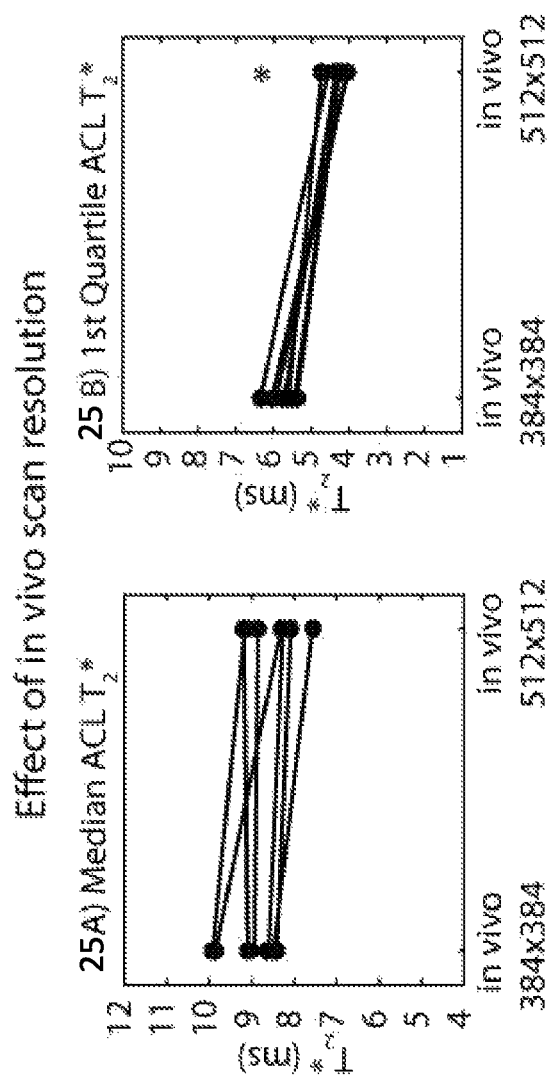
FIG. 25 is a set of plots 25A, 25B, where plot 25A shows Median ACL $T_2$* values and plot 25B shows $1^{st}$ quartile values. "*" indicates significant decrease in the quartile of lowest $T_2$* values (paired t-test, p≤0.05; n=7).

Effect of In Vivo Scan Resolution:

Median ACL $T_2$* relaxation times were not different between in vivo moderate and high resolution scans, as shown in Table 5 and FIG. 25. First quartile ACL $T_2$* relaxation times were lower for in vivo high resolution scans.

TABLE 5

Paired analyses of ACL $T_2$* summary statistics. $T_2$* summary statistics from animals #1-7 (n = 7) were used to test for differences between in vivo 384 × 384 scans and ex vivo 512 × 512 scans (column 4). Summary statistics from animals #8-14 (n = 7) were used to test for differences between in vivo scan resolutions (column 1). Summary statistics from animals #9-14 (n = 6) were used to test for differences between in vivo and situ protocols (columns 2-3). For paired analyses involving animals #8-14, alpha was adjusted to account for multiple comparisons. Significant differences are in bold.

|  | Effect of Scan Resolution In vivo 384 × 384 vs In vivo 512 × 512 | | Effect of In Vivo vs In Situ In vivo 512 × 512 vs In situ 512 × 512 | | Effect of Combining Change in Resolution and Scan Condition In vivo 384 × 384 vs In situ 512 × 512 | | Effect of a Freeze-Thaw Cycle In vivo 384 × 384 vs Ex vivo 512 × 512 | |
|---|---|---|---|---|---|---|---|---|
|  | Mean Difference (95% CI) | p-value | Mean Difference (95% CI) | p-value | Mean Difference (95% CI) | p-value | Mean Difference (95% CI) | p-value |
| Median $T_2$* (ms) | −0.6 (−1.1, −0.04) | p = 0.04 | 1.4 (1.0, 1.8) | p = 0.0002 | 0.8 (0.1, 1.6) | p = 0.067 | −0.8 (−2.1, 0.5) | p = 0.17 |
| $T_2$* Standard Deviation (ms) | 2.4 (1.5, 3.3) | p = 0.0007 | 1.6 (0.03, 3.1) | p = 0.05 | 3.8 (2.2, 5.3) | p = 0.0014 | 6.4 (4.8, 7.9) | p < 0.0001 |
| First Quartile $T_2$* (ms) | −1.5 (−1.9, −1.1) | p = 0.0002 | −0.4 (−0.8, −0.1) | p = 0.014 | −1.0 (−1.6, −0.5) | p = 0.004 | −2.4 (−3.1, −1.7) | p = 0.0002 |

Figure 26:
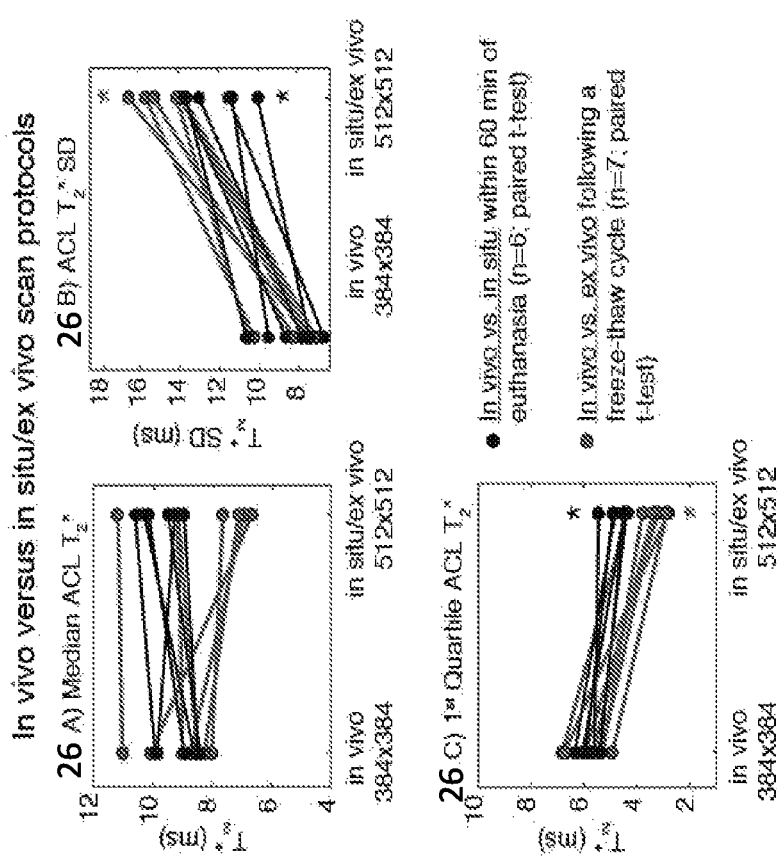
FIG. 26 is a set of plots 26A, 26B, 26C showing paired comparisons of $T_2$* summary statistics determined from moderate resolution in vivo scans, and high resolution scans collected either in situ (black line pairs) or ex vivo after a single freeze-thaw cycle (red line pairs). "*" indicates $T_2$* values were significantly different between scan conditions (p≤0.017).

Effect of In Vivo Versus In Situ/Ex Vivo Scan Protocols:

Compared to in vivo high resolution scans, in situ high resolution scan median and $1^{st}$ quartile ACL $T_2$* relaxation times were decreased but $T_2$* SD was not different, as shown in column 2 of Table 5. However, significant differences were observed between in vivo moderate resolution scans and ex vivo high resolution scans after a freeze-thaw cycle, as illustrated byred line pairs shown in plots 26B, 26C, shown in FIG. 26. ACL $T_2^*$ SD increased by over 50% in 9 animals, and more than 90% in 4 animals, as shown in Table 5 and in plot 26C.

Discussion

One purpose of this study was to determine whether the ACL total volume and $T_2^*$ relaxation times were sensitive to MR scan resolution and in vivo, in situ, and ex vivo scan conditions. The results suggest that scan resolution and scan condition influence ACL $T_2^*$ relaxation times, which in turn could affect the predictive models for ACL structural properties (Biercevicz, et al., 2014). Based on $T_2^*$ relaxation time standard deviations and first quartile values, the magnitude of differences between scan conditions investigated increased in the following order: In vivo high resolution scans versus in situ high resolution scans; In vivo moderate resolution versus in vivo high resolution scans; In vivo moderate resolution scans versus in situ high resolution scans; and In vivo moderate resolution scans versus ex vivo high resolution scans after a freeze-thaw cycle.

Figure 27:
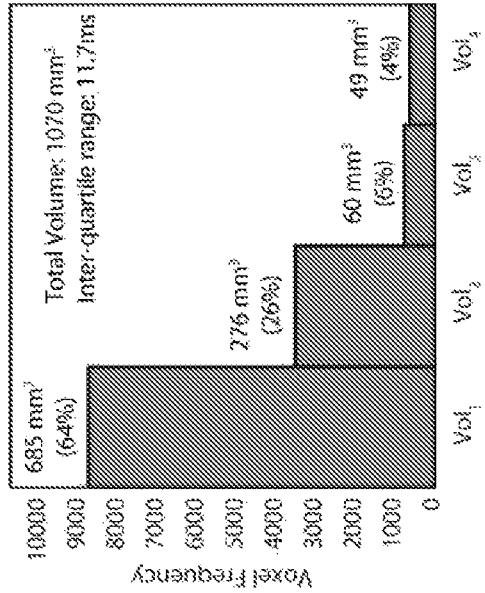
FIG. 27 is a set of plots 27A, 27B, where plot 27A shows voxel frequencies of various sub-volumes at a moderate scanning resolution matrix of 384×384, and plot 27B shows voxel frequencies of various sub-volumes at a higher scanning resolution matrix of 512×512.
Figure 27:
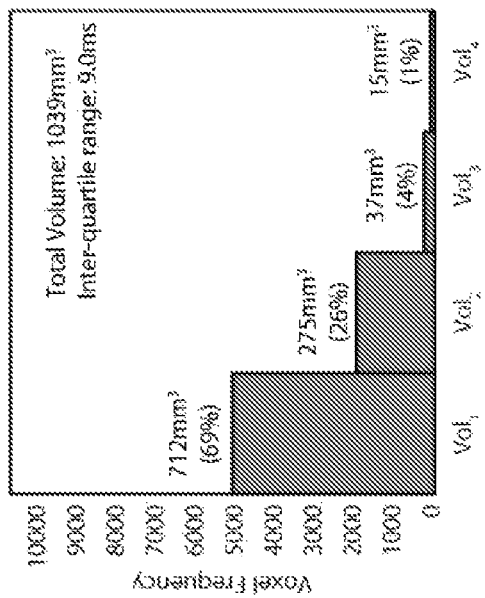
Figure 28:
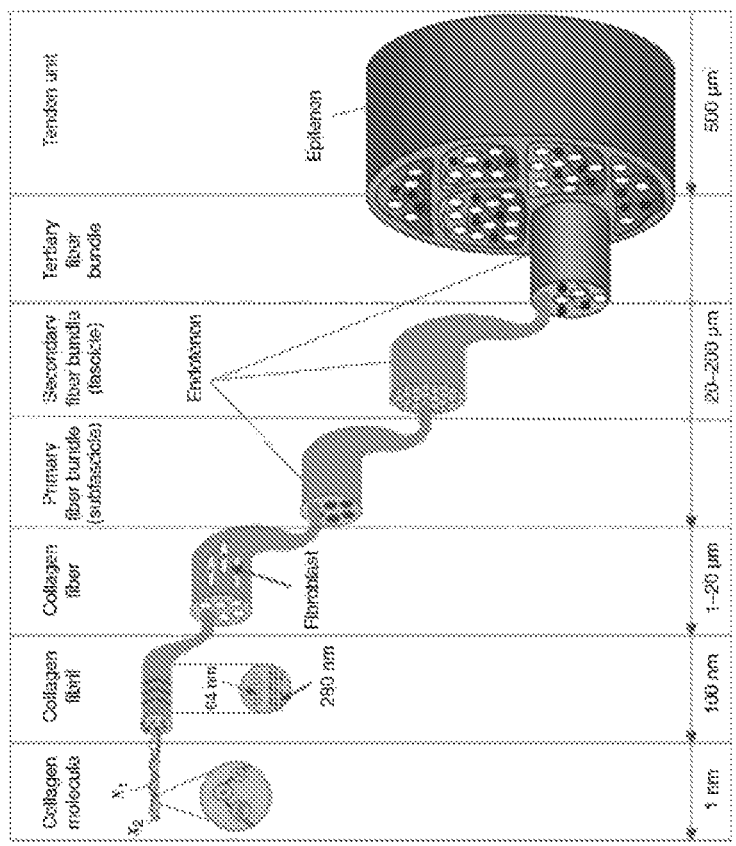
FIG. 28 is a hierarchical structure of a composite extracellular matrix structure of a ligament or tendon.

Whereas differences in ACL total volume depended largely on user segmentation reproducibility, $Vol_1$ was dependent on both segmentation and $T_2^*$ relaxation times. The decrease in $Vol_1$ suggests a redistribution of ACL sub-volumes that occurred with different MR scan conditions. A post-hoc investigation of $T_2^*$ inter-quartile ranges revealed that volume and scan condition (in vivo versus in situ, and moderate resolution versus high resolution) affected the distribution of $T_2^*$ relaxation times across the four bins. Compared to the in vivo moderate resolution condition, the in vivo high resolution scan increased the interquartile range of $T_2^*$ times by a mean of 2.3 ms. This finding suggests that the higher resolution scan condition resulted in a greater spread of $T_2^*$ relaxation times, particularly at higher $T_2^*$ values that correspond to $Vol_{3-4}$ sub-volumes. As an example, FIG. 27 shows the difference in binned ACL sub-volumes for the same subject circled in FIG. 24 and illustrates the shift in the number of voxels assigned to $Vol_3$ and $Vol_4$. Although the magnitude of the shift in voxels assigned to these sub-volumes is small in healthy ACLs, the difference in distribution may be more consequential in repaired ACLs where the number of voxels assigned to these sub-volumes would, theoretically, be greater during the early healing phases when collagen fibers are initially less organized (Frank, et al., 1999; Proffen, et al., 2013).

Greater partial volume effects that average high and low $T_2^*$ relaxation times from adjacent tissue regions may explain the smaller inter-quartile range and higher $T_2^*$ first quartile values associated with the moderate resolution scans shown in plot 25B, shown in FIG. 25, and the $Vol_1$ sub-volumes in FIG. 24. Thus moderate scan resolutions may mask localized reductions in $T_2^*$ relaxation times and truncate the dynamic range of ACL $T_2^*$ values that are detectable using higher resolution scans, both of which may be important for monitoring ligament remodeling in vivo (Biercevicz, et al., 2014; Weiler, et al., 2001). Despite these limitations, the differences in binned voxel sub-volumes as a percentage of total ligament volume between moderate and high resolution scans shown in FIG. 24 were ≤5% across the four sub-volumes in healthy ACL, which suggest that 384× 384 is an acceptable level of resolution, but is not ideal.

To investigate the extent that $T_2^*$ relaxation times were sensitive to the more clinically applicable scan conditions versus the conditions that we have used previously in our research (Biercevicz, et al., 2015; Biercevicz, et al., 2014), $T_2^*$ relaxation times derived from in vivo 384×384 matrix resolution were compared to those derived from in situ 512×512 matrix resolution scan conditions. Scanning ACLs at high resolution in situ within 60 minutes of euthanasia led to decreased and more variable $T_2^*$ relaxation times compared to in vivo moderate resolution scans. Whereas whole-ligament median $T_2^*$ relaxation times were not different (e.g., plot 25A, shown in FIG. 25), first quartile values decreased (e.g., plot 25B, shown in FIG. 25) and $T_2^*$ standard deviation increased significantly (black line pairs in plot 26B, shown in FIG. 26. We believe that these results reflect rapid localized changes in $T_2^*$ characteristics postmortem, and may be the result of decreased but variable tissue temperature (Petren-Mallmin, et al., 1993).

The combination of increasing scan resolution coupled with greater variation in tissue temperature with ex vivo scan conditions after a freeze-thaw cycle resulted in significant, and likely clinically relevant (up to 90%), increases in $T_2^*$ standard deviation and decreases in first quartile $T_2^*$ values, but not median, $T_2^*$ relaxation times. These results suggest that the absolute $T_2^*$ relaxation times acquired ex vivo are likely lower and more variable than values obtained in vivo at a moderate scan resolution. Therefore model equations for predicting ligament structural properties using ex vivo scans obtained after a freeze-thaw cycle may not reflect in vivo conditions accurately given that the prediction models are based on the distribution of ACL $T_2^*$ relaxation times.

Repeated measures of ACL volume and paired analyses of $T_2^*$ summary statistics demonstrated significant differences in these outcome measures as a result of different scan resolutions and conditions. The approach we chose parallels clinical protocols for this model. The consistency in ACL total volume between in vivo and in situ scans that were acquired after subjects were removed and then repositioned in the scanner 60 minutes after euthanasia (without limb disarticulation) supports our view that positioning had little effect on our final outcome measures. Finally, the number of echoes used in the exponential decay model in determining $T_2^*$ relaxation times was different between moderate and high resolution scans. For higher resolution scans, the number of echoes that could be collected was reduced to accommodate the inherent limitations of our scanner. The difference in mean residual $R^2$ values between the 4- and 6-echo exponential decay function fit was two orders of magnitude smaller than the resolution of our system (2.8 ms), confirming that any differences in $T_2^*$ relaxation times due to the number of echoes used are negligible.

In summary, the MR scan resolutions tested had little effect on ACL total volume but truncated the dynamic range of $T_2^*$ values, which may mask localized reductions in $T_2^*$ relaxation times, which are important for monitoring ligament remodeling in vivo. Scanning ex vivo at a high resolution following one freeze-thaw cycle amplified the differences in $T_2^*$ relaxation times associated with scan resolution alone, and resulted in more variable $T_2^*$ times within the ACL. Therefore, prediction models to quantify in vivo ACL structural properties longitudinally can be based on high resolution in vivo MR scan conditions.

Example 15 References

Biercevicz, A. M., Miranda, D. L., Machan, J. T., Murray, M. M. and Fleming, B. C., 2013. In Situ, noninvasive, T2*-weighted MRI-derived parameters predict ex vivo structural properties of an anterior cruciate ligament reconstruction or bioenhanced primary repair in a porcine model. Am J Sports Med 41, 560-566.

Biercevicz, A. M., Proffen, B. L., Murray, M. M., Walsh, E. G. and Fleming, B. C., 2015. T2* relaxometry and volume predict semi-quantitative histological scoring of an ACL bridge-enhanced primary repair in a porcine model. J Orthop Res 33, 1180-1187.

Biercevicz, A. M., Murray, M. M., Walsh, E. G., Miranda, D. L., Machan, J. T. and Fleming, B. C., 2014. T2* MR relaxometry and ligament volume are associated with the structural properties of the healing ACL. J Orthop Res 32, 492-499.

Chang, E. Y., Bae, W. C., Statum, S., Du, J. and Chung, C. B., 2014. Effects of repetitive freeze-thawing cycles on T2 and T2 of the Achilles tendon. Eur J Radiol 83, 349-353.

Du, J., Diaz, E., Carl, M., Bae, W., Chung, C. B. and Bydder, G. M., 2012. Ultrashort echo time imaging with bicomponent analysis. Magn Reson Med 67, 645-649.

Frank, C. B., Hart, D. A. and Shrive, N. G., 1999. Molecular biology and biomechanics of normal and healing ligaments—A review. Osteoarthritis Cartilage 7, 130-140.

Haacke, E. M., Brown, R. W., Thompson, M. R. and Venkatesan, R., 1999. Magnetic resonance imaging: physical principles and sequence design. Journal Helms, C. A., Major, N. M., Anderson, M. W., Kaplan, P. and Dussault, R., 2008. Musculoskeletal MRI. Journal Juras, V., Apprich, S., Pressl, C., Zbyn, S., Szomolanyi, P., Domayer, S., Hofstaetter, J. G. and Trattnig, S., 2013. Histological correlation of 7 T multi-parametric MRI performed in ex-vivo Achilles tendon. Eur J Radiol 82, 740-744.

Petren-Mallmin, Ericsson, A., Rausching, W. and Hemmingsson, A., 1993. The effect of temperature on MR relaxation times and signal intensities for human tissues. MAGMA 1, 176-184.

Proffen, B. L., Fleming, B. C. and Murray, M. M., 2013. Histologic Predictors of Maximum Failure Loads Differ between the Healing ACL and ACL Grafts after 6 and 12 Months In Vivo. Orthop J Sports Med 1, 1-11.

Weiler, A., Peters, G., Maurer, J., Unterhauser, F. N. and Sudkamp, N. P., 2001. Biomechanical properties and vascularity of an anterior cruciate ligament graft can be predicted by contrast-enhanced magnetic resonance imaging. A two-year study in sheep. American Journal of Sports Medicine 29, 751-761.

Williams, A., Qian, Y., Golla, S. and Chu, C. R., 2012. UTE-T2 mapping detects sub-clinical meniscus injury after anterior cruciate ligament tear. Osteoarthritis Cartilage. 20, 486-494. doi: 410.1016/j.joca.2012.1001.1009. Epub 2012 January 1018.

Example 16—Emerging Techniques for Tendon and Ligament MRI

Ligaments and tendons are dense connective tissues characterized by an organized structure of parallel, aligned collagen fibers. Normal (uninjured) tendon and ligament have proven to be challenging to image using conventional MRI approaches, owing to their short $T_2$ and low signal intensity. Acute or chronic injury to these tissues frequently results in disorganization and disruption of the fiber bundles as well as alterations in extracellular matrix composition; these changes, which compromise mechanical function of the tendon or ligament, can be readily detected using MR imaging. Recent studies using $T_2^*$ mapping have provided valuable insight into tissue regional structural organization and functional integrity. More advanced methods for imaging ligament and tendon, such as ultrashort echo time (UTE) and diffusion tensor imaging (DTI), are under development and may significantly advance our ability to utilize even shorter echo times or to directly image the fiber structure of intact, injured, repaired, or surgically reconstructed tissues.

Tendon & Ligament Structure, Function, Injury, and Healing

Tendons and ligaments are dense, fibrous connective tissues composed primarily of type I collagen (~80% of dry weight) and water (~60% of wet weight), along with other collagens, proteoglycans, and fibroblasts (1-3). The primary function of these tissues is to facilitate transmission of tensile loads from muscle to bone (tendon) or from bone to bone (ligament). FIG. 27 shows a hierarchical structure 2700 of a composite extracellular matrix structure of a ligament or tendon. As shown in FIG. 27, collagen molecules are organized in a cross-linked triple helix structure with water molecules bridging the helical strands. The hierarchical, composite extracellular matrix structure 2700 is characterized by a predominantly parallel arrangement of collagen fibers (1, 4, 5). As dictated by the fibrous structure, the biomechanical properties of tendon and ligament are highly anisotropic (i.e., direction-dependent). The high tensile strength in the longitudinal (fiber-aligned) direction is one to two orders of magnitude larger than that measured in the transverse direction (6). The structure and composition of ligaments and tendons therefore influence their appearance on MR imaging (7).

While normal ligaments and tendons have an organized structure of parallel, aligned collagen fibers, their structure can change significantly with injury or overuse. Acute injuries, including tears of the anterior cruciate ligament (ACL) and rotator cuff (RC) tendon, can result in complete disruption of the fiber bundles and/or fiber disorganization in the traumatized tissue. In addition, aging and overuse injuries can result in collagen fiber disorganization, disruption, hypercellularity, neovascularization, fatty infiltration, and the accumulation of glycosaminoglycans (8, 9). These changes alter the ability of the tendon or ligament to function (10), and can be readily detected using MR imaging.

MR imaging can be used to detect the compositional, structural and biomechanical changes that occur with tendon and ligament healing. Soft tissue healing begins with the formation of a provisional scaffold (i.e., blood clot) at the injury site (11). Following acute injury, extra-articular ligaments and tendons, such as the MCL or Achilles tendon, heal naturally via formation of a stable blood clot at the wound site. However, intra-articular ligaments and tendons, such as the ACL or RC tendons, do not heal naturally as enzymes in synovial fluid break down the formation of the fibrin clot (11). Surgical interventions to repair or reconstruct these ligaments are typically required and the outcomes can be less than ideal. Ongoing tissue engineering and regenerative strategies seek to augment the healing response of ligaments and tendons (12, 13). Successful healing of ligaments and tendons can involve three phases: 1) an inflammatory phase, 2) a revascularization/cell proliferation phase, and 3) remodeling/maturation phase (14). The inflammatory phase, which typically lasts a few days, involves the formation of the blood clot, the release of inflammatory cytokines and early fibroblast infiltration. The proliferative phase, which typically lasts a few weeks, is associated with continued fibroblast infiltration and cell proliferation, collagen deposition and neurovascular infiltration. The remodeling/maturation phase, which lasts months to years, facilitates continued remodeling of the collagen fibers and neurovascular structures. Throughout all three healing phases, the water content of the healing tissue changes and the new fibers in the scar tissue, which were randomly oriented at the beginning of the healing process, become more aligned with the native tissue, and these alterations can be detected with MR imaging. As in vivo studies are required to better understand the healing process and to develop and test new therapeutic strategies, methods to non-invasively measure structural, biochemical and biomechanical changes of healing and/or degenerating ligaments and tendons are essential for translation of new repair strategies.

MR imaging constitutes a non-invasive tool to visualize and quantify healing and/or degeneration in ligament and tendon tissues (15, 16). With conventional imaging, ligaments and tendons exhibit low signal intensity and hence appear dark. The interactions between the collagen and water molecules (i.e., residual dipolar coupling, susceptibility anisotropy and bulk magnetic susceptibility) is restricted, which in turn causes the T2 relaxation times of normal tendon (~1-2 ms at $B_0$=3 T) and ligament (~3-10 ms at $B_0$=3 T) to be relatively short (7). MR imaging can be used for the assessment of ligament and tendon healing and degeneration from a tissue engineering perspective. Recent advances in MR imaging are directed at measuring the biochemical and biomechanical changes accompanying disease and treatment.

MR Imaging Studies of Tendon and Ligament Healing

Traditional research methods to assess ligament and tendon healing typically include histology and/or biomechanical testing. Semi-quantitative histological scoring systems, such as the Ligament Maturity Index, provide a cumulative assessment of different histologic healing parameters including collagen organization, vascular content and cellular structural parameters (17). Other objective measures include evaluations of fiber size, orientation, cross-linking, fiber density and cell counts (17-21). Biomechanical testing of repaired ligaments and tendons are also commonly performed to assess healing as the structural (e.g., failure load, linear stiffness) and material properties (e.g. failure stress, tangent modulus) improve over time with successful healing (22-24). While these biomechanical and histological parameters serve as excellent proxies for soft tissue healing, they require biopsy or post-mortem tissue harvest, and therefore are only useful for pre-clinical animal studies and not clinical studies. Unfortunately, traditional clinical, functional and patient-oriented outcomes, which are commonly used to compare treatments in clinical trials, do not provide a direct assessment of the healing tissue and only focus on the functionality of the entire joint (22, 25). Other structures, such as the meniscus in the case of an ACL injury (26), may compensate for the deficiencies of the healing ACL. Reliable data from traditional clinical, functional and patient-oriented outcomes also require high sample sizes due to their high variability across patients. Therefore, specific non-destructive, non-invasive and quantitative methods to evaluate healing can be desirable for pre-clinical animal work (to evaluate healing longitudinally to minimize variability and the number of animals required) and for clinical trials. MR imaging constitutes one such approach.

The utility of MR imaging for evaluation of tendon and ligament healing has been previously demonstrated (27-29), and MRI has been widely used to measure the geometry and vascularity of ligaments and tendons (27, 30-32). Signal intensity (i.e., gray scale), a MR parameter shown to be a function of tissue type and water content, has been clinically used to evaluate ACL graft maturity following ACL reconstruction surgery (33-43), though validation of the method in humans has not yet been performed. Signal intensity measures have also been used to evaluate the mechanical properties of the patellar tendon in response to ibuprofen and acetaminophen treatment (44). While the signal intensity of normal healthy tendon and ligament is low, the signal intensity of an injured and/or healing ligament is greater than that of uninjured tissues and can be readily detected. In clinical studies, signal intensity has been evaluated via subjective clinician graded scores or direct quantitative assessment of the gray scale value identified within the structure of interest.

Justification for using signal intensity as a surrogate for ACL graft maturation has been supported by animal studies (24, 45, 46). Using an ovine model, the signal-to-noise quotient (normalized signal intensity) from a mid-substance slice of a $T_1$-weighed image of an ACL reconstructed graft was determined (24). The signal-to-noise quotient (SNQ);

$$SNQ=(SI_{(graft)}-SI_{(PCL)})\div(SI_{(Background)}) \quad (I)$$

where $SI_{(graft)}$ was the signal intensity of the ACL graft, $SI_{(PCL)}$ was the signal intensity of the posterior cruciate ligament (assumed to be normal ligament tissue), and $SI_{(Background)}$ was the signal intensity of the background, proved to be inversely correlated to the failure properties of the graft, findings that were also supported by qualitative histology and immunohistochemistry (24). A measurement tool to quantify healing that considers both the amount and the quality of the tissue would likely improve the predictive capabilities of the method for assessing biomechanical performance, as both of these parameters dictate the failure properties of the healing tissue.

Figure 29:
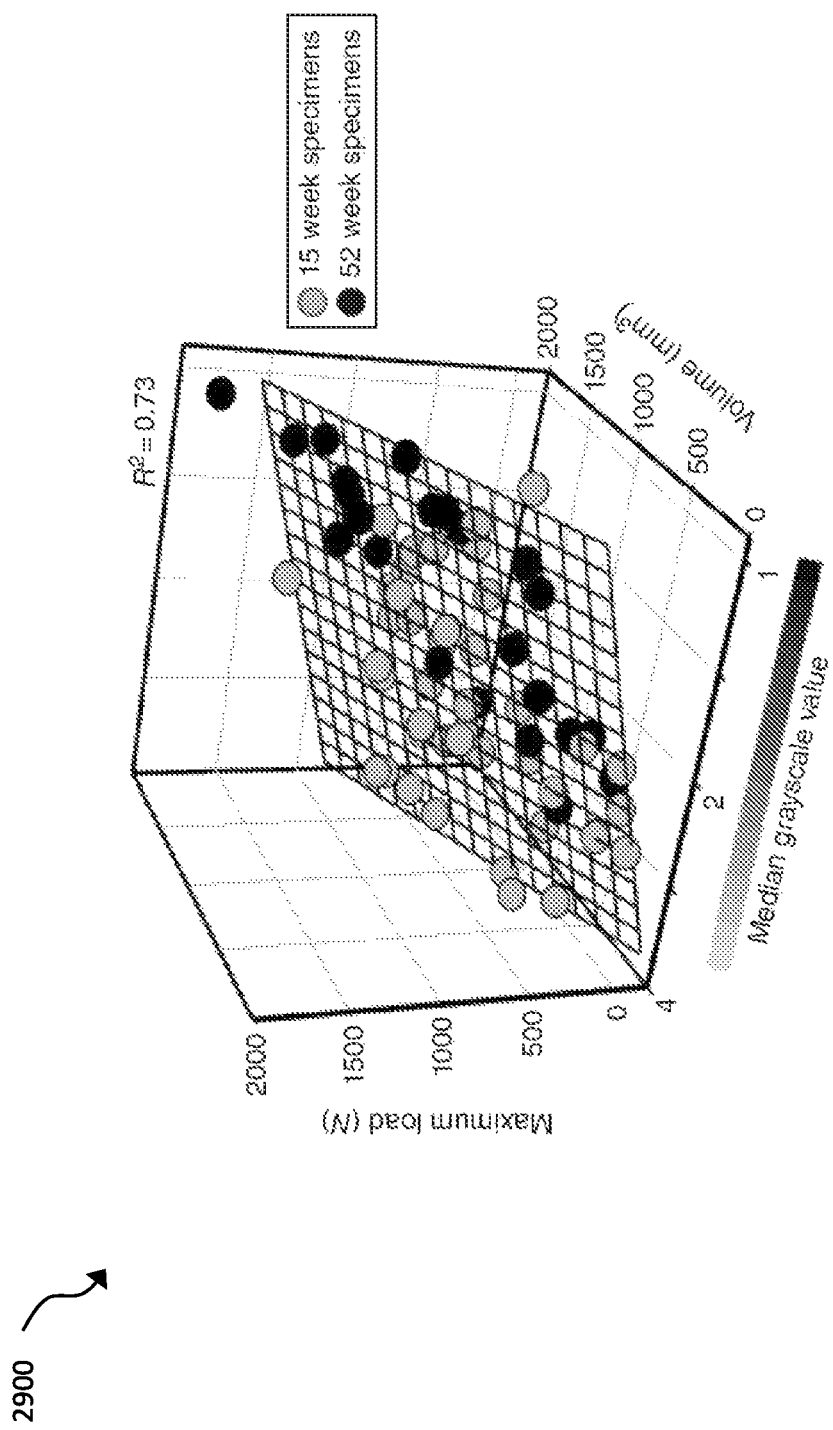
FIG. 29 is a reproduction of FIG. 4 and includes a plot showing maximum failure loads and volumes for a set of specimens evaluated at 15 weeks following ACL surgery, and another set of specimens evaluated at 52 weeks following ACL surgery.

A porcine study recently validated that MR-derived measures of ligament volume (a measure representing the amount of tissue) and signal intensity (a surrogate for tissue quality) were significant predictors of ligament integrity 15 and 52 weeks following ACL surgery (46). The ACL was manually segmented from the image stack from a $T_2$*-weighted 3D-CISS sequence (TR/TE/FA, 12.9/6.5/35°; FOV, 160 mm; matrix 512×512, slice length/gap, 0.8 mm/0; avg 1), which was selected because it accommodated the relatively small size of the ACL and produced high contrast between the soft tissues and joint fluid. The intra-articular ligament volume and the grayscale values for each pixel in that ligament volume were established. The ligament volume predicted the graft structural properties ($R^2$=0.56, 0.56, 0.49, respectively, for maximum load, yield load, and linear stiffness). The median grayscale values also predicted the structural properties of the ACL ($R^2$=0.42, 0.37, 0.40, respectively). However, the combination of these two parameters, which proved to be independent, significantly improved these predictions ($R^2$=0.73, 0.72, 0.68, respectively) in a multiple regression model (FIG. 29).

A subsequent clinical study demonstrated that the MR image-derived parameters of graft volume and signal intensity were highly correlated with commonly used clinical (e.g., antero-posterior knee laxity), functional (e.g., 1-leg hop test) and patient-oriented (Knee Injury Osteoarthritis Score) outcome measures five years after ACL reconstruction (25). A 3D-$T_1$-weighted FLASH sequence was used. It was determined that the combination of graft volume and signal intensity was able to predict the 1-leg hop for distance ($R^2$=0.63), AP knee laxity ($R^2$=0.43), and the KOOS Sports Score ($R^2$=0.61) after 5 years. These results align with the previous studies in which the biomechanical properties of the graft (e.g., linear stiffness) were predicted by a linear combination of these two variables (46). Similar MR prediction models based on signal intensity and/or graft volume were also highly correlated to histological parameters of ACL healing in animal models (24, 47, 48). These results demonstrated that the MR-derived parameters related to the graft structural properties are associated with clinical, functional and patient-oriented outcomes (25), and begin to link the prediction models from animals to humans.

While the initial studies utilizing signal intensity to evaluate ligament and tendon healing show promise both in clinical and animal studies, there remain significant limitations with the sensitivity and normalization of gray scale values between images and MR facilities that must be considered. MR images are typically scaled for display according to the brightest pixel or highest signal intensity in the image. Thus, a particular gray scale value on one image does not necessarily match that of another image. While normalization to bone or another uninjured ligament (e.g., the PCL) can be performed to minimize this concern (24, 46), this is far from ideal due to variations in noise levels between tissues and possible confounding effects of the injured ligament or tendon on adjacent tissues. Because ligaments and tendons have low signal intensities, small changes in signal intensity of these soft tissue due to healing or degeneration on an image scaled to the highest signal intensity may make the measures unreliable and/or less sensitive to detect minor changes. Furthermore, signal intensity is dependent on the image acquisition parameters, magnet strength and scanner manufacturer, rendering the predictions to be protocol, magnet and therefore institution specific (49), a problem that is particularly burdensome if one desires to use signal intensity as an outcome in multi-center trials. Unfortunately, signal intensity is not a fundamental property of the tissue.

While conventional MR provides adequate soft tissue contrast and high spatial resolution for healing ligaments and tendons, there remains uncertainty regarding its ability to resolve and delineate low grade tendon and ligament injuries (e.g., sprains) and the effects of subsequent treatments. Specifically, elevated MR signal intensity is suggestive of tissue-level alterations which may include increased water content, vascularity, inflammation, degeneration, and/or partial matrix disruption (50, 51). Hence, elucidating these potential abnormalities using a qualitative measure such as signal intensity (a standard means of conventional MR assessment) remains a challenge.

$T_2$ and $T_2^*$ relaxometry are frequently used to standardize MR parameters of soft tissues (52-54). $T_2$ and $T_2^*$ relaxation times are inherent tissue properties that reflect specific tissue characteristics and are much less sensitive to image acquisition parameters than conventional signal intensity data (49). Due to a low free water content and highly organized fibrous structure, normal ligament typically produces low signal intensity in $T_2$ and $T_2^*$-weighted images. $T_2$ and $T_2^*$ relaxation times have been shown to correlate with the level of tissue organization (55, 56) and are well suited for imaging highly organized collagenous structures (21, 55-57). In the event of rupture, a local increase in free water produces an increase in $T_2$ (58). This disorganization also results in $T_2$ values that vary with the orientation of the ligament within the main magnetic field of the scanner (59, 60). $T_2$ relaxation time is sensitive to alterations in the composition and structure of articular cartilage, and is commonly used for that purpose (52). In a clinical study the mean $T_2$ values for patients with confirmed tendon tears were significantly greater than those in patients with tendinosis or asymptomatic controls. However, no differences were found between the tendinosis and control groups. However, the echo times (TE) are too long to be feasible for tendon and ligament with $T_2$ mapping.

Figure 30:
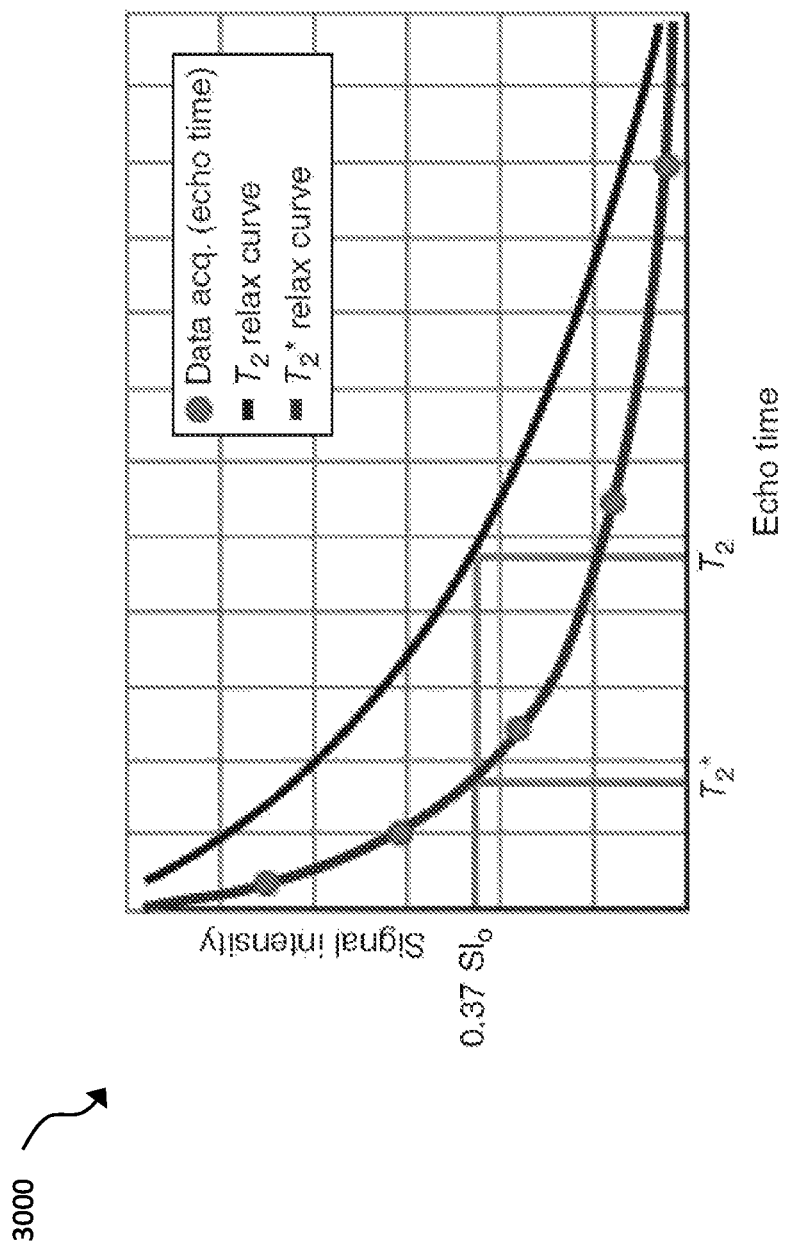
FIG. 30 is a plot showing theoretical relaxation day curves fit to signal intensity (SI) at varying echo times (TEs). Note the faster decay of $T_2$* in comparison to $T_2$ relaxation. This allows $T_2$* to capture more organized tissues with shorter relaxation times. (Adapted with permission from Chavhan et al. (55)).

$T_2^*$ is similar to $T_2$ but utilizes shorter echo times, giving $T_2^*$ the ability to better characterize ligament and tendon tissues. Therefore, $T_2^*$ mapping may provide a more universal predictive model of graft healing than either $T_2$ mapping or signal intensity at a fixed TE. Currently a voxel-wise, multi-echo least squares fit is the gold standard to create $T_2^*$ maps (61);

$$SI_{TE} = M_0 e^{\frac{-TE}{T_2^*}} + DC \qquad (2)$$

where $SI_{TE}$ are the voxel specific signal intensities for the various echo times (TE) used. The three fit parameters are $M_o$ (equilibrium magnetization), $T_2^*$ and the DC offset (DC). In general, increasing the number of echo times used in the determination of $T_2^*$ can result in a better estimate of $T_2^*$ (FIG. 30).

$T_2^*$ reflects $T_2$ relaxation as well as the effects of magnetic susceptibility gradients at both a macroscopic and microscopic level. It has been shown that the magnetic susceptibility of ligaments varies with water content (62). Collagen has a small diamagnetic susceptibility (63-65) that differs from that of water with collagen (with restricted diffusion scale of 2.3 µm) having susceptibility of −6.24× $10^{-6}$ SI and pure water having susceptibility of −9.05×$10^{-6}$ SI (56). Water interactions with collagen (residual dipolar coupling, susceptibility anisotropy and bulk magnetic susceptibility) account for the short $T_2^*$ in ligaments such that variations in collagen integrity can be visualized by quantifying $T_2^*$ (55). As noted above, images are scaled for display according to the highest pixel intensity while ligaments typically have low signal intensity, making the assessment of small signal differences somewhat difficult to detect. By correlating tissue condition with $T_2^*$, subjectivity becomes less of a factor in assessing ligament integrity. Unfortunately, $T_2^*$ is affected by static field inhomogeneity. However, use of $B_0$ field mapping can generate $T_2^*$ map corrections that compensate for large-scale inhomogeneity effects (66, 67). Indices for ligament integrity based on $T_2^*$ can be developed for standard clinical field strengths and can serve as a useful clinical tool.

In a recent study using the minipig model, $T_2^*$ relaxation time was able to predict the structural properties of a healing anterior cruciate ligament (54), as well as histological change in the tissue over time (47). Using a minipig model, unilateral ACL transections were performed followed by bridge-enhanced ACL repair (22) or natural healing without repair (54). The operated knees were harvested 12 months post-op and high-resolution MR images were immediately collected using a $T_1$-weighted gradient echo 3D-FLASH sequence, (TR/TE/FA, 25/7.36 & 15.24/12°; FOV, 140 mm; matrix 512×512, slice length/gap, 0.85 mm/0; avg 1 at 3 T). $T_2^*$ maps were created using the signal intensity relationship for two echo times (61);

$$T_2^* = \left[ \frac{\ln SI_1 - \ln SI_2}{TE_2 - TE_1} \right]^{-1} \qquad (3)$$

Figure 31:
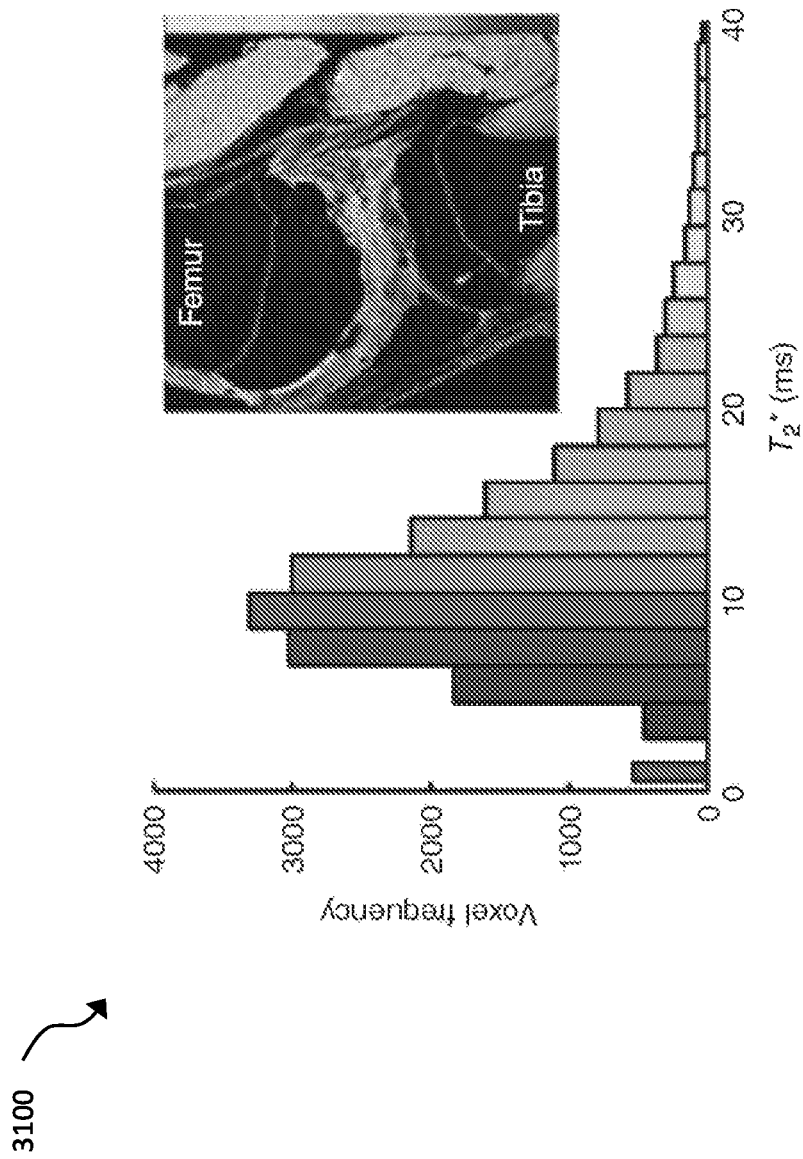
FIG. 31 is a reproduction of FIG. 5 and includes a histogram showing a voxel frequency distribution of $T_2$* within a healing ligament (Adapted with permission from Biercevicz et al. (54)), and an example MR image of a porcine ACL.
Figure 32:
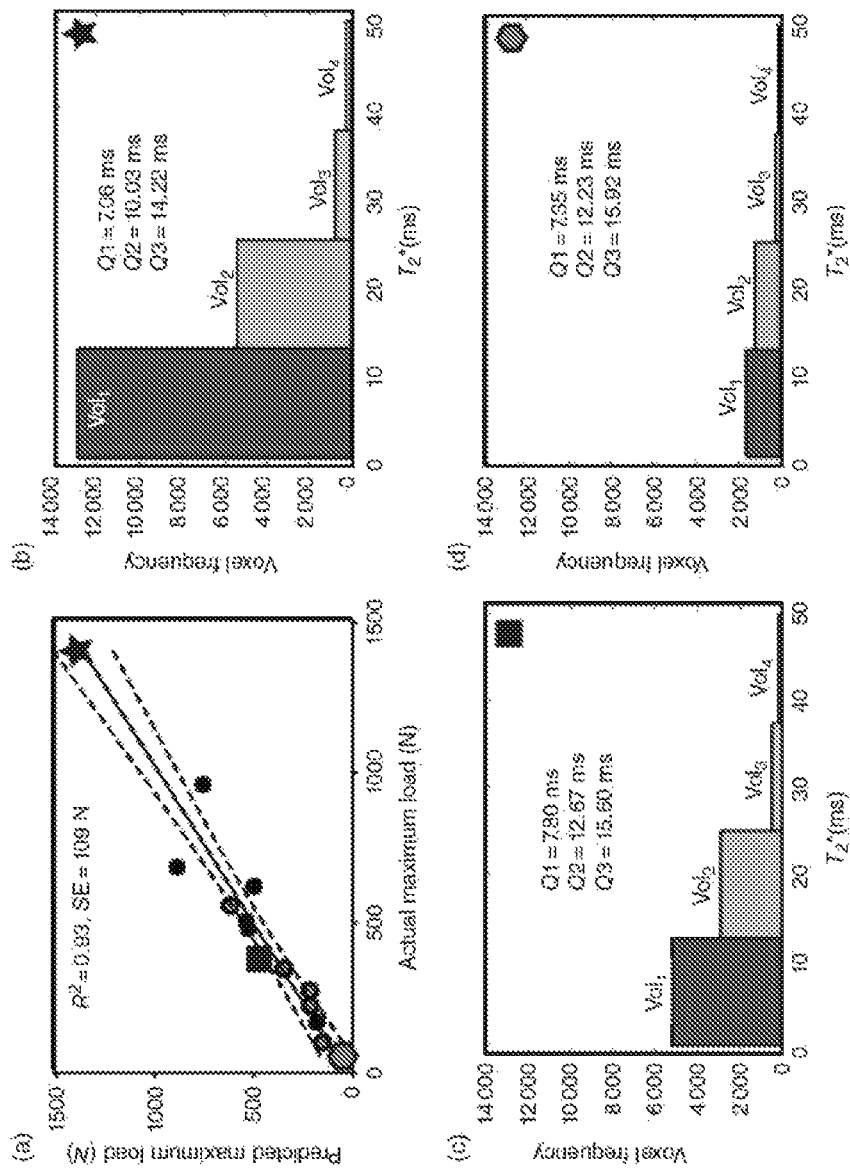
FIG. 32 is a reproduction of FIG. 6 and includes a set of plots depicting a $T_2$* model: (A) Actual versus predicted maximum load calculated using the linear combination of $Vol_1$, $Vol_2$, $Vol_3$ and $Vol_4$ of the healing ligaments. The highest (star, B), median (square, C) and lowest (hexagon, D) maximum load ligaments and their corresponding histogram profile are also represented. Note that we have run the analysis using 4, 8 and 16 bins, however, 4 bins was sufficient to represent the distribution effects and how they change with degree of healing. (Reproduced with permission from Biercevicz et al. (54)).

The voxels corresponding to the ligament were extracted from the maps, and the whole ligament volume was then binned into four separate tissue sub-volumes ($Vol_1$, $Vol_2$, $Vol_3$, $Vol_4$) with equal $T_2^*$ intervals (bins) up to 50 ms (0-12.5; 12.6-25; 25.1-37.5; 37.6-50 ms, respectively) (FIG. 31). The linear combination of the ligament sub-volumes defined by increasing $T_2^*$ intervals ($Vol_1$, $Vol_2$, $Vol_3$, $Vol_4$) significantly predicted maximum load, yield load, and linear stiffness ($R^2$=0.93, 0.78, and 0.88, respectively). Standard errors for the prediction of maximum load (FIG. 32), yield load, and linear stiffness were 109 N, 141 N and 26 N/mm, respectively. $Vol_1$ represents the most organized tissue with the lowest $T_2$* interval and it was found to contribute the most to structural properties (FIG. 32). In a subsequent histological analysis of the healing graft from the same animals, it was determined that the $T_2$* value significantly predicted total Ligament Maturity Index score as well as the cell, collagen and vessel sub-scores, while ligament volume predicted the total score and the cell and collagen sub-scores (47). A lower $T_2$* or higher volume was associated with a better score as would be expected based on the biomechanical findings (54). Studies using ultra-short echo time (UTE) imaging also found correlations between $T_2$* and collagen orientation in the meniscus where a shorter $T_2$* was correlated with more closely packed collagen fibers and less meniscal damage (21, 57). While the study of Biercevicz et al. (54) did not utilize the ultra-short echo times permitted by UTE imaging and was limited by including only two echo times, tissues with shorter $T_2$* values were associated with higher biomechanical failure properties and histological scores. Therefore $T_2$* may serve as a surrogate for tissue organization and healing. Further refinement could be achieved by collecting additional shorter echo times which would improve certainty of the $T_2$* estimation.

$T_2$* estimation not only provides a valuable means to document healing in ligaments or tendons, it may also predict the loss of structural integrity due to degeneration in aging, intact ligaments (68). Fifteen fresh cadaver knees with a median age of 54 (range 24 to 76 years) were imaged on a 3 T scanner. The age range was selected assuming that degeneration would be greater in the older knees. A high resolution 3-D gradient echo sequence was employed [TR=33 ms, TE=4.3, 7.3, 10.2, 13.1, 16 ms (6 echoes), flip angle=17°, FOV=180 mm, slice thickness=0.8 mm, reconstruction matrix size=512×512, slice thickness=0.8 mm (contiguous slices), single average, and bandwidth=407 Hz/pixel] (68). To create the $T_2$* map for each knee, a voxel-wise nonlinear least-squares fit of voxel signal intensity (Equation 2) for six echo times was used to estimate $T_2$*. Using volume in conjunction with the median $T_2$* value, the multiple linear regression model did not adequately predict maximum failure load or linear stiffness of the intact human ACL ($R^2$<0.23). However, when the specimens were split into a high and a low failure group, with the split divided at the median value, the ligaments with the inferior failure properties had significantly higher $T_2$* values than those with superior failure properties. Naturally restricted distributions of the intact ligament volume and $T_2$* (demonstrated by the respective Z-scores) in an older cadaveric population were the likely reason for the insignificant regression results (68). While encouraging, these data suggest that better resolution may be required to evaluate age related changes in the properties of the normal ACL in the older population, which could potentially be achieved with more advanced imaging techniques.

MR Imaging and Contrast Mechanisms

MR image contrast depends on a combination of physical (e.g., proton density), chemical (e.g., types of molecules with which the protons interact), and biologic (e.g., tissue composition) properties. The wide range of contrast mechanisms available in MR imaging has made it the modality of choice for many soft tissue applications. In order to evaluate the capabilities of different MR imaging techniques and their potential for assessing normal, injured, and healing ligaments and tendons, it is necessary to briefly review the principles of MR imaging and MR-derived tissue contrast.

MRI Techniques

In 1973, Lauterbur first showed that a linear field gradient superimposed on the main magnetic field generated projections of an object from which the object could be reconstructed (69). When the field varied linearly in a particular direction, the resonance frequency was dependent on the location of the volume element with respect to the direction. Hence, the resulting free induction decay was the superposition of the different frequency components. To determine individual frequencies, Fourier transform (FT) techniques have been used. This allows extraction of the individual frequencies, as well as their associated amplitudes, that are proportional to the spin density at the particular spatial location. To obtain a MR image, slice selection, phase-encoding, and frequency-encoding gradients are applied and one line of the so-called k-space is recorded. By varying the three gradients to record different lines of the k-space, the entire k-space is filled. Then, a MR image can be reconstructed with the FT of the k-space data. A second method is that of back projection imaging. By rotating the gradient in small angular increments, a series of projections are generated. Using filtered back-projection techniques (as in X-ray computed tomography), an image can then be reconstructed. Though this projection-reconstruction technique has flaws, such as poor resolution and sensitivity to magnetic field inhomogeneity, it has received more interest recently because of its much shorter echo delays.

Spin density and relaxation are two most important properties that contribute to MR image contrast. Spin density is the number of MR visible spins per volume. Relaxation is the most biologically variable process and is the predominant source of contrast in MR imaging. There exist two types of relaxation: longitudinal ($T_1$ or spin-lattice) relaxation, and transverse ($T_2$ or spin-spin) relaxation. $T_1$ and $T_2$ relaxation times and proton density vary, often considerably, among biological tissues.

The relaxation of nuclear magnetization (M) is described by the Bloch Equation (70):

$$\frac{d\vec{M}}{dt} = \gamma \vec{M} \times \vec{B} - \frac{\vec{M}_{tr}}{T_2} - \frac{M_z - M_0}{T_1} \quad (4)$$

where $\vec{M}$ is the magnetization, $\vec{B}$ is magnetic field strength that includes the $B_0$ and $B_1$ fields, $\vec{M}_{tr}$ is the transverse magnetization, $M_z$ is the longitudinal magnetization, and $M_0$ is the magnetization at equilibrium state. To model other imaging contrast mechanisms, such as diffusion or cross-relaxation, modification of the Bloch equations with the addition of more terms is required (71).

$T_1$ relaxation time describes the manner in which the longitudinal magnetization (in the z direction) regains its equilibrium after being excited by a radiofrequency (RF) pulse. It is a process whereby magnetization releases energy from the RF pulse to the lattice. $T_1$ relaxation of the spins excited by a 90° RF pulse in the imaging sequence can be expressed as $$M_z(t) = M_0\left(1 - \exp\left(-\frac{t}{T_1}\right)\right) \quad (5)$$

where $M_z$ and $M_0$ are longitudinal magnetizations at time t and time 0. Tissue with short $T_1$ relaxation times appear brighter in MR images with dominant $T_1$ contrast ($T_1$-weighted images) than tissues with long $T_1$. $T_1$-weighted images are acquired with TE<$T_2$ in the tissue of interest in order to reduce $T_2$ modulation of signal, and adequate TR (TR≈$T_1$).

$T_2$ relaxation, or spin-spin relaxation, describes the dephasing of the spins after they have been excited. The dephasing of $M_0$ produces a detectable MR signal, which disappears at a higher rate than the $T_1$ signal. $T_2$ relaxation reflects the exchange of energy among neighboring spins. The dephasing process is also caused by local magnetic field inhomogeneities which include microscopic effects related to magnetic interactions among neighboring molecules and macroscopic effects related to spatial variation of the external magnetic field. The dephasing of transverse magnetization caused by a combination of spin-spin relaxation and magnetic field inhomogeneity is known as $T_2^*$ relaxation. $T_2$ relaxation reflects the dephasing caused by spin-spin interaction, while $T_2^*$ reflects dephasing produced by both effects and is always shorter than $T_2$. After RF excitation, the rapid decay in signal detected is termed the free induction decay (FID), which decays approximately exponentially with $T_2^*$. The relationship between $T_2$ and $T_2^*$ can be expressed as:

$$\frac{1}{T_2^*} = \frac{1}{T_2} + \frac{1}{T_2^+} \quad (6)$$

where $T_2^+$ is signal loss caused by external field inhomogeneity. The phase dispersion caused by the external field inhomogeneity ($T_2^*$ effect) can be recovered by 180° pulses in spin-echo sequences.

$T_2$ relaxation of spins that have been excited by a 90° RF pulse in the imaging sequence can be expressed as:

$$M_z(t) = M_0 \exp\left(-\frac{t}{T_2}\right) \quad (7)$$

Variations in $T_2$ relaxation time among different tissues and lesions can be utilized to generate MR images with predominantly $T_2$ contrast. These images are characterized by the bright appearance of tissue with long $T_2$ and dark appearance of tissue with short $T_2$. $T_2$-weighted images are acquired with TE approximately equal to or longer than the shortest $T_2$ in the tissue of interest, while with long TR (i.e., TR>$T_1$) to reduce $T_1$ modulation of signal.

Proton density is the number of protons in a given volume which contributes to MR imaging; hence, MR signal requires the presence of protons. Within a MR image, tissues with different visible proton densities have different signal intensity and therefore create proton or spin density contrast. Proton density weighted images are produced using short echo time (TE<$T_2$) and long repetition time (TR>$T_1$) in order to reduce $T_2$ and $T_1$ modulations of signal, respectively.

The apparent diffusion coefficient (ADC) is a measure of the magnitude of diffusion of water molecules within the tissue and is commonly obtained using MR with diffusion weighted imaging (DWI). Diffusion is the random translational motion of molecules caused by their thermal energy and is associated with the viscosity of the medium. MR has the unique capacity to detect diffusion effects. Diffusion of water protons through an inhomogeneous magnetic field, which causes dephasing, is responsible for signal loss in $T_2$-weighted spin-echo images. In most cases, diffusion is not apparent in MR images acquired with conventional pulse sequences. DWI pulse sequences, which use a special combination of strong gradients, are utilized to detect the diffusion effects. With different b-values (a factor that reflects the strength and timing of the gradients used to generate diffusion-weighted images) applied, the ADC can be computed by fitting the measured signal to a single exponential model. Diffusion weighting can be diagnostically useful (e.g., in ischemia), because certain properties can only be visualized via alterations in their diffusion characteristics(72).

Sotak et al. studied the diffusion behavior in intact rabbit Achilles tendons along with changes in ADC after tensile loading of the tissues in vitro(73). The investigators showed that, for both freshly isolated and saline-stored tendons, ADC was significantly greater in the direction parallel to the long axis of the tendon than in the perpendicular direction for unloaded tendons. Following application of a 5N tensile load, a significant increase in ADC in the periphery of the tendon was observed relative to that of the tissue core, indicating extrusion of water along the radial direction of the tendon. While ADC increased in both directions under load, it decreased to baseline levels upon unloading.

Advanced MR Techniques

Magnetization transfer (MT) refers to the transfer of nuclear spin polarization from one population of nuclei to another. Biological tissues are highly heterogeneous and are predominantly composed of water and macromolecules. In many tissues, such as ligament and tendon, an abundance of protons are not directly visible, which substantially affects the visible protons. These protons have very short $T_2$ (ranging from a few hundred μsec to several msec) and are associated with large immobile protein membranes. These protons can be excited and will transfer their saturation to the MR visible protons, thus increasing the saturation of the visible protons. Specifically, saturation of the restricted protons leads to reduction in signal intensity of free, mobile protons that are visible to MR; this effect is referred to as magnetization transfer. First demonstrated by Wolff and Balaban, magnetization transfer contrast (MTC) in MR imaging is a contrast mechanism for selectively observing the interaction of bulk water protons with the protons contained in macromolecules of tissue(74). Coupling between the macromolecular protons and the free or 'liquid' protons allows the spin state of the macromolecular protons to influence the spin state of the liquid protons through exchange processes. Owing to the variation of macromolecular compositions across tissues, the degree of interaction, or MT, can differ widely, generating high tissue contrast.

To quantify the magnetization transfer process, magnetization transfer ratio (MTR) is used. It is defined as:

$$MTR = 100 \times \frac{M_0 - M_s}{M_0} \quad (8)$$

where $M_0$ is the proton density weighted signal measured in the absence of the pre-saturation RF pulse. $M_s$ is the proton density weighted signal measured in the presence of pre-saturation RF pulse to the restricted protons. However, MTR is challenging to reproduce across studies due to the variety of parameters that modulate the contrast. These parameters include the method of the macromolecule saturation (such as irradiation power, offset frequency, and duty cycle) as well as image acquisition parameters including repetition time, echo time and flip angle, and $B_0$ and $B_1$ field inhomogeneity. To overcome these limitations, a more rigorous method of quantitative imaging based on the MT model, which accounts for the experimental and biological parameters involved, such as shape and width of MT saturation pulse(s), effect of magnetic field strength, and characteristics of the biological tissues, has been receiving more emphasis. A set of new methods has been developed for quantitative magnetization transfer imaging (qMTI)(75).

The MT mechanism is not well understood at the molecular level, though it is at the tissue level. The possible pathways of magnetization exchange are complex, including chemical exchange between water and various functional groups of a biopolymer (e.g., amide or hydroxyl), dipolar interactions, diffusion of water molecules, and spin diffusion within the macromolecule. Despite discrepancies in posited MT molecular mechanisms across studies, chemical exchange and dipolar coupling are considered major sources of MT(76).

Nonetheless, MT has been shown to be a useful tool for improving the diagnostic performance of MR imaging. The MT technique has been used for the assessment of white matter disease in multiple sclerosis, breast lesions, diseases of articular cartilage and the development of tissue engineered cartilage, cerebral ischemia, MR angiography, and contrast agent studies(76). While few studies have applied MTR analyses to ligament and tendon, Syha et al. reported a MTR of Achilles tendons of healthy volunteers as 0.53±0.05 at 1 kHz, while the MTR for one patient with confirmed tendinopathy was 0.36(77). While this provides proof of concept, the clinical utility of MT imaging of ligament and tendon remains to be established.

$T_{1\rho}$ relaxation is the relaxation that occurs after the application of a spin-lock pulse. Spin-lock MR imaging techniques employ low power RF pulses applied directly on-resonance with the Larmor precession frequency, locking the magnetization vector into a rotated frame. $T_{1\rho}$ MR imaging is an alternative to conventional $T_1$ and $T_2$ imaging in which a long-duration, low-power RF pulse, referred to as spin-lock pulse, is applied to the magnetization in the transverse plane. Spin-lock allows the coupling of spins to frequencies that are generally lower than the Larmor frequency. Therefore, regimes such as low frequency physicochemical interactions between water and extracellular matrix molecules can be studied; matrix changes, such as loss of proteoglycans from collagenous tissues, are reflected in the $T_{1\rho}$ parameter. $T_{1\rho}$-weighting provides $T_2$-like images with the advantage of increased dynamic range for assessment of tissue degenerative changes compared to conventional $T_2$-weighting. Since $T_{1\rho}$ attenuates the effect of MRI signal loss mechanisms (i.e., dipolar relaxation, static dipolar coupling, chemical exchange, and background gradients), $T_{1\rho}$ relaxation times always exceed those of $T_2$. In a typical $T_{1\rho}$ mapping experiment, the duration of the spin-lock pulse is changed incrementally while the amplitude of the spin-lock pulse ($\gamma B_1 \sim 0.1$-few kHz) is fixed. Numerous biological tissues including tumors, skeletal muscle, myocardium, blood flow, and articular cartilage have been studied using $T_{1\rho}$ imaging(78-81).

In studies of articular cartilage (82-85), the demonstrated inverse correlation between $T_{1\rho}$ and proteoglycan content and has proven to be quite valuable for non-invasive assessment of the status of cartilage degeneration and repair. Recently, $T_{1\rho}$-weighted images of Achilles tendon and meniscus have been acquired (86-92). The mean $T_{1\rho}$ for the Achilles tendon ranged from 5.2±0.58 ms for normal cadaver tendons and increased to 9.0±0.24 ms in a specimen with a degenerated tendon at $B_0$=3T (91). High-quality $T_{1\rho}$ imaging and quantification of the Achilles tendon and meniscus can be achieved with 2D UTE sequences combined with spin-lock preparation, though the technique has limitations such as sensitivity to eddy currents, field inhomogeneity, gradient nonlinearity and relatively long scanning times.

UTE imaging has become increasingly popular for imaging collagenous tissues. Biological tissues are heterogeneous and have components (e.g., extracellular fibers, ground substance, and stationary and migrating cells) with different values of $T_2$. The signal in an MR image is the spatial integration over a voxel containing protons that are affected differentially by the pulse sequence. The observed signal S0 produced by MR excitation is given by $$S_0 = K\rho \Sigma c_r f(T_{1r}, T_{2r}),  \quad (9)$$

where $\rho$ is the total proton density; $c_r$ is the fraction of the proton density; $T_{1r}$, $T_{2r}$ are effective relaxation time constants of the rth component of the tissue being imaged. K is a scaling factor relating the proton density to the measured signal, and $f(T_{1r}, T_{2r})$ describes the response of the rth component to the imaging sequence in use, assuming that the effects of the exchange processes on MR signals can be represented as variations in time constants(93). While tissues such as cortical bone, tendons, ligaments and menisci contain a majority of short T2 components, other tissues also contain short $T_2$ relaxation components, but as a minority species(94). Signal from the short $T_2$ components in these tissues is not detected with conventional clinical pulse sequences where the majority of MR signal is derived from the long $T_2$ components.

UTE pulse sequences can be used to enhance the MR signal from tissues with short $T_2$ relaxation times, such as tendons and ligaments. UTE sequences image the restricted protons directly to produce images weighted by the actual size of the bound proton and its relaxation rate. UTE pulse sequences have TEs that are 100-1,000 times shorter than those used in conventional spin-echo sequences for imaging tendons and ligaments and can detect signal from these tissues before the signal has substantially decayed.

Using short TE's, investigators have further characterized the imaging features and anatomy of the Achilles tendon enthesis and the three fibrocartilaginous components of the "enthesis organ," (95) which cannot be reliably imaged using conventional pulse sequences. UTE sequences are also beneficial in imaging collagen degeneration proximal to the Achilles insertion site, where the tendon is most vulnerable to degenerative changes or rupture, 2-6 cm above its enthesis (95).

Clinical applications for UTE imaging have been explored in multiple studies. These include imaging calcifications, cavernomas, and metastases in the brain, hemochromatosis and cirrhosis in the liver, the periosteum, cortical bone, lung parenchyma, tendon, knee menisci and articular cartilage(87, 93, 96). In comparing subjects with normal Achilles tendons and patients with chronic tendinopathy, it was determined that the short component $T_2^*$ values of the patients was significantly greater than that of controls (0.53±0.17 vs 0.34±0.09 ms) at 7T, suggesting that $T_2^*$ may be a promising biomarker to identify pathological changes in the Achilles tendon (97).

Figure 33:
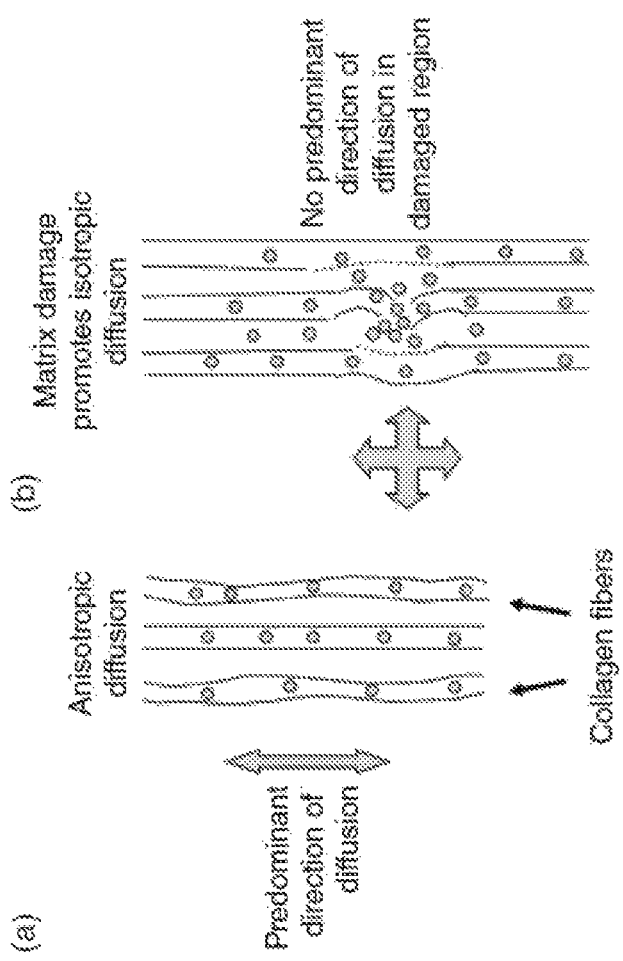
FIG. 33 is a schematic diagram illustrating effects of matrix disruption on water diffusion. (a) In normal tendon or ligament, water molecules (blue circles) preferentially diffuse in a direction (illustrated by blue arrow) parallel to the collagen fibers. (b) Matrix disruption promotes isotropic diffusion whereby there is no longer a predominant direction of diffusion in the damaged region.

Diffusion tensor imaging (DTI) also holds considerable promise for imaging ligaments and tendons. Water content is the primary factor governing MR differences between tissues, where the relaxation time is generally a linear function of the solute concentration. These MR parameters have the potential to be used to evaluate water distribution within tissues and thus visualize the disease progression or tissue regeneration. Diffusion of water is an indication of the morphological and biochemical integrity of tissues. In the region where cells swell or cell membranes rupture due to diseases, for example, the water diffusion is faster because there are fewer physical barriers. As described in the preceding herein, DWI is based on the measurement of random (Brownian) motion of water molecules, which is sensitive to the physiological and anatomical environment of tissues. In isotropic tissues, where the apparent diffusivity is independent of the orientation of the tissue, it is usually sufficient to characterize the diffusion characteristics with a single scalar, ADC. However, diffusion in tissues with a highly ordered structure (e.g., white matter, skeletal muscle, tendon and ligament) is typically anisotropic (FIG. 33). This diffusion anisotropy can be detected, quantified, and visualized using DTI.

The DTI technique combines magnetic resonance diffusion-weighted pulse sequences with tensor mathematics to measure molecular diffusion in three dimensions, thereby providing a non-invasive proxy measure of microstructural integrity (98). The diffusion of water molecules within fibrous tissues (e.g., ligament) is not equal in all directions, as molecular restriction is greater across than along the major fiber axis. Hence, it is presumed that intact tendons and ligaments promote anisotropic diffusion, whereas damaged tissue promotes isotropic diffusion (FIG. 33). DTI, which is based on the effect of anisotropic diffusion in fiber tracts, enables quantitative description of highly structured tissue, such as white matter, using a series of parameters describing diffusion in tissues, most notably ADC or mean diffusivity (MD), fractional anisotropy, (FA), axial diffusivity (AD), and radial diffusivity (RD). DTI index maps (e.g. FA, MD, AD, and RD) are generated by applying the following equations for each pixel:

$$MD = \frac{\lambda_1 + \lambda_2 + \lambda_3}{3} \quad (10)$$

$$AD = \lambda_1$$

$$RD = \frac{(\lambda_2 + \lambda_3)}{2}$$

$$FA = \frac{\sqrt{3}\sqrt{(\lambda_1 - MD)^2 + (\lambda_2 - MD)^2 + (\lambda_2 - MD)^2}}{\sqrt{2}\sqrt{\lambda_1^2 + \lambda_2^2 + \lambda_3^2}}$$

where $\lambda_1, \lambda_2, \lambda_3$ are the eigenvalues generated from the diffusion weighted images.

Fractional anisotropy is a scalar metric that describes the directionality of the diffusion tensor and has values ranging between 0 (isotropic) and 1 (anisotropic). Mean diffusivity is a non-directional measure of free translational diffusion and provides an index of general tissue integrity (diffusivity increases with matrix damage)(99). MD is further resolved into axial and radial diffusivity to quantify anisotropic diffusion.

In a recent pilot study, Yang and coworkers performed DTI of healthy ACLs in control subjects and healing grafts in patients following ACL reconstruction (100). The authors reported a significantly higher FA and lower ADC of the intra-tunnel portions of the healing grafts (range of post-operative imaging date, 3 months to 10 years) in comparison to those of the intra-articular region of the graft. In a study of Achilles tendon healing, FA of the healing tendon (median follow-up, 21 months) was significantly less than that of the contralateral normal (control) tendon though there were no differences between the mean ADC values (101). While the DTI method needs further refinement and validation, these studies suggest that DTI holds considerable promise as a quantitative, non-invasive assessment tool for tissue-engineered and/or healing tendon and ligament.

Figure 34:
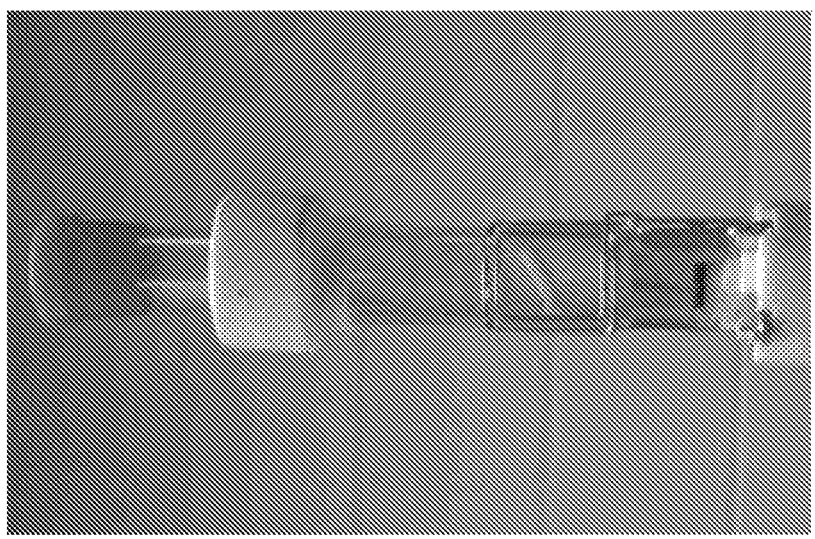
FIG. 34 is a schematic diagram illustrating effects of matrix disruption on water diffusion. (a) In normal tendon or ligament, water molecules (blue circles) preferentially diffuse in a direction (illustrated by blue arrow) parallel to the collagen fibers. (b) Matrix disruption promotes isotropic diffusion whereby there is no longer a predominant direction of diffusion in the damaged region.

Challenges with in vivo DTI of ligament and tendon on clinical scanners (e.g., low field strength, low SNR, low resolution, costs)(102) prompted two of the current authors (WL, VMW) to pursue high field ex-vivo scans on a 11.7 T vertical bore research magnet. Initial experiments at 11.7 T refined the scan acquisition parameters for DTI of rabbit semitendinosus tendon and medial collateral ligament (MCL) (FIG. 34)(103). FA values of 0.67±0.23 for semitendinosus tendons and 0.66±0.17 for MCL confirmed the highly anisotropic collagenous structure of these tissue types. Further studies at 11.7 T revealed that the fiber density index (DTI-Studio v. 3) of semitendinosus tendons was the highest within a range of b-values from 300-600 s/mm².

Conclusion

Measurements of signal intensity using conventional MRI to evaluate tissue maturation and degeneration have become increasingly popular. However, there are significant limitations accompanying this strategy, due in part to the low signal intensities of these tissues and because the MR images are highly dependent on hardware and image acquisition parameters. $T_2$ and $T_2^*$ relaxation times are inherent tissue properties that are less sensitive to imaging acquisition parameters. As $T_2^*$ utilizes shorter echo times, $T_2^*$ mapping provides a more reliable alternative to capture changes in ligament or tendon tissues. Mapping these values across a ligament or tendon provides insight into structural organization and functional integrity. More advanced MR imaging methods for ligament and tendon, such as UTE and DTI, are under development. These methods may significantly advance our ability to utilize even shorter echo times or to directly image the fiber structure of intact, injured, repaired, or surgically reconstructed tissues, which in turn would further our understanding of microstructural mechanisms of degeneration and repair. Advanced imaging techniques may potentially improve the clinical management of injuries and the translation of novel tissue engineering strategies to improve outcomes.

Example 16 References

1. Benjamin M, Kaiser E, Milz S. Structure-function relationships in tendons: a review. Journal of anatomy. 2008; 212(3):211-28.
2. Blevins F T, Djurasovic M, Flatow E L, Vogel K G. Biology of the rotator cuff tendon. The Orthopedic clinics of North America. 1997; 28(1):1-16.
3. Wang J H. Mechanobiology of tendon. Journal of biomechanics. 2006; 39(9):1563-82.
4. Provenzano P P, Vanderby R. Collagen fibril morphology and organization: implications for force transmission in ligament and tendon. Matrix Biology. 2006; 25(2):71-84.
5. Kastelic J, Galeski A, Baer E. The multicomposite structure of tendon. Connective tissue research. 1978; 6(1):11-23.
6. Lynch H A, Johannessen W, Wu J P, Jawa A, Elliott D M. Effect of fiber orientation and strain rate on the nonlinear uniaxial tensile material properties of tendon. J Biomech Engin. 2003; 25(5):726-31.

7. Hodgson R J, O'Connor P J, Grainger A J. Tendon and ligament imaging. The British journal of radiology. 2012; 85(1016):1157-72.
8. Kannus P, Jozsa L. Histopathological changes preceding spontaneous rupture of a tendon. A controlled study of 891 patients. The Journal of bone and joint surgery American volume. 1991; 73(10):1507-25.
9. Sharma P, Maffulli N. Tendon injury and tendinopathy: healing and repair. The Journal of bone and joint surgery American volume. 2005; 87(1):187-202.
10. Lin T W, Cardenas L, Soslowsky L J. Biomechanics of tendon injury and repair. Journal of biomechanics 2004; 37(6):865-77.
11. Murray M M, Fleming B C. Biology of anterior cruciate ligament injury and repair: Kappa delta ann doner vaughn award paper 2013. J Orthop Res. 2013; 31(10):1501-6.
12. Breidenbach A P, Gilday S D, Lalley A L, Dyment N A, Gooch C, Shearn J T, et al. Functional tissue engineering of tendon: Establishing biological success criteria for improving tendon repair. Journal of biomechanics 2014; 47(9):1941-8.
13. Sayegh E T S J, Virk M S, Romeo A A, Wysocki R W, Galante J O, Trella K J, Plaas A, Wang V M. Recent Scientific Advances Towards the Development of Tendon Healing Strategies. Current Tissue Eng. 2015(In press).
14. Chao L H, Murray M M. The Role of Inflammation and Blood Cells in Wound Healing. In: Murray M M, Vavken P, Fleming B C, editors. The ACL Handbook: Knee Biology, Mechanics, and Treatment. New York: Springer; 2013. p. 73-89.
15. Miller T T. MR imaging of the knee. Sports Med Arthrosc. 2009; 17(1):56-67.
16. McRobbie D W, Moore E A, Graves M J, Prince M R. MRI from Picture to Proton. 2nd ed. Cambridge: Cambridge University Press; 2007.
17. Proffen B L, Fleming B C, Murray M M. Histologic predictors of maximum failure loads differ between the healing ACL and ACL grafts after 6 and 12 Months in vivo. Orthop J Sports Med. 2013; 1(6):1-11.
18. Dayan D, Hiss Y, Hirshberg A, Bubis J J, Wolman M. Are the polarization colors of picrosirius red-stained collagen determined only by the diameter of the fibers? Histochemistry. 1989; 93(1):27-9.
19. Rich L, Whittaker P. Collagen and picrosirius red staining: A polarized light assessment of fibrillar hue and spatial distribution. Braz J Morphol Sci. 2005; 2:97-104.
20. Junqueira L C, Cossermelli W, Brentani R. Differential staining of collagens type I, II and III by Sirius Red and polarization microscopy. Archivum histologicum Japonicum=Nihon soshikigaku kiroku. 1978; 41(3):267-74.
21. Williams A, Qian Y, Golla S, Chu C R. UTE-T2* mapping detects sub-clinical meniscus injury after anterior cruciate ligament tear. Osteoarthritis Cartilage. 2012; 20(6):486-94.
22. Murray M M, Fleming B C. Use of a bioactive scaffold to stimulate anterior cruciate ligament healing also minimizes posttraumatic osteoarthritis after surgery. Am J Sports Med. 2013; 41(8):1762-70.
23. Noyes F R, Grood E S. The strength of the anterior cruciate ligament in humans and rhesus monkeys. The Journal of bone and joint surgery American volume. 1976; 58(8):1074-81.
24. Weiler A, Peters G, Maurer J, Unterhauser F N, Sudkamp N P. Biomechanical properties and vascularity of an anterior cruciate ligament graft can be predicted by contrast-enhanced magnetic resonance imaging—A two-year study in sheep. Am J Sports Med. 2001; 29(6):751-61.
25. Biercevicz A M, Akelman M R, Fadale P D, Hulstyn M J, Shalvoy R M, Badger G J, et al. MRI volume and signal intensity of ACL graft predict clinical, functional, and patient-oriented outcome measures after ACL reconstruction. Am J Sports Med. 2015; 43(3):693-9.
26. Nesbitt R J, Herfat S T, Boguszewski D V, Engel A J, Galloway M T, Shearn J T. Primary and secondary restraints of human and ovine knees for simulated in vivo gait kinematics. Journal of biomechanics. 2014; 47(9): 2022-7.
27. Howell S M, Knox K E, Farley T E, Taylor M A. Revascularization of a human anterior cruciate ligament graft during the first two years of implantation. Am J Sports Med. 1995; 23(1):42-9.
28. Helm C A, Major N M, Anderson M W, Kaplan P, Dussault R. Musculoskeletal MRI, 2nd Edition: Saunders; 2009.
29. Weinreb J H, Sheth C, Apostolakos J, McCarthy M B, Barden B, Cote M P, et al. Tendon structure, disease, and imaging. Muscles, ligaments and tendons journal. 2014; 4(1):66-73.
30. McFarland E G, Morrey B F, An K-N, Wood M B. The relationship of vascularity and water content to tensile strength in a patellar tendon replacement of the anterior cruciate in dogs. Am J Sports Med. 1986; 14(6):436-48.
31. Murray M M, Spindler K P, Abreu E, Muller J A, Nedder A, Kelly M, et al. Collagen-platelet rich plasma hydrogel enhances primary repair of the porcine anterior cruciate ligament. J Orthop Res. 2007; 25(1):81-91.
32. Arai Y, Hara K, Takahashi T, Urade H, Minami G, Takamiya H, et al. Evaluation of the vascular status of autogenous hamstring tendon grafts after anterior cruciate ligament reconstruction in humans using magnetic resonance angiography. Knee Surg Sports Traumatol Arthrosc. 2008; 16(4):342-7.
33. Figueroa D, Mclean P, Calvo R, Vaisman A, Zilleruelo N, Figueroa F, et al. Magnetic resonance imaging evaluation of the integration and maturation of semitendinosus-gracilis graft in anterior cruciate ligament reconstruction using autologous platelet concentrate. Arthroscopy. 2010; 26(10):1318-25.
34. Howell S M, Clark J A, Blasier R D. Serial magnetic resonance imaging of hamstring anterior cruciate ligament autografts during the first year of implantation. A preliminary study. Am J Sports Med. 1991; 19(1):42-7.
35. Murakami Y, Sumen Y, Ochi M, Fujimoto E, Adachi N, Ikuta Y. MR evaluation of human anterior cruciate ligament autograft on oblique axial imaging. J Comput Assist Tomogr. 1998; 22(2):270-5.
36. Radice F, Yanez R, Gutierrez V, Rosales J, Pinedo M, Coda S. Comparison of magnetic resonance imaging findings in anterior cruciate ligament grafts with and without autologous platelet-derived growth factors. Arthroscopy. 2010; 26(1):50-7.
37. Saupe N, White L M, Chiavaras M M, Essue J, Weller I, Kunz M, et al. Anterior cruciate ligament reconstruction grafts: MR imaging features at long-term follow-up—correlation with functional and clinical evaluation. Radiology. 2008; 249(2):581-90.
38. Valenti Azcarate A, Lamo-Espinosa J, Aquerreta Beola J D, Hernandez Gonzalez M, Mora Gasque G, Valenti Nin J R. Comparison between two different platelet-rich plasma preparations and control applied during anterior cruciate ligament reconstruction. Is there any evidence to support their use? Injury. 2014; 45 Suppl 4:S36-41.

39. Kiekara T, Jarvela T, Huhtala H, Moisala A S, Suomalainen P, Paakkala A. Tunnel communication and increased graft signal intensity on magnetic resonance imaging of double-bundle anterior cruciate ligament reconstruction. Arthroscopy. 2014; 30(12):1595-601.
40. Mutsuzaki H, Kanamori A, Ikeda K, Hioki S, Kinugasa T, Sakane M. Effect of calcium phosphate-hybridized tendon graft in anterior cruciate ligament reconstruction: a randomized controlled trial. Am J Sports Med. 2012; 40(8):1772-80.
41. Ma Y, Murawski C D, Rahnemai-Azar A A, Maldjian C, Lynch A D, Fu F H. Graft maturity of the reconstructed anterior cruciate ligament 6 months postoperatively: a magnetic resonance imaging evaluation of quadriceps tendon with bone block and hamstring tendon autografts. Knee Surg Sports Traumatol Arthrosc. 2015; 23(3):661-8.
42. Tanaka Y, Yonetani Y, Shiozaki Y, Kanamoto T, Kita K, Amano H, et al. MRI analysis of single-, double-, and triple-bundle anterior cruciate ligament grafts. Knee Surg Sports Traumatol Arthrosc. 2014; 22(7):1541-8.
43. Li H, Tao H, Cho S, Chen S, Yao Z, Chen S. Difference in graft maturity of the reconstructed anterior cruciate ligament 2 years postoperatively: a comparison between autografts and allografts in young men using clinical and 3.0-T magnetic resonance imaging evaluation. Am J Sports Med. 2012; 40(7):1519-26.
44. Carroll C C, Dickinson J M, LeMoine J K, Haus J M, Weinheimer E M, Hollon C J, et al. Influence of acetaminophen and ibuprofen on in vivo patellar tendon adaptations to knee extensor resistance exercise in older adults. Journal of applied physiology. 2011; 111(2):508-15.
45. Anderson K, Seneviratne A M, Izawa K, Atkinson B L, Potter H G, Rodeo S A. Augmentation of tendon healing in an intraarticular bone tunnel with use of a bone growth factor. Am J Sports Med. 2001; 29(6):689-98.
46. Biercevicz A M, Miranda D L, Machan J T, Murray M M, Fleming B C. In situ, noninvasive, T2*-weighted MRI-derived parameters predict ex vivo structural properties of an anterior cruciate ligament reconstruction or bioenhanced primary repair in a porcine model. Am J Sports Med. 2013; 41(3):560-6.
47. Biercevicz A M, Proffen B L, Murray M M, Walsh E G, Fleming B C. T* relaxometry and volume predict semiquantitative histological scoring of an ACL bridge-enhanced primary repair in a porcine model. J Orthop Res. 2015; 48:1180-7.
48. Hensler D, Illingworth K D, Musahl V, Working Z M, Kobayashi T, Miyawaki M, et al. Does fibrin clot really enhance graft healing after double-bundle ACL reconstruction in a caprine model? Knee Surg Sports Traumatol Arthrosc. 2015; 23(3):669-79.
49. Deoni S C, Williams S C, Jezzard P, Suckling J, Murphy D G, Jones D K. Standardized structural magnetic resonance imaging in multicentre studies using quantitative T1 and T2 imaging at 1.5 T. Neuroimage. 2008; 40(2):662-71.
50. Gallimore G W, Jr., Harms S E. Knee injuries: high-resolution MR imaging. Radiology. 1986; 160(2):457-61.
51. Konig H, Sieper J, Wolf K J. Rheumatoid arthritis: evaluation of hypervascular and fibrous pannus with dynamic MR imaging enhanced with Gd-DTPA. Radiology. 1990; 176(2):473-7.
52. Mosher T J, Dardzinski B J. Cartilage MRI T2 relaxation time mapping: overview and applications. Seminars in musculoskeletal radiology. 2004; 8(4):355-68.
53. Ganal E, Ho C P, Wilson K J, Surowiec R K, Smith W S, Dornan G J, et al. Quantitative MRI characterization of arthroscopically verified supraspinatus pathology: comparison of tendon tears, tendinosis and asymptomatic supraspinatus tendons with T2 mapping. Knee Surg Sports Traumatol Arthrosc. 2015.
54. Biercevicz A M, Murray M M, Walsh E G, Miranda D L, Machan J T, Fleming B C. T2* MR relaxometry and ligament volume are associated with the structural properties of the healing ACL. J Orthop Res. 2014; 32(4):492-9.
55. Chavhan G B, Babyn P S, Thomas B, Shroff M M, Haacke E M. Principles, techniques, and applications of T2*-based MR imaging and its special applications. Radiographics. 2009; 29(5):1433-49.
56. Krasnosselskaia L V, Fullerton G D, Dodd S J, Cameron I L. Water in tendon: orientational analysis of the free induction decay. Magn Reson Med. 2005; 54(2):280-8.
57. Koff M F, Shah P, Pownder S, Romero B, Williams R, Gilbert S, et al. Correlation of meniscal T2* with multiphoton microscopy, and change of articular cartilage T2 in an ovine model of meniscal repair. Osteoarthritis Cartilage. 2013; 21(8):1083-91.
58. Kerslake R W, Jaspan T, Worthington B S. Magnetic resonance imaging of spinal trauma. The British journal of radiology. 1991; 64(761):386-402.
59. Mamourian A C, Dickman C A, Wallace R, Greene K A, Drayer B P, Sonntag V K H. Magnetic resonance appearance of the transverse ligament: an in vitro and in vivo anatomical and imaging study. MNI Quarterly. 1994; 10(1):27-30.
60. Fullerton G D, Cameron I L, Ord V A. Orientation of tendons in the magnetic field and its effect on T2 relaxation times. Radiology. 1985; 155(2):433-5.
61. Haacke E M, R. W. B, Thompson M R, Venkatsan R. Estimating T1 and T2 from Multiple Signal Measurements. Magnetic Resonance Imaging: Physical Principles and Sequence Design. New York: Wiley-Liss; 1999. p. 648-50.
62. Berendsen H J C. Nuclear magnetic resonance study of collagen hydration. J Chem Phys. 1962; 36:3297-305.
63. Guo C, Kaufman L J. Flow and magnetic field induced collagen alignment. Biomaterials. 2007; 28(6):1105-14.
64. Worcester D L. Structural origins of diamagnetic anisotropy in proteins. Proc Natl Acad Sci USA. 1978; 75(11):5475-7.
65. Pauling L. Diamagnetic anisotropy of the peptide group. Proc Natl Acad Sci USA. 1979; 76(5):2293-4.
66. Yang X, Sammet S, Schmalbrock P, Knopp M V. Postprocessing correction for distortions in T2* decay caused by quadratic cross-slice B0 inhomogeneity. Magn Reson Med. 2010; 63(5):1258-68.
67. Fernandez-Seara M A, Wehrli F W. Postprocessing technique to correct for background gradients in image-based R*(2) measurements. Magn Reson Med. 2000; 44(3):358-66.
68. Biercevicz A M, Akelman M R, Rubin L E, Walsh E G, Merck D, Fleming B C. The uncertainty of predicting intact anterior cruciate ligament degeneration in terms of structural properties using T relaxometry in a human cadaveric model. Journal of biomechanics 2015; 48:1188-92.
69. Lauterbur P C. Image Formation by Induced Local Interactions: Examples Employing Nuclear Magnetic Resonance. Nature. 1973; 242(5394):190-1.
70. Bloch F, Hansen W W, Packard M. The Nuclear Induction Experiment. Physical Review. 1946; 70(7-8):474.

71. Magin R L, Li W, Pilar Velasco M, Trujillo J, Reiter D A, Morgenstern A, et al. Anomalous NMR relaxation in cartilage matrix components and native cartilage: fractional-order models. J Magn Reson. 2011; 210(2):184-91.
72. van Bruggen N, Roberts T P, Cremer J E. The application of magnetic resonance imaging to the study of experimental cerebral ischaemia. Cerebrovasc Brain Metab Rev. 1994; 6(2):180-210.
73. Han S, Gemmell S J, Helmer K G, Grigg P, Wellen J W, Hoffman A H, et al. Changes in ADC caused by tensile loading of rabbit achilles tendon: evidence for water transport. J Magn Reson. 2000; 144(2):217-27.
74. Wolff S D, Balaban R S. Magnetization transfer contrast (MTC) and tissue water proton relaxation in vivo. Magn Reson Med. 1989; 10(1):135-44.
75. Henkelman R M, Huang X, Xiang Q S, Stanisz G J, Swanson S D, Bronskill M J. Quantitative interpretation of magnetization transfer. Magn Reson Med. 1993; 29(6): 759-66.
76. Henkelman R M, Stanisz G J, Graham S J. Magnetization transfer in MRI: a review. NMR Biomed. 2001; 14(2):57-64.
77. Syha R, Martirosian P, Ketelsen D, Grosse U, Claussen C D, Schick F, et al. Magnetization transfer in human Achilles tendon assessed by a 3D ultrashort echo time sequence: quantitative examinations in healthy volunteers at 3T. RoFo: Fortschritte auf dem Gebiete der Rontgenstrahlen and der Nuklearmedizin. 2011; 183(11):1043-50.
78. Koskinen S K, Virta A M, Niemi P T, Kajander S A, Komu M E. T1rho dispersion of rat tissues in vitro. Magn Reson Imaging. 1999; 17(7):1043-7.
79. Poptani H, Duvvuri U, Miller C G, Mancuso A, Charagundla S, Fraser N W, et al. T1rho imaging of murine brain tumors at 4 T. Acad Radiol. 2001; 8(1):42-7.
80. Wang C, Zheng J, Sun J, Wang Y, Xia R, Yin Q, et al. Endogenous contrast T1rho cardiac magnetic resonance for myocardial fibrosis in hypertrophic cardiomyopathy patients. J Cardiol. 2015.
81. Heo H Y, Wemmie J A, Johnson C P, Thedens D R, Magnotta V A. Eccentricity mapping of the human visual cortex to evaluate temporal dynamics of functional T1rho mapping. J Cereb Blood Flow Metab. 2015; 35(7):1213-9.
82. Wheaton A J, Dodge G R, Elliott D M, Nicoll S B, Reddy R. Quantification of cartilage biomechanical and biochemical properties via T1rho magnetic resonance imaging. Magn Reson Med. 2005; 54(5):1087-93.
83. Li X, Cheng J, Lin K, Saadat E, Bolbos R I, Jobke B, et al. Quantitative MRI using T1rho and T2 in human osteoarthritic cartilage specimens: correlation with biochemical measurements and histology. Magn Reson Imaging. 2011; 29(3):324-34.
84. Nishioka H, Hirose J, Nakamura E, Oniki Y, Takada K, Yamashita Y, et al. T1rho and T2 mapping reveal the in vivo extracellular matrix of articular cartilage. J Magn Reson Imaging. 2012; 35(1):147-55.
85. Jobke B, Bolbos R, Saadat E, Cheng J, Li X, Majumdar S. Mechanism of disease in early osteoarthritis: application of modern MR imaging techniques—a technical report. Magn Reson Imaging. 2013; 31(1):156-61.
86. Chang E Y, Campos J C, Bae W C, Znamirowski R, Statum S, Du J, et al. Ultrashort Echo Time T1rho Is Sensitive to Enzymatic Degeneration of Human Menisci. J Comput Assist Tomogr. 2015.
87. Wang L, Chang G, Bencardino J, Babb J S, Rokito A, Jazrawi L, et al. T1rho MRI at 3T of menisci in patients with acute anterior cruciate ligament (ACL) injury. J Magn Reson Imaging. 2015; 41(2):544-9.
88. Subburaj K, Souza R B, Wyman B T, Le Graverand-Gastineau M P, Li X, Link T M, et al. Changes in MR relaxation times of the meniscus with acute loading: an in vivo pilot study in knee osteoarthritis. J Magn Reson Imaging. 2015; 41(2):536-43.
89. Jungmann P M, Li X, Nardo L, Subburaj K, Lin W, Ma C B, et al. Do cartilage repair procedures prevent degenerative meniscus changes?: longitudinal t1rho and morphological evaluation with 3.0-T MRI. Am J Sports Med. 2012; 40(12):2700-8.
90. Rauscher I, Stahl R, Cheng J, Li X, Huber M B, Luke A, et al. Meniscal measurements of T1rho and T2 at MR imaging in healthy subjects and patients with osteoarthritis. Radiology. 2008; 249(2):591-600.
91. Du J, Carl M, Diaz E, Takahashi A, Han E, Szeverenyi N M, et al. Ultrashort TE T1rho (UTE T1rho) imaging of the Achilles tendon and meniscus. Magn Reson Med. 2010; 64(3):834-42.
92. Wang N, Xia Y. Anisotropic analysis of multi-component T2 and T1rho relaxations in achilles tendon by NMR spectroscopy and microscopic MRI. J Magn Reson Imaging. 2013; 38(3):625-33.
93. Robson M D, Gatehouse P D, Bydder M, Bydder G M. Magnetic resonance: an introduction to ultrashort TE (UTE) imaging. J Comput Assist Tomogr. 2003; 27(6): 825-46.
94. Robson M D, Benjamin M, Gishen P, Bydder G M. Magnetic resonance imaging of the Achilles tendon using ultrashort TE (UTE) pulse sequences. Clinical radiology. 2004; 59(8):727-35.
95. Benjamin M, Bydder G M. Magnetic resonance imaging of entheses using ultrashort TE (UTE) pulse sequences. J Magn Reson Imaging. 2007; 25(2):381-9.
96. Tyler D J, Robson M D, Henkelman R M, Young I R, Bydder G M. Magnetic resonance imaging with ultrashort TE (UTE) PULSE sequences: technical considerations. J Magn Reson Imaging. 2007; 25(2):279-89.
97. Juras V, Zbyn S, Pressl C, Valkovic L, Szomolanyi P, Frollo I, et al. Regional variations of T(2)* in healthy and pathologic achilles tendon in vivo at 7 Tesla: preliminary results. Magn Reson Med. 2012; 68(5):1607-13.
98. Mori S, Barker P B. Diffusion magnetic resonance imaging: Its principle and applications. The Anatomical Record. 1999; 257(3):102-9.
99. Basser P J, Pierpaoli C. Microstructural and physiological features of tissues elucidated by quantitative-diffusion-tensor MRI. J Magn Reson B. 1996; 111(3):209-19.
100. Yang X, Li M, Chen D, Shi D, Zhou Z, Zhu B, et al. Diffusion tensor imaging for anatomical and quantitative evaluation of the anterior cruciate ligament and ACL grafts: a preliminary study. J Comput Assist Tomogr. 2014; 38(4):489-94.
101. Sarman H, Atmaca H, Cakir O, Muezzinoglu U S, Anik Y, Memisoglu K, et al. Assessment of Postoperative Tendon Quality in Patients With Achilles Tendon Rupture Using Diffusion Tensor Imaging and Tendon Fiber Tracking. The Journal of foot and ankle surgery: official publication of the American College of Foot and Ankle Surgeons. 2015.
102. Wang V M, Bach B R Jr., Turner D A, Stebbins G T. Diffusion Tensor Imaging of Knee Ligaments: A Preliminary In Vivo Study. 8th International Symposium on Ligaments and Tendons 2008.
103. Gupta A, Li W, Stebbins G T, Magin R L, Wang V M. High Resolution Diffusion Tensor MRI of Rabbit Tendons and Ligaments at 11.7T. Annual Meeting of the International Society for Magnetic Resonance in Medicine (ISMRM); Stockholm, Sweden 2010.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method comprising:
defining a region on a scan comprising one or more of an anterior cruciate ligament (ACL) or an ACL graft;
obtaining a magnetic resonance (MR) imaging data set within the region;
deriving, using the MR imaging data, MR parameters that characterize a size and a quality of the ACL or the ACL graft;
using the MR parameters as inputs to a predictive model; and
generating, using the predictive model, a score characterizing a likelihood of failure of the ACL or ACL graft in a human patient;
wherein acquiring a magnetic resonance (MR) imaging data set is performed using a magnetic resonance imaging (MRI) system including a 1.5T to 11T magnet.

2. The method of claim 1, wherein the likelihood of failure includes a future clinical outcome including failure of the ACL or ACL graft.

3. The method of claim 1, wherein the MR parameters include signal intensity, signal-to-noise quotient, and/or T2* relaxation time.

4. The method of claim 3, wherein T2 or T2* relaxation times are determined using a 3D multi-echo sequence utilizing 2-12 echoes.

5. The method of claim 3, wherein signal intensity, signal-to-noise quotient, and/or T2* relaxation times are represented as mean values across an entire ACL or ACL graft, or represented on a voxel-wise basis.

6. The method of claim 1, wherein the MR parameters include a volume of the ACL or ACL graft.

7. The method of claim 1, wherein the MR parameters include a distribution of T2* values of the ACL or ACL graft.

8. The method of claim 1, wherein the MR imaging dataset includes a stack of MRI images.

9. The method of claim 1, wherein the predictive model includes:
terms characterized by a number of pixels in the MR imaging dataset within the defined region;
terms characterized by the MR image parameters within each pixel of the defined region;
terms characterized by an average in the defined region;
terms characterized by specific regions of interest within a ligament, graft, or tendon; or
terms characterized by more than one set of acquired MR imaging parameters.

10. The method of claim 1, wherein the predictive model is generated, the generating including performing multivariable regression analyses to determine relationships between the MR imaging parameters and failure properties of the ACL or ACL graft.

11. The method of claim 1 wherein the MR imaging data set is acquired using imaging sequences that include 3-dimensional (3D) gradient multiple-echo sequences, multi-echo spin echo or multi-echo fast spin sequence.

12. The method of claim 1, wherein the predictive model is generated by at least calculating and mapping T2* values in order to predict failure loads or to create a failure risk score, the predictive models generated using preclinical T2* distributions in ACL or ACL graft and relating to failure properties.

13. The method of claim 1, wherein the score characterizes a yield load, a failure load and/or a linear stiffness value.

14. The method of claim 13, wherein the score is proportional to yield load, failure load, and linear stiffness values of the ACL or ACL graft.

15. The method of claim 1, further comprising:
determining cross-sectional area of the ACL or ACL graft; and
determining length of the ACL or ACL graft.

16. The method of claim 15, further comprising
using the determined cross-sectional area and determined length as inputs to a second predictive model; and
generating, using the second predictive model, a second score, wherein the score characterizes a yield stress, a failure stress or a modulus of a structure of interest.

17. The method of claim 1, wherein the MR imaging data set includes MR parameters that characterizes a contrast between the ACL or ACL graft and surrounding tissues and fluids.

18. The method of claim 1, wherein the MR imaging data set includes T2* relaxation time, 3D gradient multi-echo, T1-weighted gradient echo, or proton density sequences.

19. The method of claim 1, further comprising: measuring ligament size using segmentation performed manually, semi-automatically, or automatically.

20. The method of claim 1, further comprising normalizing an ACL or ACL graft signal intensity by at least dividing the signal intensity of the ACL or ACL graft by a signal intensity of a region of bone, posterior cruciate ligament, patellar tendon, menisci, fat, or other soft tissue structures in or about the knee.

21. The method of claim 1, wherein the predictive model is generated using MR parameters derived from images acquired at a single time point during healing.

22. The method of claim 1, wherein the predictive model is generated using MR parameters derived from images acquired at multiple time points during healing.

23. The method of claim 1, wherein the MR imaging dataset includes data acquired at a single time point during healing.

24. The method of claim 1, wherein the MR imaging dataset includes data acquired at multiple time points during healing.

25. The method of claim 1, further comprising:
obtaining a second MR imaging dataset for an ACL of a contralateral knee;
deriving, using the second MR imaging dataset, second MR parameters that characterize a size and a quality of an ACL of the contralateral knee; and
dividing the MR specific parameters by the second MR specific parameters for the ACL of the contralateral knee.

26. The method of claim 1, further comprising:
dividing the MR imaging parameters by imaging parameters derived for a second structure.

27. The method of claim 26, wherein the second structure includes cancellous bone, cortical bone, fat, muscle, ligament, or tendon within the body.

28. The method of claim 26, wherein the signal intensity of a tissue in a contralateral knee is used in the predictive model to standardize the score characterizing the risk of failure of the ACL or ACL graft in a human patient.

29. The method of claim 26, wherein the signal intensity of a tissue in the contralateral knee is used in the predictive model to standardize the score, the score characterizing the likelihood of future clinical outcomes of the ACL or ACL graft in a human patient.

30. The method of claim 1, further comprising:
obtaining a second MR imaging dataset for an ACL of a contralateral knee, wherein the predictive model is generated using second MR specific parameters for the ACL of the contralateral knee for failure prediction of an injured knee.

31. The method of claim 1, further comprising:
administering, based on the score, a treatment protocol to the patient.

32. The method of claim 31, wherein the treatment protocol includes avoidance of stress on the knee for a predefined period of time.

33. A system for synthetic image generation for magnetic resonance (MR) imaging including a processor configured to execute computer-executable instructions to cause the system to perform operations comprising:
defining a region on a scan comprising one or more of an anterior cruciate ligament (ACL) or an ACL graft;
obtaining a magnetic resonance (MR) imaging data set within the region;
deriving, using the MR imaging data, MR parameters that characterize a size and a quality of the ACL or the ACL graft;
using the MR parameters as inputs to a predictive model; and
generating, using the predictive model, a score characterizing a likelihood of failure of the ACL or ACL graft in a human patient;
wherein acquiring a MR imaging data set is performed using the magnetic resonance imaging (MRI) system including a 1.5T to 11T magnet.

34. The system of claim 33, wherein the processor is further configured to present imaging data for visual assessment and present the score.

35. The system of claim 34, wherein the system includes an MR image processing workstation or a picture archiving and communication system.

36. A method to noninvasively predict the failure risk of an anterior cruciate ligament (ACL) surgery using magnetic resonance (MR) imaging, the method comprising:
defining an region of a scan comprising an ACL or an ACL graft;
acquiring a MR imaging dataset within the region;
obtaining MR parameters that define a size and quality of the ACL or ACL graft from the MR image dataset;
obtaining second MR specific parameters for the ACL of a contralateral knee;
using the MR parameters from both knees as inputs to a predictive model; and
generating a score that correlates to the risk of failure of the ACL or ACL graft in a human patient;
wherein acquiring the MR imaging data set is performed using the magnetic resonance imaging (MRI) system including a 1.5T to 11T magnet.

37. The method of claim 36, further comprising:
administering, based on the score, a treatment protocol to the patient.

38. A non-transitory computer program product storing instructions, which when executed by at least one data processor of at least one computing system, implement operations comprising:
defining a region on a scan comprising one or more of an anterior cruciate ligament (ACL) or an ACL graft;
obtaining a magnetic resonance (MR) imaging data set within the region;
deriving, using the MR imaging data, MR parameters that characterize a size and a quality of the ACL or the ACL graft;
using the MR parameters as inputs to a predictive model; and
generating, using the predictive model, a score characterizing a likelihood of failure of the ACL or ACL graft in a human patient;
wherein acquiring a magnetic resonance (MR) imaging data set is performed using a magnetic resonance imaging (MRI) system including a 1.5T to 11T magnet.

39. A method comprising:
defining a region on a scan comprising one or more of an anterior cruciate ligament (ACL) or an ACL graft;
obtaining a magnetic resonance (MR) imaging data set within the region;
deriving, using the MR imaging data, MR parameters that characterize a size and a quality of the ACL or the ACL graft;
using the MR parameters as inputs to a predictive model; and
generating, using the predictive model, a score characterizing a likelihood of failure of the ACL or ACL graft in a human patient;
wherein the MR parameters include a volume of the ACL or ACL graft.

40. The method of claim 39, wherein the likelihood of failure includes a future clinical outcome including failure of the ACL or ACL graft.

41. The method of claim 39, wherein the MR parameters include signal intensity, signal-to-noise quotient, and/or T2* relaxation time.

42. The method of claim 41, wherein T2 or T2* relaxation times are determined using a 3D multi-echo sequence utilizing 2-12 echoes.

43. The method of claim 41, wherein signal intensity, signal-to-noise quotient, and/or T2* relaxation times are represented as mean values across an entire ACL or ACL graft, or represented on a voxel-wise basis.

44. The method of claim 39, wherein the MR parameters include a volume of the ACL or ACL graft.

45. The method of claim 39, wherein the MR parameters include a distribution of T2* values of the ACL or ACL graft.

46. The method of claim 39, wherein the MR imaging dataset includes a stack of MRI images.

47. The method of claim 39, further comprising:
obtaining a second MR imaging dataset for an ACL of a contralateral knee;
deriving, using the second MR imaging dataset, second MR parameters that characterize a size and a quality of an ACL of the contralateral knee; and
dividing the MR specific parameters by the second MR specific parameters for the ACL of the contralateral knee.

48. The method of claim 39, wherein the MR imaging data set includes MR parameters that characterizes a contrast between the ACL or ACL graft and surrounding tissues and fluids.

49. A system comprising at least one data processor and memory storing instructions which, when executed by the at least one data processor, causes the at least one data processor to perform operations comprising:
defining a region on a scan comprising one or more of an anterior cruciate ligament (ACL) or an ACL graft;
obtaining a magnetic resonance (MR) imaging data set within the region;
deriving, using the MR imaging data, MR parameters that characterize a size and a quality of the ACL or the ACL graft;
using the MR parameters as inputs to a predictive model; and
generating, using the predictive model, a score characterizing a likelihood of failure of the ACL or ACL graft in a human patient;
wherein the MR parameters include a volume of the ACL or ACL graft.

50. The system of claim 49, wherein the likelihood of failure includes a future clinical outcome including failure of the ACL or ACL graft.

51. The system of claim 49, wherein the MR parameters include signal intensity, signal-to-noise quotient, and/or T2* relaxation time.

52. The system of claim 51, wherein T2 or T2* relaxation times are determined using a 3D multi-echo sequence utilizing 2-12 echoes.

53. The system of claim 51, wherein signal intensity, signal-to-noise quotient, and/or T2* relaxation times are represented as mean values across an entire ACL or ACL graft, or represented on a voxel-wise basis.

54. The system of claim 49, wherein the MR parameters include a volume of the ACL or ACL graft.

55. The system of claim 49, wherein the MR parameters include a distribution of T2* values of the ACL or ACL graft.

56. The system of claim 49, wherein the MR imaging dataset includes a stack of MRI images.

57. The system of claim 49, the operations further comprising:
obtaining a second MR imaging dataset for an ACL of a contralateral knee;
deriving, using the second MR imaging dataset, second MR parameters that characterize a size and a quality of an ACL of the contralateral knee; and
dividing the MR specific parameters by the second MR specific parameters for the ACL of the contralateral knee.

58. The system of claim 49, wherein the MR imaging data set includes MR parameters that characterizes a contrast between the ACL or ACL graft and surrounding tissues and fluids.

* * * * *